(12) United States Patent
Kuwahara

(10) Patent No.: US 10,385,090 B2
(45) Date of Patent: Aug. 20, 2019

(54) NUCLEOTIDE DERIVATIVE OR SALT THEREOF, NUCLEOTIDE-DERIVED 5'-PHOSPHATE ESTER OR SALT THEREOF, NUCLEOTIDE-DERIVED 3'-PHOSPHORAMIDITE COMPOUND OR SALT THEREOF, AND POLYNUCLEOTIDE

(71) Applicant: NATIONAL UNIVERSITY CORPORATION GUNMA UNIVERSITY, Maebashi-shi, Gunma (JP)

(72) Inventor: Masayasu Kuwahara, Maebashi (JP)

(73) Assignee: NATIONAL UNIVERSITY CORPORATION GUNMA UNIVERSITY, Maebashi (JP)

( * ) Notice: Subject to any disclaimer, the term of this patent is extended or adjusted under 35 U.S.C. 154(b) by 467 days.

(21) Appl. No.: 15/032,623

(22) PCT Filed: Sep. 10, 2014

(86) PCT No.: PCT/JP2014/073987
§ 371 (c)(1),
(2) Date: Apr. 27, 2016

(87) PCT Pub. No.: WO2015/064223
PCT Pub. Date: May 7, 2015

(65) Prior Publication Data
US 2016/0311845 A1 Oct. 27, 2016

(30) Foreign Application Priority Data

Oct. 31, 2013 (JP) .................. 2013-227466

(51) Int. Cl.
| | |
|---|---|
| C07H 19/20 | (2006.01) |
| C07H 19/073 | (2006.01) |
| C07H 19/10 | (2006.01) |
| C12N 15/115 | (2010.01) |
| C07H 19/16 | (2006.01) |
| C12N 15/10 | (2006.01) |

(Continued)

(52) U.S. Cl.
CPC ........... *C07H 19/20* (2013.01); *C07H 19/073* (2013.01); *C07H 19/10* (2013.01); *C07H 19/16* (2013.01); *C07H 19/173* (2013.01); *C12N 15/1048* (2013.01); *C12N 15/111* (2013.01); *C12N 15/115* (2013.01); *C12N 2310/16* (2013.01); *C12N 2310/315* (2013.01); *C12N 2320/51* (2013.01); *C12N 2330/31* (2013.01)

(58) Field of Classification Search
CPC .... C07H 19/073; C07H 19/173; C07H 19/10; C07H 19/16; C07H 19/20; C12N 15/115; C12N 15/1048; C12N 15/111; C12N 2310/16; C12N 2310/315; C12N 2320/51; C12N 2330/31
See application file for complete search history.

(56) References Cited

U.S. PATENT DOCUMENTS

| | | | | |
|---|---|---|---|---|
| 4,458,066 A | * | 7/1984 | Caruthers | ............ B01J 19/0046 536/25.34 |
| 4,500,707 A | * | 2/1985 | Caruthers | ............ B01J 19/0046 536/25.34 |

(Continued)

FOREIGN PATENT DOCUMENTS

| | | |
|---|---|---|
| JP | 2012-200204 A | 10/2012 |
| JP | 2013-040118 A | 2/2013 |

(Continued)

OTHER PUBLICATIONS

Caruthers (I), "Gene Synthesis Machines: DNA Chemistry and Its Uses," Science, 230, 281-285 (Oct. 18, 1985).*
Caruthers (II), "A Brief Review of DNA and RNA Chemical Synthesis," Biochem. Soc. Trans., 39, 575-580 (2011).*
The International Bureau of WIPO, International Preliminary Report on Patentability in International Patent Application No. PCT/JP2014/073987 (dated May 12, 2016).

(Continued)

*Primary Examiner* — Lawrence E Crane
(74) *Attorney, Agent, or Firm* — Leydig, Voit & Mayer, Ltd.

(57) ABSTRACT

Disclosed is a nucleoside derivative of formulae (I-1) or a salt thereof:

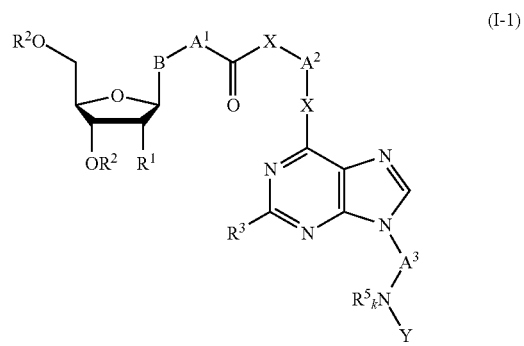

in which $R^1$, $R^2$, $R^3$, $R^5$, $A^1$ to $A^3$, B, X, Y, and k are described herein. Also provided are a 5'-phosphate ester and a 3'-phosphoramidite derivative of the nucleoside derivative and substrate solutions thereof. A polynucleotide is produced using the 5'-phosphate ester or 3'-phosphoramidite derivative of the nucleoside derivative. A library of the produced polynucleotide is used in a method of selecting a nucleic acid aptamer. Further provided is a vesicular endothelial growth factor binding agent of formula (i).

13 Claims, 13 Drawing Sheets
Specification includes a Sequence Listing.

(51) Int. Cl.
   *C07H 19/173* (2006.01)
   *C12N 15/11* (2006.01)

(56) References Cited

U.S. PATENT DOCUMENTS

| | | | | |
|---|---|---|---|---|
| 4,668,777 A | * | 5/1987 | Caruthers | C07H 21/00 536/26.5 |
| 4,973,679 A | * | 11/1990 | Caruthers | C07H 21/00 536/25.3 |
| 5,132,418 A | * | 7/1992 | Caruthers | B01J 19/0046 536/25.3 |
| 9,090,896 B2 | * | 7/2015 | Itoh | C07K 14/695 |
| 2011/0144187 A1 | | 6/2011 | Wang et al. | |
| 2014/0322821 A1 | | 10/2014 | Itoh et al. | |

FOREIGN PATENT DOCUMENTS

| | | |
|---|---|---|
| WO | WO 2010/019847 A2 | 2/2010 |
| WO | WO 2013/099762 A1 | 7/2013 |

OTHER PUBLICATIONS

Japanese Patent Office, International Search Report in International Patent Application No. PCT/JP2014/073987 (dated Nov. 18, 2014).

* cited by examiner

| Time | Area | Area % | Height | Height % |
|---|---|---|---|---|
| 12.383 | 65666 | 0.04 | 23 | 0.00 |
| 14.425 | 183004459 | 99.96 | 6003065 | 100.00 |
| Totals | 183070125 | 100.00 | 6003088 | 100.00 |

| Time | Area | Area % | Height | Height % |
|---|---|---|---|---|
| 12.846 | 51501 | 0.01 | 806 | 0.00 |
| 14.483 | 344830062 | 99.99 | 17125647 | 100.00 |
| Totals | 344881563 | 100.00 | 17126453 | 100.00 |

| Time | Area | Area % | Height | Height % |
|---|---|---|---|---|
| 12.846 | 259833 | 0.07 | 16868 | 0.10 |
| 14.542 | 363661741 | 99.93 | 17196449 | 99.90 |
| Totals | 363921574 | 100.00 | 17213317 | 100.00 |

• Sequences obtained from modified (KK10) library

KK10#07. TCCCTCGCAGGATCCAAGAAGATGATGATAAGCCGTCTATAGAGGGTGGACCGAGCAGTGGCAGCA (SEQ ID NO: 6)
KK10#18. TCCCTCGCAGGATCCAAGATCCATGTAACGCGTGTTAGCTCATAGGACTGGACCGAGCAGTGGCAGCA (SEQ ID NO: 7)
KK10#21. TCCCTCGCAGGATCCAAGTCAGAAGCTTGCCATGCTCATGAGTCTGGTGGACCGAGCAGTGGCAGCA (SEQ ID NO: 8)
KK10#24. TCCCTCGCAGGATCCACGGGCGAAGCCGAACAGATATTCTCTGATCCATGGACCGAGCAGTGGCACAA (SEQ ID NO: 9)
KK10#30. TCCCTCGCAGGATCCAAGGGCAGTGAGTTGTTAAGTACCGACATGAAGTGGACCGAGCAGTGGCAGCA (SEQ ID NO: 10)
KK10#32. TCCCTCGCAGGATCCAAGCGTGGATACGGTACTAAACGAAGTAACCCTTGGACCGAGCAGTGGCAGCA (SEQ ID NO: 11)
KK10#35. TCCCTCGCAGGATCCAAGCCGAGACTGCGTTGTAGGGCAAGTGGCAATGGACCGAGCAGTGGCAGCA (SEQ ID NO: 12)
KK10#36. TCCCTCGCAGGATCCAACGGGTGACCGGTTCATTCTTAATTTACAATGGACCGAGCAGTGGCAGCA (SEQ ID NO: 13)
KK10#39. TCCCTCGCAGGATCCAAGGAACTCTACCTAGACTACGTACTTGCCGCTGGACCGAGCAGTGGCAGCA (SEQ ID NO: 14)
KK10#42. TCCCTCGCAGGATCCAAGACAGACCACAGCTGACTTGTATACAGAAGTGGACCGAGCAGTGGCAGCA (SEQ ID NO: 15)
KK10#48. TCCCTCGCAGGATCCACGGCTGAACTTGTATTCACGCGGTAACACATGGACCGAGCAGTGGCAGCA (SEQ ID NO: 16)
KK10#55. TCCCTCGCAGGATCCAAGAGCGGGGTTAGTATAGTTCTGGAATGAAGTTGGACCGAGCAGTGGCAGCA (SEQ ID NO: 17)
KK10#58. TCCCTCGCAGGATCCAAGATAGCATCCACGGTTTCTAATTGCTACGCTGGACCGAGCAGTGGCAGCA (SEQ ID NO: 18)
KK10#67. TCCCTCGCAGGATCCAAGCGTGAGAAGATGCCGGTGAGGTTGAGTGGACCGAGCAGTGGCAGCA (SEQ ID NO: 19)

KK10#01. TCCCTCGCAGGATCCAAGGACAAGTACCTTGCAGCGGTCACTACCTTGGACCGAGCAGTGGCAGCA (SEQ ID NO: 20)
KK10#46. TCCCTCGCAGGATCCAAGGACATGTACCTTGCACGCGTCACTACCTTGGACCGAGCAGTGGCAGCA (SEQ ID NO: 21)

KK10#29. TCCCTCGCAGGATCCAAGGAGTTCATGAGGGAAAATGTGGGGTGACTTGGACCGAGCAGTGGCAGCA (SEQ ID NO: 22)
KK10#64. TCCCTCGCAGGATCCAAGGAGTTCATGAGGGAAAATGTGGGGTGACTTGGACCGAGCAGTGGCAGCA (SEQ ID NO: 23)

KK10#38. TCCCTCGCAGGATCCAAGCTAGCGTGTCGCACGAACTAACAAAACTGTGGACCGAGCAGTGGCAGCA (SEQ ID NO: 24)
KK10#54. TCCCTCGCAGGATCCACGCTAGCGTGTCGCACGAACTAACAAAACTGTGGACCGAGCAGTGGCAGCA (SEQ ID NO: 25)

KK10#26. TCCCTCGCAGGATCCAAGTATGGCCGGATGGCATAGGATTCTCCTTGTGGACCGAGCAGTGGCAGCA (SEQ ID NO: 26)
KK10#33. TCCCTCGCAGGATCCAAGTATGGCCGGATGGCATAGGATTCTCCTTGTGGACCGAGCAGTGGCAGCA (SEQ ID NO: 26)
KK10#45. TCCCTCGCAGGATCCACGTATGGCCGGATGGCATAGGATTCTCCTTGTGGACCGAGCAGTGGCAGCA (SEQ ID NO: 27)

KK10#05. TCCCTCGCAGGATCCACGAAGTTCATGAAAAAATAAACGTGGTCCATGGACCGAGCAGTGGCAGCA (SEQ ID NO: 28)
KK10#10. TCCCTCGCAGGATCCAAGGAGGTTCATGAAAAAATAAACGTGGTCCATGGACCGAGCAGTGGCAGCA (SEQ ID NO: 29)
KK10#23. TCCCTCGCAGGATCCAAGGAGGTTCATGAAAAAATAAACGTGGTCCATGGACCGAGCAGTGGCAGCA (SEQ ID NO: 29)
KK10#31. TCCCTCGCAGGATCCAAGGAGGTTCATGAAGAAATAAACGGTGGTCCATGGACCGAGCAGTGGCAGCA (SEQ ID NO: 30)

KK10#08. TCCCTCGCAGGATCCAAGAGCGTGAGAGCTTAGAATTCCCACTTGAGCTGGACCGAGCAGTGGCAGCA (SEQ ID NO: 31)
KK10#51. TCCCTCGCAGGATCCAAGACGTGAGACCTTAGAATCCCACTTGAGCTGGACCGAGCAGTGGCAGCA (SEQ ID NO: 32)
KK10#56. TCCCTCGCAGGATCCATGAGCGTGAGAGCTTAGAATTCCCACTTGAGCTGGACCGAGCAGTGGCAGCA (SEQ ID NO: 33)
KK10#59. TCCCTCGCAGGATCCAAGAGCGTGAGAGCTTAGAATTCCCACTTGAGCTGGACCGAGCAGTGGCAGCA (SEQ ID NO: 31)
KK10#70. TCCCTCGCAGGATCCACGAGCGTGAGAGCTTAGAATTCCCACTTGAGCTGGACCGAGCAGTGGCAGCA (SEQ ID NO: 34)

Fig. 11-1

KKIG#04. TGGCTGGCAGGATCCCAAGTCGCGTTTAAGGGTAAGTAGGGCATTGTCATCGACCGAGCAGTGGCAGCA (SEQ ID NO: 35)
KKIG#09. TGGCTGGCAGGATCCCAAGTCGCGTTTAAGGGTAAGTAGGGCATTGCCATCGACCGAGCAGTGGCAGCA (SEQ ID NO: 36)
KKIG#12. TGGCTGGCAGGATCCCAAGTCGCGTTTAAGGGTAAGTAGGGCATTGTCATCGACCGAGCAGTGGCAGCA (SEQ ID NO: 35)
KKIG#13. TGGCTGGCAGGATCCCAAGTCGCGTTTAAGGGTAAGTAGGGCATTGTCATCGACCGAGCAGTGGCAGCA (SEQ ID NO: 35)
KKIG#16. TGGCTGGCAGGATCCCAAGTCGCGTTTAAGGGTAAGTAGGGCATTGTCATCGACCGAGCAGTGGCAGCA (SEQ ID NO: 35)
KKIG#17. TGGCTGGCAGGATCCCAAGTCGCGTTTAAGGGTAAGTAGGGCATTGTCATCGACCGAGCAGTGGCAGCA (SEQ ID NO: 35)
KKIG#19. TGGCTGGCAGGATCCCAAGTCGCGTTTAAGGGTAAGTAGGGCATTGTCATCGACCGAGCAGTGGCAGCA (SEQ ID NO: 35)
KKIG#20. TGGCTGGCAGGATCCCAAGCCGCGTTTAAGGGTAAGTAGGGCATTGTCATCGACCGAGCAGTGGCAGCA (SEQ ID NO: 37)
KKIG#25. TGGCTGGCAGGATCCCAAGTCGCGTTTAAGGGTAAGTAGGGCATTGTCATCGACCGAGCAGTGGCAGCA (SEQ ID NO: 35)
KKIG#28. TGGCTGGCAGGATCCCACGTCGCGTTTAAGGGTAAGTAGGGCATTGTCATCGACCGAGCAGTGGCAGCA (SEQ ID NO: 38)
KKIG#34. TGGCTGGCAGGATCCCAAGTCGCGTTTAAGGGTAAGTAGGGCATTGTCATCGACCGAGCAGTGGCAGCA (SEQ ID NO: 35)
KKIG#41. TGGCTGGCAGGATCCCAAGTCGCGTTTAAGGGTAAGTAGGGCATTGTCATCGACCGAGCAGTGGCAGCA (SEQ ID NO: 35)
KKIG#43. TGGCTGGCAGGATCCCACGTCGCGTTTAAGGGTAAGTAGGGCATTGTCATCGACCGAGCAGTGGCAGCA (SEQ ID NO: 38)
KKIG#44. TGGCTGGCAGGATCCCAAGTCGCGTTTAAGGGAAAGTAGGGCATTGTCATCGACCGAGCAGTGGCAGCA (SEQ ID NO: 39)
KKIG#47. TGGCTGGCAGGATCCCAAGTCGAGTTTAAGGGTAAGTAGGGCATTGTCATCGACCGAGCAGTGGCAGCA (SEQ ID NO: 40)
KKIG#67. TGGCTGGCAGGATCCCAAGTCGCGTTTAAGGGTAAGTAGGGCATTGTCATCGACCGAGCAGTGGCAGCA (SEQ ID NO: 35)

|  | VEGF (nM) | Mean value in complex | S.D. | Relative value in complex |
|---|---|---|---|---|
| KK10VEGF#36 | 0.00 | 0.00 | 0.00 | 0.00 |
|  | 0.25 | 7.94 | 0.41 | 29.53 |
|  | 0.50 | 12.39 | 0.78 | 46.11 |
|  | 1.00 | 20.08 | 1.39 | 74.71 |
|  | 1.50 | 24.29 | 2.16 | 90.38 |
|  | 2.00 | 24.48 | 2.58 | 91.08 |
|  | 3.00 | 26.88 | 1.45 | 100.00 |
|  | 5.00 | 26.76 | 1.15 | 99.57 |
|  | 50.00 | 24.59 | 0.78 | 91.46 |

$K_d = 0.486$ (nM)

KK10#38

|  | VEGF (nM) | Mean value in complex | S.D. | Relative value in complex |
|---|---|---|---|---|
| KK10VEGF#38 | 0.00 | 0.00 | 0.00 | 0.00 |
|  | 0.25 | 2.26 | 0.20 | 7.04 |
|  | 0.50 | 5.20 | 0.76 | 16.20 |
|  | 1.00 | 9.12 | 0.70 | 28.40 |
|  | 1.50 | 12.27 | 0.77 | 38.21 |
|  | 2.00 | 11.54 | 0.45 | 35.96 |
|  | 3.00 | 16.93 | 0.31 | 52.74 |
|  | 5.00 | 23.57 | 0.52 | 73.42 |
|  | 50.00 | 32.10 | 0.98 | 100.00 |

$K_d = 2.86$ (nM)

NUCLEOTIDE DERIVATIVE OR SALT THEREOF, NUCLEOTIDE-DERIVED 5'-PHOSPHATE ESTER OR SALT THEREOF, NUCLEOTIDE-DERIVED 3'-PHOSPHORAMIDITE COMPOUND OR SALT THEREOF, AND POLYNUCLEOTIDE

CROSS-REFERENCE TO RELATED APPLICATIONS

This patent application is the U.S. national phase of International Patent Application No. PCT/JP2014/073987, filed Sep. 10, 2014, which claims the benefit of Japanese Patent Application No. 2013-227466, filed on Oct. 31, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 65,621,101 bytes ASCII (Text) file named "723976SequenceListing.txt," created Apr. 26, 2016.

TECHNICAL FIELD

The present invention relates to a novel nucleoside derivative and a salt thereof, a 5'-phosphate ester of the nucleoside derivative and a salt thereof, a 3'-phosphoramidite compound of the nucleoside derivative and a salt thereof, and a polynucleotide; and relates to, more particularly, a nucleic acid aptamer with excellent binding affinity, a novel nucleoside derivative that is useful for producing the nucleic acid aptamer, and the like.

BACKGROUND ART

Nucleic acid (DNA, RNA, PNA) aptamers that specifically bind to their target substances have been studied for their biotechnological application and pharmaceutical application as biological substances capable of recognizing molecules alternative to antibodies. As methods of obtaining these nucleic acid aptamers, SELEX (Systematic Evolution of Ligands by Exponential Enrichment) method has been known. For example, it is known that nucleic acid aptamers that specifically bind to a target substance are able to be found by carrying out screening of a mixture (library) of a large number of nucleic acid molecules having random sequence.

Meanwhile, there are also many reports about examples of use of the nucleic acid aptamer as a pharmaceutical. For example, Patent Document 1 discloses an invention of an RNA aptamer having a specific nucleotide sequence and reports that the RNA aptamer specifically binds to hirame rhabdovirus (HIRRV) or a polypeptide expressed in the virus to function to inhibit the ability of the virus to infect a host.

In addition, Patent Document 2 discloses an invention of nucleic acid aptamer (artificial nucleic acid molecule) that specifically binds to camptothecins such as irinotecan or topotecan and reports that a modified nucleoside structure in which a purine structure is linked to a thymidine moiety (which binds to the C5 position) via a carbon chain produces excellent binding affinity.

PRIOR ART REFERENCES

Patent Documents

Patent Document 1: Japanese Patent Application Laid-Open Publication No. 2012-200204
Patent Document 2: Japanese Patent Application Laid-Open Publication No. 2013-040118

SUMMARY OF THE INVENTION

Nucleic acid aptamers that specifically bind to a target substance can be found by employing, for example, SELEX method; yet it is also important to find a new chemical structure with excellent binding affinity as exemplified by the modified nucleoside structure described in Patent Document 2 in order to develop an excellent nucleic acid aptamer in an efficient fashion.

Accordingly, an object of the present invention is to provide a modified nucleoside structure with excellent binding affinity, provide an excellent nucleic acid aptamer, and provide a novel compound that is useful for producing a nucleic acid aptamer.

In order to solve the above problems, the present inventors have intensively studied and found that the binding affinity and the target variety can be improved by introducing a nitrogen atom-containing functional group such as an amino group or a carbon chain that contains such a functional group to a modified nucleoside structure with a purine structure being linked to form intramolecular or intermolecular interaction, thereby completed the present invention.

That is, the present invention is as follows.
<1> A nucleoside derivative represented by any one of the following formulae (I-1) to (I-6) or a salt thereof:

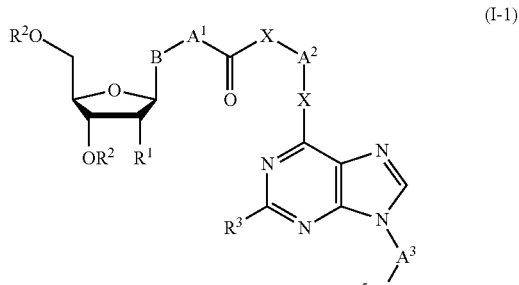

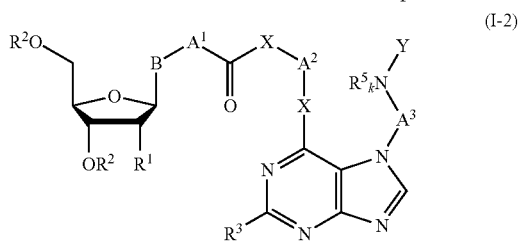

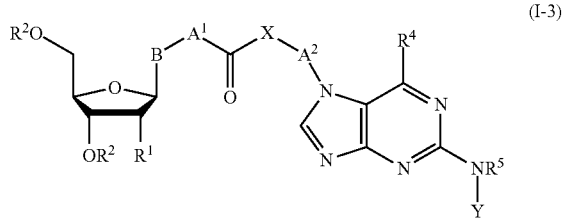

-continued

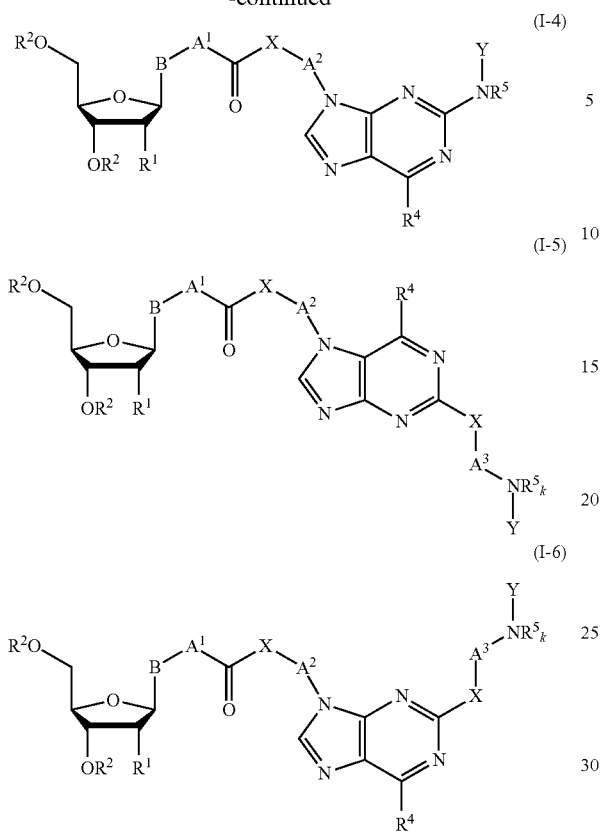

(I-4)

(I-5)

(I-6)

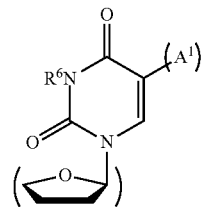

(II-1)

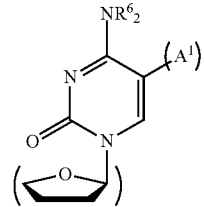

(II-2)

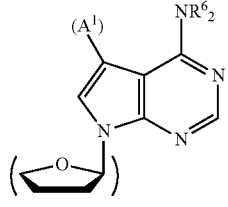

(II-3)

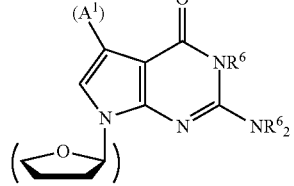

(II-4)

in the formulae (I-1) to (I-6), $R^1$ represents a hydrogen atom (—H), a fluorine atom (—F), a hydroxyl group (—OH), an amino group (—NH$_2$), or a mercapto group (—SH); each $R^2$ independently represents a hydrogen atom (—H) or a protective group of a hydroxyl group; $R^3$ and $R^4$ represent a hydrogen atom (—H), a hydroxyl group (—OH), an amino group (—NR$^5{}_2$), a mercapto group (—SH), or a hydrocarbon group having one to 20 carbon atoms that may contain at least one selected from the group consisting of a nitrogen atom, an oxygen atom, and a sulfur atom; each $R^5$ independently represents a hydrogen atom (—H) or a hydrocarbon group having one to six carbon atoms; $A^1$ represents a divalent hydrocarbon group having two to ten carbon atoms that may contain a branched structure and/or an unsaturated bond; $A^2$ and $A^3$ each independently represents a divalent hydrocarbon group having two to 12 carbon atoms that may contain a branched structure and/or an unsaturated bond; B represents a base structure represented by any of the following formulae (II-1) to (II-4); each X independently represents an imino group (—NR$^5$—), an ether group (—O—), or a thioether group (—S—); Y represents a hydrogen atom (—H) or a hydrocarbon group having one to 20 carbon atoms that may contain at least one selected from the group consisting of a nitrogen atom, an oxygen atom, a sulfur atom, and a halogen atom, and k represents 1 or 2:

in the formulae (II-1) to (II-4), each $R^6$ independently represents a hydrogen atom (—H), a hydrocarbon group having one to six carbon atoms, or a protective group of an amino group.

<2> A 5'-phosphate ester of the nucleoside derivative according to <1> or a salt thereof.

<3> A 3'-phosphoramidite product of the nucleoside derivative according to <1> or a salt thereof.

<4> A substrate solution for polynucleotide synthesis that contains the 5'-phosphate ester or a salt thereof according to <2>, the 3'-phosphoramidite product or a salt thereof according to <3>, or a labeled nucleotide derivative obtained by introducing a labeling substance to the 5'-phosphate ester, the 3'-phosphoramidite product, or the salt thereof.

<5> A reagent for polynucleotide synthesis that contains the substrate solution for polynucleotide synthesis according to <4>.

<6> A method of producing a polynucleotide comprising using, as a substrate for synthesis, the 5'-phosphate ester or a salt thereof according to <2>, the 3'-phosphoramidite product or a salt thereof according to <3>, or a labeled nucleotide derivative obtained by introducing a labeling substance to said 5'-phosphate ester, said 3'-phosphoramidite product, or salt thereof.

<7> The method of producing a polynucleotide according to <6>, comprising the step of introducing a phosphorothioate group.

<8> A polynucleotide that contains, as a building block, the 5'-phosphate ester of the nucleoside derivative according to <2> and/or a phosphorothioated product thereof.

<9> The polynucleotide according to <8> which is a nucleic acid aptamer.
<10> A polynucleotide library that contains the polynucleotide according to <8> or <9>.
<11> A method of selecting a nucleic acid aptamer, comprising the step of selecting a target substance-binding polynucleotide by using the polynucleotide library according to <10>.
<12> A vesicular endothelial growth factor binding agent that contains a nucleic acid aptamer containing a residue of the modified nucleic acid presented by the following (i).
<13> The vesicular endothelial growth factor binding agent according to <12>, wherein the nucleic acid aptamer is a single-stranded DNA.
<14> The vesicular endothelial growth factor binding agent according to <12> or <13>, wherein the nucleic acid aptamer has a length of 15 to 100 bases.
<15> The vesicular endothelial growth factor binding agent according to any one of <12> to <14>, wherein the sequence of the nucleic acid aptamer contains the sequence of nucleotides 21 to 50 of any of SEQ ID NOs: 6 to 31 and 33 to 40 or nucleotides 21 to 49 of SEQ ID NO: 32 in which T in these sequences is the residue of the compound represented by the above (II).
<16> A method of selecting a vesicular endothelial growth factor binding agent, comprising the steps of: providing a library of nucleic acid aptamer that contains a residue of a modified nucleic acid of the following (i); reacting the library with a vesicular endothelial growth factor; and selecting and amplifying a nucleic acid aptamer that binds to the vesicular endothelial growth factor.

Effect of the Invention

According to the present invention, it is possible to provide a nucleic acid aptamer with excellent binding affinity and excellent target variety and to provide a novel compound that is useful for producing the nucleic acid aptamer. In addition, synthesis of a polynucleotide using the 5'-phosphate ester or 3'-phosphoramidite compound of the present invention makes it possible to enhance the performance of functional DNA created by SELEX method, to increase the efficacy of gene labeling, to functionalize an antisense or antigene molecule or siRNA.

BRIEF DESCRIPTION OF THE DRAWINGS

FIG. 11-1 is a figure showing the sequence of the VEGF-binding nucleic acid aptamer that comprises KK10 (the sequences of both terminal ends (underlined) represent the primer sequences; Ts that are not double-underlined and Ts that are single-underlined represent the KK10 residue; and Ts that are double-underlined represent thymine residue).
FIG. 11-2 is a figure showing the sequence of the VEGF-binding nucleic acid aptamer that comprises KK10 (the sequences of both terminal ends (underlined) represent the primer sequences; Ts that are not double-underlined and Ts that are single-underlined represent the KK10 residue; and Ts that are double-underlined represent thymine residue).

EMBODIMENTS FOR CARRYING OUT THE INVENTION

Figure 1:
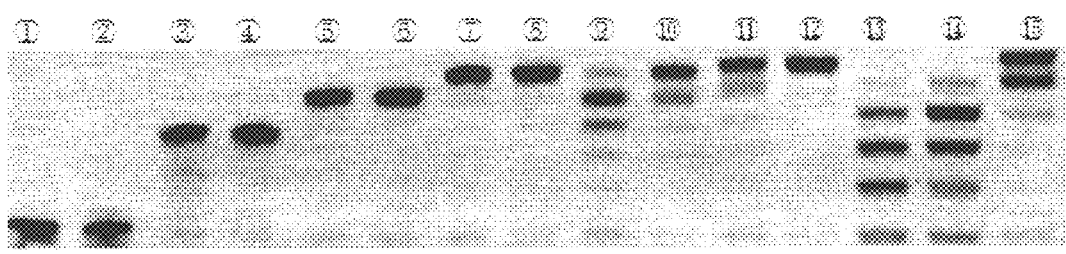
FIG. 1 is a photograph of polyacrylamide gel electrophoresis of the polynucleotide to which $dU^{ad}TP$ etc. has been introduced (drawing substituting photograph).

By way of specific examples, the nucleoside derivative and a salt thereof, the 5'-phosphate ester of nucleoside derivative and a salt thereof, the 3'-phosphoramidite compound of nucleoside derivative and a salt thereof, and the polynucleotide of the present invention will be described; yet the present invention is not limited to the following embodiments and can be modified as appropriate to be carried out without departing from the scope of the present invention.

<Nucleoside Derivatives or Salts Thereof>

The nucleoside derivative which is one aspect of the present invention is represented by any of the following formulae (I-1) to (I-6). It is to be noted that salts obtained from such a nucleoside derivative shall be included in the scope of the present invention and hereinafter, the nucleoside derivative and the salt thereof may be collectively shorten to "the nucleoside derivative or the like of the present invention".

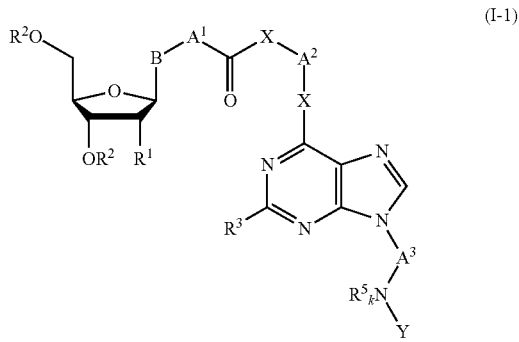

(I-1)

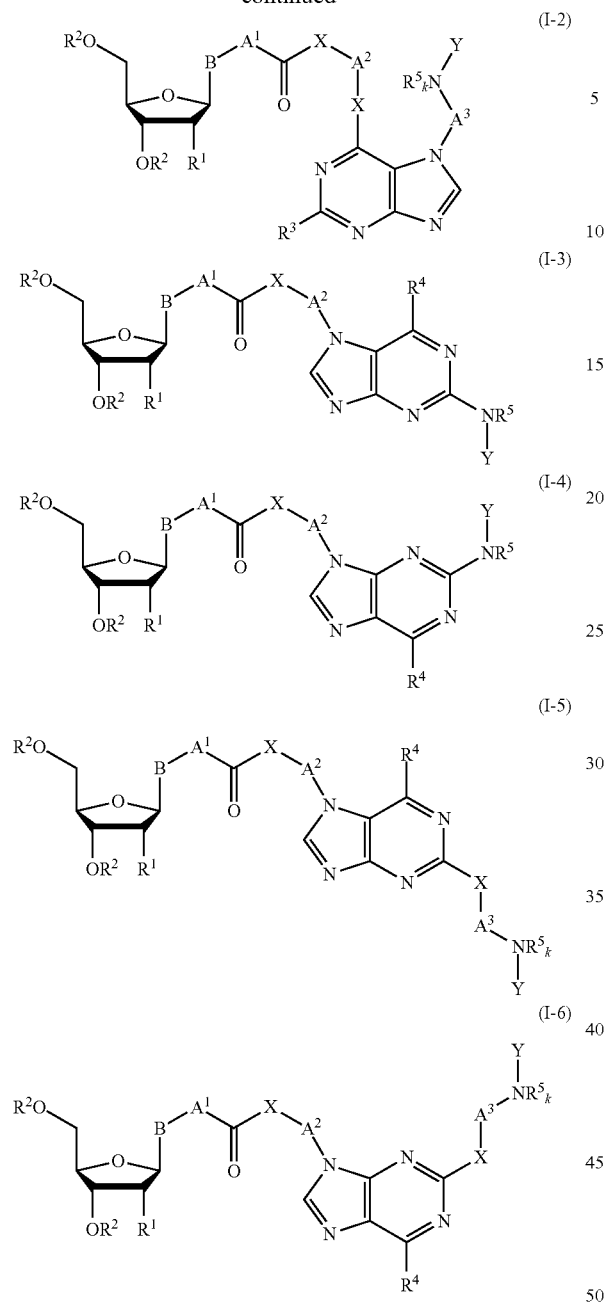

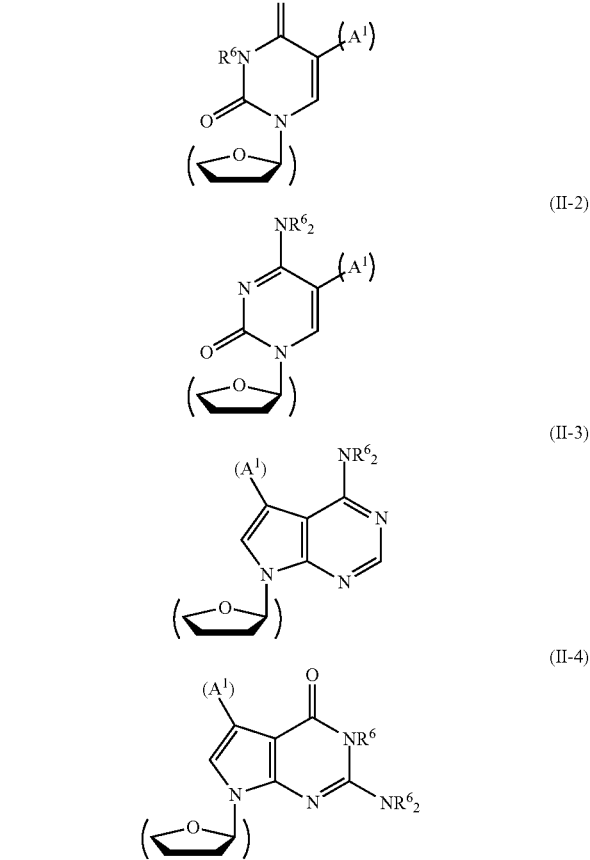

In the formulae (I-1) to (I-6), $R^1$ represents a hydrogen atom (—H), a fluorine atom (—F), a hydroxyl group (—OH), an amino group (—NH$_2$), or a mercapto group (—SH), each $R^2$ independently represents a hydrogen atom (—H) or a protective group of a hydroxyl group, $R^3$ and $R^4$ represent a hydrogen atom (—H), a hydroxyl group (—OH), an amino group (—NR$^5{}_2$), a mercapto group (—SH), or a hydrocarbon group having one to 20 carbon atoms that may contain at least one selected from the group consisting of a nitrogen atom, an oxygen atom, and a sulfur atom, each $R^5$ independently represents a hydrogen atom (—H) or a hydrocarbon group having one to six carbon atoms, $A^1$ represents a divalent hydrocarbon group having two to 10 carbon atoms that may contain a branched structure and/or an unsaturated bond, $A^2$ and $A^3$ each independently represents a divalent hydrocarbon group having two to 12 carbon atoms that may contain a branched structure and/or an unsaturated bond, B represents a base structure represented by any of the following formulae (II-1) to (II-4), each X independently represents an imino group (—NR$^5$—), an ether group (—O—), or a thioether group (—S—), Y represents a hydrogen atom (—H) or a hydrocarbon group having one to 20 carbon atoms that may contain at least one selected from the group consisting of a nitrogen atom, an oxygen atom, a sulfur atom, and a halogen atom, and k represents 1 or 2.

In the formulae (II-1) to (II-4), each $R^6$ independently represents a hydrogen atom (—H), a hydrocarbon group having one to six carbon atoms, or a protective group of an amino group.

Seeking for a modified nucleoside structure with excellent binding affinity, the present inventors have intensively studied to find that the binding affinity can be improved by introducing a nitrogen atom-containing functional group such as an amino group or a carbon chain that contains such a functional group to a modified nucleoside structure with a purine structure being linked as described in Patent Document 2 to form intramolecular or intermolecular interaction. The modified nucleoside structure with excellent binding affinity leads to improvement of the binding affinity and the target variety of a nucleic acid aptamer to which such a structure is introduced; and therefore the nucleoside derivative or the like of the present invention is a compound that is useful producing an excellent nucleic acid aptamer.

In the formulae (I-1) to (I-6), $R^1$ represents a hydrogen atom (—H), a fluorine atom (—F), a hydroxyl group (—OH), an amino group (—NH$_2$), or a mercapto group (—SH); and preferred is a hydrogen atom, that is, the sugar moiety of nucleoside derivative or the like is preferably deoxyribose.

Each $R^2$ independently represents a hydrogen atom (—H) or a protective group of a hydroxyl group; but the protective group is not particularly restricted as long as it is one that is used as a protective group of a hydroxyl group. Examples thereof include ether-based protective groups such as a methyl group, a benzyl group, a p-methoxybenzyl group, and a tert-butyl group; acyl-based protective groups such as an acetyl group, a pivaloyl group, and a benzoyl group; silylether-based protective groups such as a trimethylsilyl group, a triethylsilyl group, a tert-butyldimethylsilyl group, a triisopropylsilyl group, and a tert-butyldiphenylsilyl group.

$R^3$ and $R^4$ represent a hydrogen atom (—H), a hydroxyl group (—OH), an amino group (—NR$^5_2$), a mercapto group (—SH), or a hydrocarbon group having one to 20 carbon atoms that may contain at least one selected from the group consisting of a nitrogen atom, an oxygen atom, and a sulfur atom. It is to be noted that the phrase "may contain at least one selected from the group consisting of a nitrogen atom, an oxygen atom, and a sulfur atom" means that a functional group containing a nitrogen atom, an oxygen atom, a sulfur atom, or the like such as an amino group (—NH$_2$), a nitro group (—NO$_2$), a cyano group (—CN), an isocyanate group (—NCO), a hydroxyl group (—OH), an aldehyde group (—CHO), a carboxyl group (—COOH), a mercapto group (—SH), a sulfonic acid group (—SO$_3$H) or the like is allowed to be included; and the phrase, in addition, means that a linking group containing a nitrogen atom, an oxygen atom, a sulfur atom, or the like of an ether group (—O—), an imino group (—NH—), a thioether group (—S—), a carbonyl group (—C(=O)—), an amide group (—C(=O)—NH—), an ester group (—C(=O)—O—), a thioester group (—C(=O)—S—), or the like may be contained in the inside or the end of the carbon backbone. Therefore, examples of the "hydrocarbon group having one to 20 carbon atoms that may contain at least one selected from the group consisting of a nitrogen atom, an oxygen atom, and a sulfur atom" include a hydrocarbon group having two carbon atoms that contains a hydroxyl group such as —CH$_2$—CH$_2$—OH, a hydrocarbon group having two carbon atoms that contains an ether group inside of the carbon backbone such as —CH$_2$—O—CH$_3$, and a hydrocarbon group having two carbon atoms that contains an ether group at the end of the carbon backbone such as —O—CH$_2$—CH$_3$.

$R^3$ has preferably two or more carbon atoms and more preferably three or more carbon atoms; and preferably 15 or less carbon atoms and more preferably 12 or less carbon atom. It is preferred that $R^3$ be a hydrogen atom (—H), an amino group (—NH$_2$), or a hydrocarbon group having two to 15 carbon atoms that contains at least one selected from the group consisting of an amino group (—NH$_2$), an imino group (—NR$^5$—), an ether group (—O—), a thioether group (—S—), an amide group (—C(=O)—NR$^5$—), an ester group (—C(=O)—O—), and a thioester group (—C(=O)—S—). Examples of a specific structure of the hydrocarbon group in $R^3$ include one represented by the following formula:

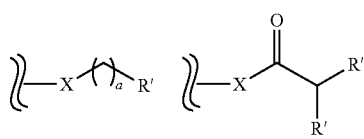

In the above formula, X represents an imino group (—NR$^5$—), an ether group (—O—), a thioether group (—S—); R' represents a hydrocarbon group having one to five carbon atoms; and a represents an integer of 0 to 6.

$R^4$ has preferably two or more carbon atoms and more preferably three or more carbon atoms; and preferably 15 or less carbon atoms and more preferably 12 or less carbon atom. It is preferred that $R^4$ be a hydroxyl group, an amino group, or a hydrocarbon group having two to 15 carbon atoms that contains a nitrogen atom and/or an oxygen atom. Examples of a specific structure of the hydrocarbon group in $R^4$ include one represented by the following formula:

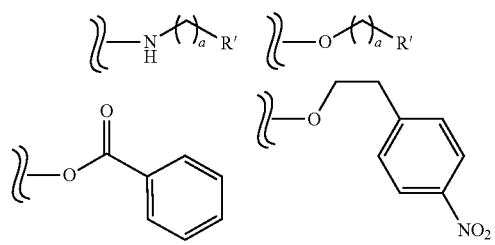

In the above formula, R' represents a hydrocarbon group having one to five carbon atoms; and a represents an integer of 0 to 6.

Each $R^5$ independently represents a hydrogen atom or a hydrocarbon group having one to six carbon atoms; and $R^5$ has preferably not more than five carbon atoms and more preferably not more than four carbon atoms.

$A^1$ represents a divalent hydrocarbon group having two to 10 carbon atoms that may contain a branched structure and/or an unsaturated bond; and $A^1$ has preferably not more than eight carbon atoms and more preferably not more than six carbon atoms. Examples of $A^1$ include an ethylene group (—CH$_2$—CH$_2$—), a vinylene group (—CH=CH—), an isopropylene group (—CH$_2$—CH(CH$_3$)—), an isopropyrenylene group (—CH=C(CH$_3$)—), a n-butylene group (—CH$_2$—CH$_2$—CH$_2$—CH$_2$—), and a n-butandienylene group (—CH=CH—CH=CH—).

$A^2$ and $A^3$ each independently represents a divalent hydrocarbon group having two to 12 carbon atoms that may contain a branched structure and/or an unsaturated bond; and $A^2$ has preferably not less than two carbon atoms, and preferably not more than ten carbon atoms and more preferably not more than eight carbon atoms. $A^3$ has preferably not less than two carbon atoms, and preferably not more than ten carbon atoms and more preferably not more than eight carbon atoms. Examples of $A^1$ include an ethylene group (—CH$_2$—CH$_2$—), a vinylene group (—CH=CH—), a propylene group (—CH$_2$—CH$_2$—CH$_2$—), an isopropylene group (—CH$_2$—CH(CH$_3$)—), a butylene group (—CH$_2$—CH$_2$—CH$_2$—CH$_2$—), a methylbutylene group (—CH$_2$—CH(CH$_3$)—CH$_2$—CH$_2$—), a dimethylbutylene group (—CH$_2$—CH(CH$_3$)—CH(CH$_3$)—CH$_2$—), an ethyl butylene group (—CH$_2$—CH(C$_2$H$_5$)—CH$_2$—CH$_2$—), a pentylene group (—CH$_2$—CH$_2$—CH$_2$—CH$_2$—CH$_2$—), a hexylene group (—CH$_2$—CH$_2$—CH$_2$—CH$_2$—CH$_2$—CH$_2$—), a heptylene group (—CH$_2$—CH$_2$—CH$_2$—CH$_2$—CH$_2$—CH$_2$—CH$_2$—), and an octylene group (—CH$_2$—CH$_2$—CH$_2$—CH$_2$—CH$_2$—CH$_2$—CH$_2$—CH$_2$—).

B represents a base structure represented by any of the following formulae (II-1) to (II-4) with the formula (II-1) being particularly preferred. It is to be noted that the round bracket in the formulae (II-1) to (II-4) shows each of the binding positions of $A^1$ and the sugar moiety.

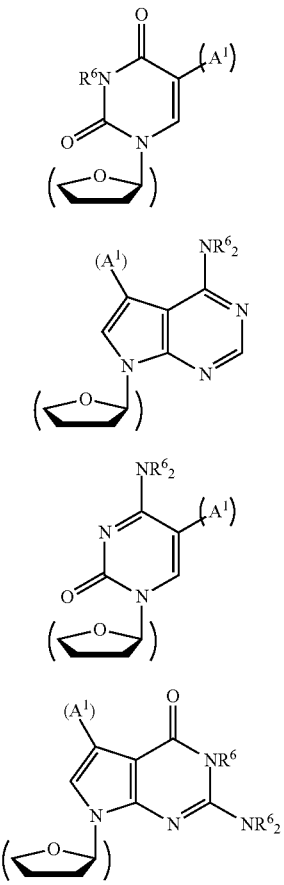

Each $R^6$ independently represents a hydrogen atom, a hydrocarbon group having one to six carbon atoms, or a protective group of an amino group. The protective group is not particularly restricted as long as it is one that is used as a protective group of an amino group. Examples thereof include carbamate-based protective groups such as a tert-butoxycarbonyl group, a benzyloxycarbonyl group, and allyloxycarbonyl; amide-based protective groups such as a propionyl group, an isopropionyl group, a benzoyl group, and an isobutyl group; and sulfonamide-based protective groups such as a p-toluenesulfonyl group, and a 2-nitrobenzenesulfonyl group. In addition, in the case in which $R^6$ is a hydrocarbon group, it has preferably not less than two carbon atoms, and preferably not more than five carbon atoms and more preferably not more than four carbon atoms.

Each X independently represents an imino group ($-NR^5-$), an ether group ($-O-$), or a thioether group ($-S-$); and preferred is an imino group ($-NR^5-$).

Y represents a hydrogen atom or a hydrocarbon group having one to 20 carbon atoms that may contain at least one selected from the group consisting of a nitrogen atom, an oxygen atom, a sulfur atom, and a halogen atom; and Y has preferably not less than two carbon atoms, and preferably not more than 18 carbon atoms and more preferably not more than 15 carbon atoms. It is more preferred that Y be a methyl group ($-CH_3$), or a hydrocarbon group having two to 18 carbon atoms that contains at least one selected from the group consisting of an amino group ($-NH_2$), an imino group ($-NR^5-$), an ether group ($-O-$), a thioether group ($-S-$), an amide group ($-C(=O)-NR^5-$), an ester group ($-C(=O)-O-$), a thioester group ($-C(=O)-S-$), a thioamide group ($-C(=S)-NR^5-$), a thionoester group ($-C(=S)-O-$), a nitro group ($-NO_2$), a cyano group ($-CN$), a phenyl group ($-C_6H_5$), a phenylene group ($-C_6H_4-$), a naphthylene group ($-C_{12}H_8-$), a trifluoromethyl group ($-CF_3$), a fluorine atom ($-F$), and an acyl group that contains a side chain structure of a proteinogenic amino acid. Examples of a specific structure of the hydrocarbon group of Y include ones that are presented by the following formula.

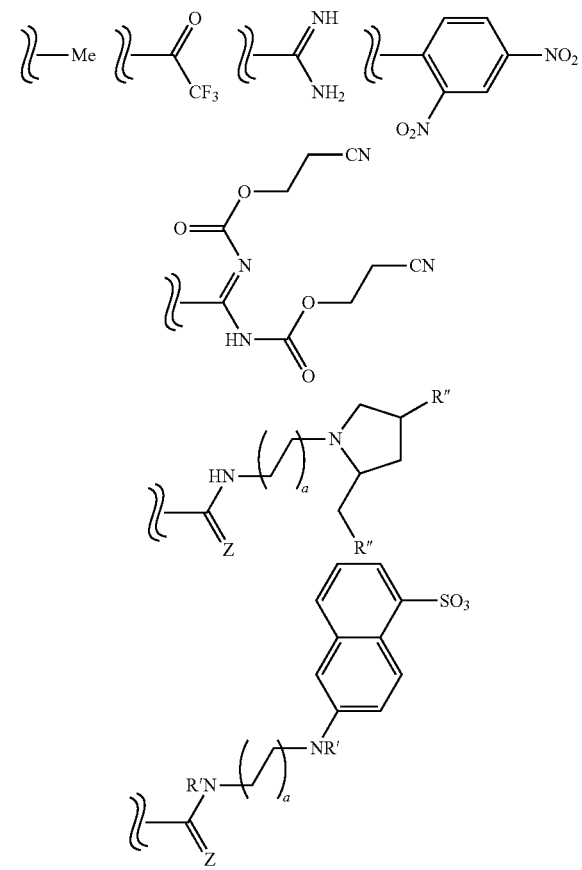

In the above formula, R' represents a hydrogen atom, a methyl group, or an ethyl group; R" represents a hydroxyl group ($-OH$) or a nitro group ($-NO_2$); Z represents an oxygen atom or a sulfur atom; and a represents an integer of 1 to 6.

k represents 1 or 2; and because $R^5$ and Y each may be a hydrogen atom or may be a hydrocarbon group, it means that a nitrogen atom that binds to Y may be any of a primary amino group, a secondary amino group, a tertiary amino group, and a quaternary ammonium group.

A method of producing the nucleoside derivative or the like of the present invention is not particularly restricted; and the nucleoside derivative or the like of the present invention can be produced by combining as appropriate known synthesis methods and can be for example produced in accordance with the following procedure.

(1) A carbon chain that contains an amino group can be introduced to a purine compound by providing a halogenated purine such as 6-chloropurine and a diamine derivative such as ethylenediamine in which a protective group has been introduced to one of the amino groups and promoting a substitution reaction of the halogenated purine by the diamine derivative.

(2) Another carbon chain that contains a nitrogen-containing functional group can be introduced to a purine compound by providing an alkyl halide that contains a nitrogen atom-containing functional group such as an ammonium group and promoting a substitution reaction of the alkyl halide using the imino group of the purine compound.

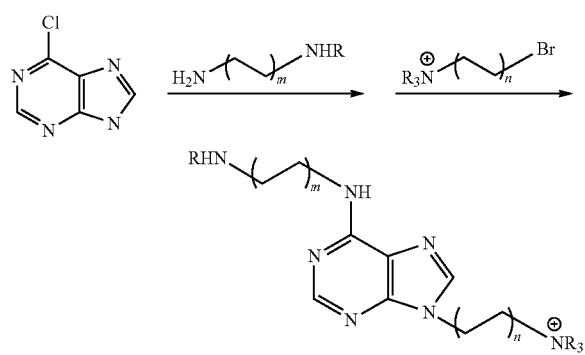

m represents an integer of 1 to 10 and n represents an integer of 1 to 12.

(3) A nucleoside derivative with an acrylic acid structure being introduced to a base moiety can be synthesized by a method described in, for example, Japanese Patent Application Laid-Open Publication No. 2007-056001. By an amidation reaction of this acrylic acid structure with an amino group of a purine compound to which a carbon chain is introduced, the nucleoside derivative or the like of the present invention can be synthesized.

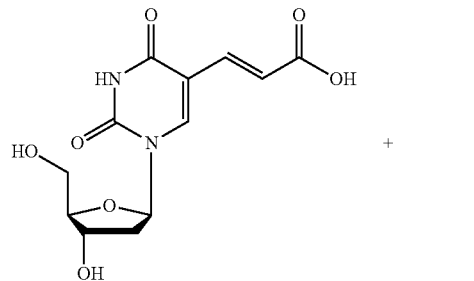

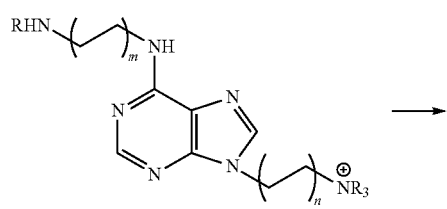

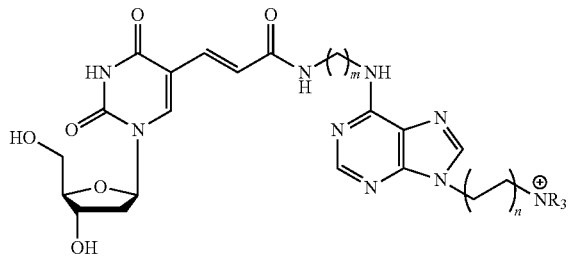

m represents an integer of 1 to 10 and n represents an integer of 1 to 12.

<5'-Phosphate Ester of Nucleoside Derivative or a Salt Thereof>

The nucleoside derivative or the like of the present invention is a compound that is useful for producing a nucleic acid aptamer with excellent binding affinity and excellent target variety; but a nucleotide obtained by phosphorylating the nucleoside derivative of the present invention, that is, a 5'-phosphate ester of nucleoside derivative obtained is also one aspect of the present invention (hereinafter, may be shortened to "the 5'-phosphate ester of the present invention"). It is to be noted that a salt obtained from the 5'-phosphate ester of the present invention shall be included in the scope of the present invention as well.

The 5'-phosphate ester of the present invention can be represented by, for example, any of the following formulae (III-1) to (III-6).

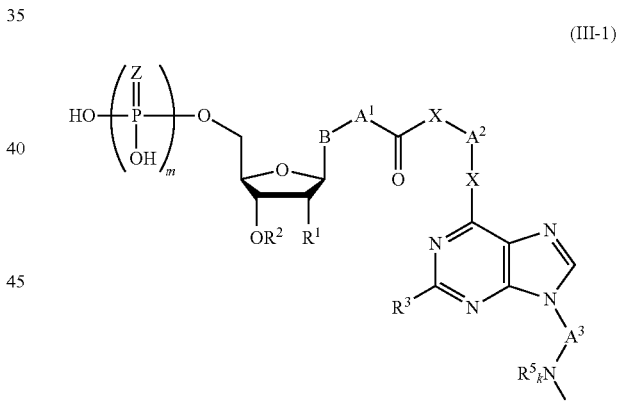

(III-1)

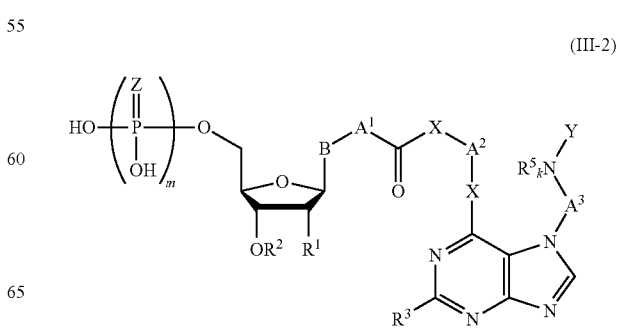

(III-2)

-continued

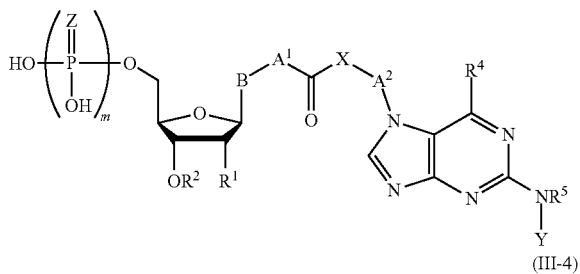
(III-3)

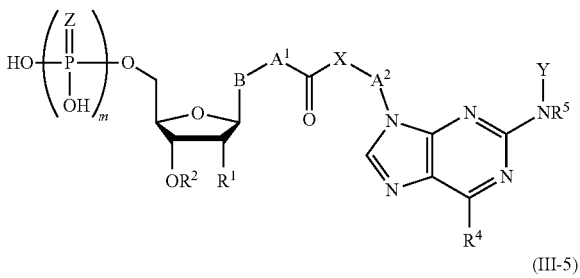
(III-4)

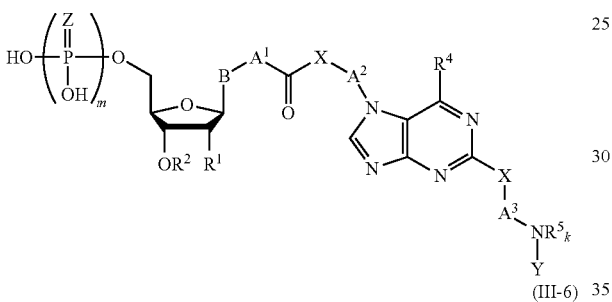
(III-5)

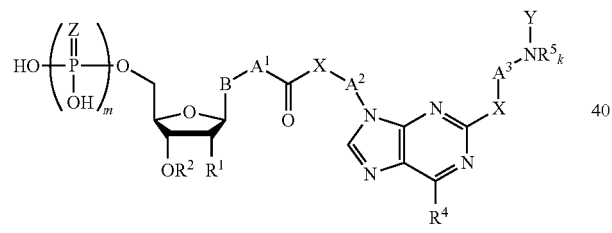
(III-6)

fied polynucleotide, for example, a catalyst and a nucleic acid aptamer. Further, it is possible to link an inhibitor as well.

<3'-Phosphoramidite Product of Nucleoside Derivative or a Salt Thereof>

The nucleoside derivative or the like of the present invention is a compound that is useful for producing a nucleic acid aptamer with excellent binding affinity and excellent target variety; but a 3'-phosphoramidite product obtained by converting the nucleoside derivative of the present invention into amidite for the purpose of using a phosphoramidite method is also one aspect of the present invention (hereinafter, may be shortened to "the phosphoramidite compound of the present invention"). It is to be noted that a salt obtained from the phosphoramidite compound of the present invention shall be included in the scope of the present invention as well.

The phosphoramidite compound of the present invention can be represented by, for example, any of the following formulae (IV-1) to (IV-6).

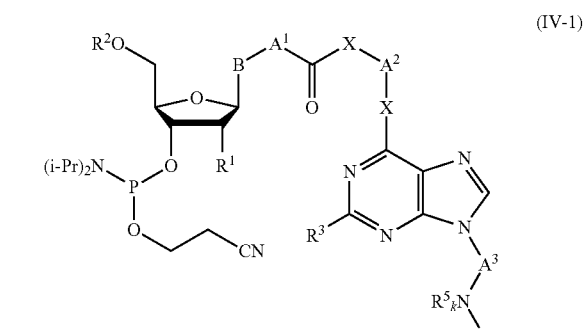
(IV-1)

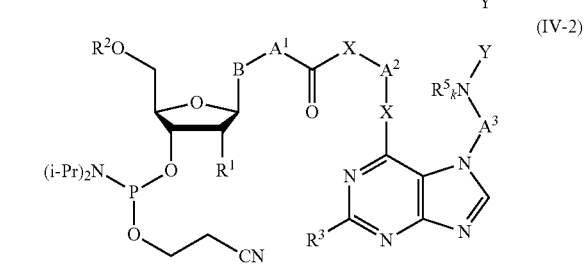
(IV-2)

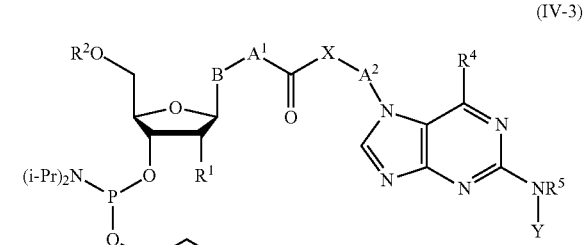
(IV-3)

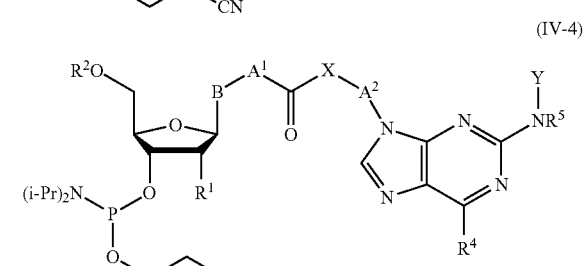
(IV-4)

In the formulae (III-1) to (III-6), m represents an of 1 to 5; each Z independently represents an oxygen atom or a sulfur atom; and $R^1$, $R^2$, $R^3$, $R^4$, $R^5$, $A^1$, $A^2$, $A^3$, B, X, Y, $R^6$, and k respectively represent the same meaning as described in the above-mentioned nucleoside derivative or the like of the present invention.

The 5'-phosphate ester of the present invention may also be in the form of a labeled nucleotide derivative to which a labeling substance such as a fluorescent substance is introduced. A polynucleotide that contains, as a building block, a 5'-phosphate ester to which a labeling substance is bound may be a useful probe or the like. The labeling substance is not particularly restricted as long as it is a known substance that is used as a label for nucleic acids; and examples thereof include fluorescent labeling substances such as fluorescein, Cy5, tetramethyl carboxyrhodamine, or pyrene. In addition, the labeling substance can be introduced to, for example, an amino group of the 5'-phosphate ester. It is to be noted that, besides the fluorescent label, various functional substances can also be introduced to the 5'-phosphate ester of the present invention, thereby synthesizing a functional modi-

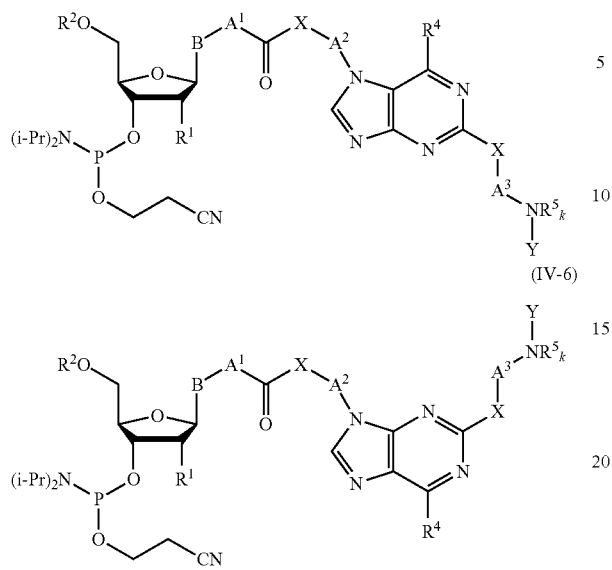

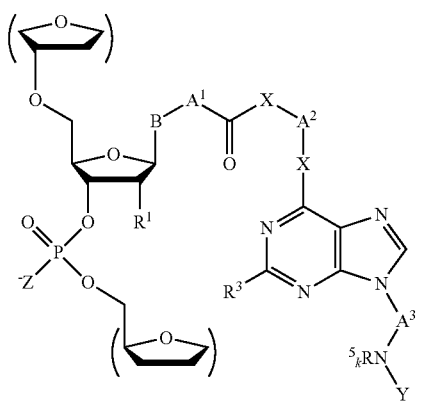

In the formulae (IV-1) to (IV-6), $R^2$ represents a hydrogen atom or a protective group of a hydroxyl group in the same way as described in the nucleoside derivative or the like of the present invention; and it is preferred to be a di(p-methoxyphenyl)phenylmethyl group as a protective group of a hydroxyl group. In addition, $R^1$, $R^3$, $R^4$, $R^5$, $A^1$, $A^2$, $A^3$, B, X, Y, $R^6$, and k respectively represent the same meaning as described in the above-mentioned nucleoside derivative or the like of the present invention.

Like the 5'-phosphate ester of the present invention, the phosphoramidite compound of the present invention may also be in the form of a labeled nucleotide derivative to which a labeling substance such as a fluorescent substance is introduced. It is to be noted that specific labeling substances are the same ones as described in the 5'-phosphate ester of the present invention.

<Method of Producing a Substrate Solution for Polynucleotide Synthesis, a Reagent for Polynucleotide Synthesis, and a Polynucleotide>

The 5'-phosphate ester of the present invention and a salt thereof, the phosphoramidite compound of the present invention and a salt thereof, and a labeled nucleotide derivative obtained by introducing a labeling substance thereto are substrates for synthesis that are useful for synthesizing a polynucleotide; and a substrate solution for polynucleotide synthesis that contains at least one of those, a reagent for polynucleotide synthesis that contains this substrate solution for polynucleotide synthesis, and, in addition, a method of producing a polynucleotide using them as substrates for synthesis are also aspects of the present invention.

<Polynucleotide>

The nucleoside derivative or the like of the present invention is a compound that is useful for producing a nucleic acid aptamer with excellent binding affinity and excellent target variety; and a nucleic acid that is produced by using the nucleoside derivative or the like of the present invention, that is, a polynucleotide that contains, as a building block, the 5'-phosphate ester of the present invention and/or a phosphorothioated product thereof are also aspects of the present invention (hereinafter, may be shortened to "the polynucleotide of the present invention"). It is to be noted that a labeled polynucleotide that contains, as a building block, a 5'-phosphate ester to which a labeling substance such as a fluorescent substance is introduced shall be also included in the scope of the present invention.

Examples of the polynucleotide of the present invention include one that at least contains a nucleotide structure that can be presented by any of the following formulae (V-1) to (V-6).

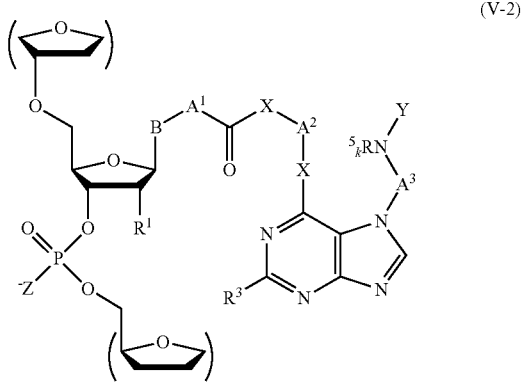

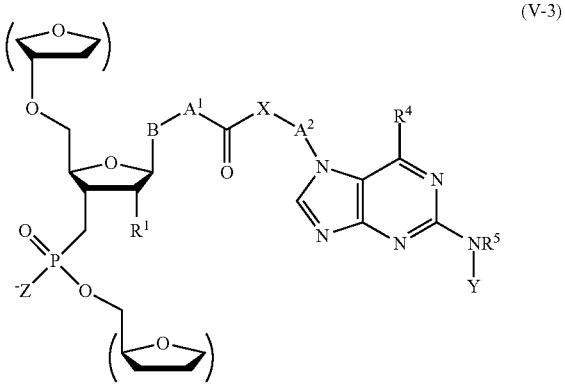

-continued

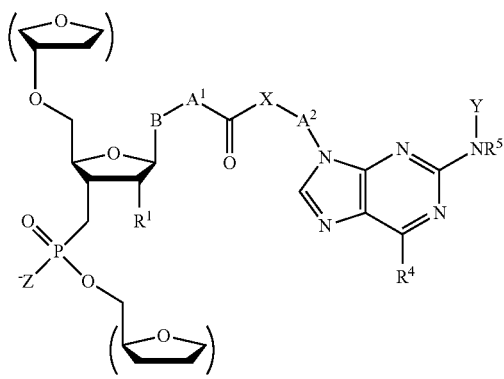

(V-4)

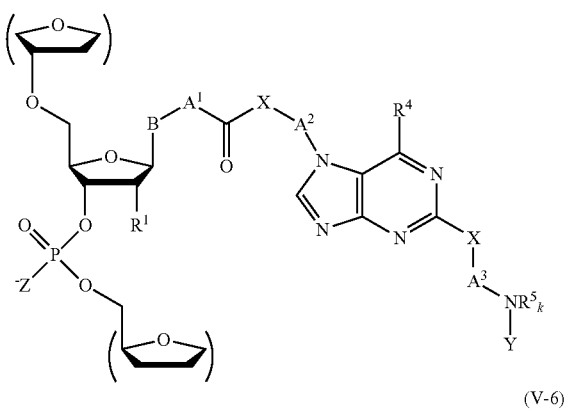

(V-5)

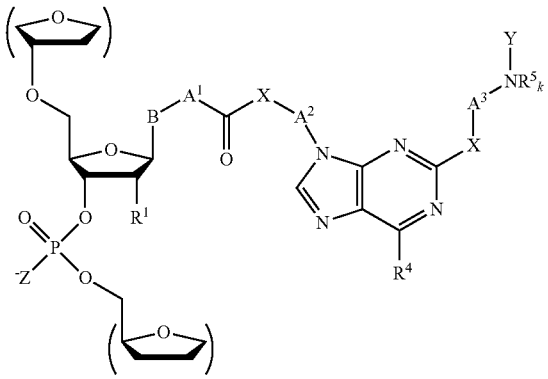

(V-6)

In the formulae (V-1) to (V-6), each Z independently represents an oxygen atom or a sulfur atom; and $R^1$, $R^2$, $R^3$, $R^4$, $R^5$, $A^1$, $A^2$, $A^3$, B, X, Y, $R^6$, and k respectively represent the same meaning as described in the above-mentioned nucleoside derivative or the like of the present invention. In addition, the round bracket in the formulae (V-1) to (V-6) shows each position at which the neighboring nucleotide structure binds. Further, "a phosphorothioated product thereof" shall refer to one with Z being a sulfur atom.

The polynucleotide of the present invention is not particularly restricted as long as it contains the 5'-phosphate ester of the present invention and/or a phosphorothioated product thereof as a building block; and preferred is one that contains the 5'-phosphate ester of the present invention at the 5' end. In addition, the polynucleotide of the present invention has usually not less than 10 nucleotides, preferably not less than 15 nucleotides, usually not more than 200 nucleotides, preferably not more than 100 nucleotides, and more preferably not more than 70 nucleotides.

A method of producing the polynucleotide of the present invention is not particularly restricted; and the polynucleotide of the present invention can for example be produced as appropriate by a known synthesis method using the 5'-phosphate ester of the present invention, phosphoramidite compound, or the like as a raw material. In the case of producing DNA, for example, the polynucleotide of the present invention can be produced by synthesizing a polynucleotide using a DNA synthesizer by a phosphoramidite method or a solid phase phosphoramidite method, which is commonly used, and purifying the resulting polynucleotide using anion exchange column chromatography or the like.

Further, the structure of the phosphorothioated compound in the polynucleotide of the present invention can be formed by employing as appropriate a known method of introducing a phosphorothioate group.

The polynucleotide of the present invention may be a polynucleotide to which a labeling substance such as a fluorescent substance is introduced and can also be converted to a single strand to be used for a probe in a microarray.

Further, use of the polynucleotide of the present invention is not particularly restricted, the polynucleotide of the present invention can be used as appropriate in known applications such as catalysts or nucleic acid aptamers and is preferably used as nucleic acid aptamers. For example, the polynucleotide of the present invention can be used as nucleic acid medicine which regulates gene expression such as antisense molecules or antigene molecules. The polynucleotide of the present invention can produce excellent plasma membrane permeability, excellent gene suppression effects, mitigation of adverse effects, and resistance to nuclease; and can be used as effective nucleic acid medicine.

<Method of Selecting a Polynucleotide Library and a Nucleic Acid Aptamer>

The polynucleotide of the present invention can be used in a polynucleotide library for SELEX method or the like; yet the polynucleotide library that contains the polynucleotide of the present invention (hereinafter, may be shortened to "the polynucleotide library of the present invention"), and the method of selecting a nucleic acid aptamer comprising the step of selecting a target substance-binding polynucleotide using this polynucleotide library (hereinafter, may be shortened to "the selection method of the present invention") are also aspects of the present invention.

As for the polynucleotide library of the present invention, as long as the polynucleotide of the present invention is included and there is no particular restriction; but it is for example preferred to contain plural kinds of polynucleotides that contain a random sequence synthesized by using 5'-phosphate ester or the like of the present invention.

As for the selection method of the present invention, the step of selecting a target substance-binding polynucleotide using a polynucleotide library is included and there is no particular restriction; and the selection method can for example include the steps that are carried out in SELEX method. SELEX method is a method of obtaining an aptamer with a target substance-binding property, which method usually comprises repeating a series of the steps: immobilizing a target substance onto a carrier such as a bead, adding a polynucleotide library thereto, collecting a nucleic acid that binds to the target substance, amplifying the collected polynucleotide, and adding again the amplified polynucleotide to the target substance; concentrating a polynucleotide with a high specificity for and affinity to the target substance; and determining its nucleotide sequence.

By the selection method of the present invention, a variety of practically-usable functional nucleic acids such as nucleic acid aptamers for various biological-related substances or the like and ribozymes that catalyze a specific reaction can be screened. That is, aptamers and ribozymes with physiological activities can be obtained by synthesizing plural random polynucleotides and selecting a specific polynucleotide from among them using an enzyme activity or the like as an index.

Examples of the biological-related substance include proteins such as enzymes, antibodies, and cytokines. Specific examples include vesicular endothelial growth factor (VEGF); and a nucleic acid aptamer that contains a residue (nucleotide residue) of the modified nucleic acid of the following is useful as a VEGF binding agent.

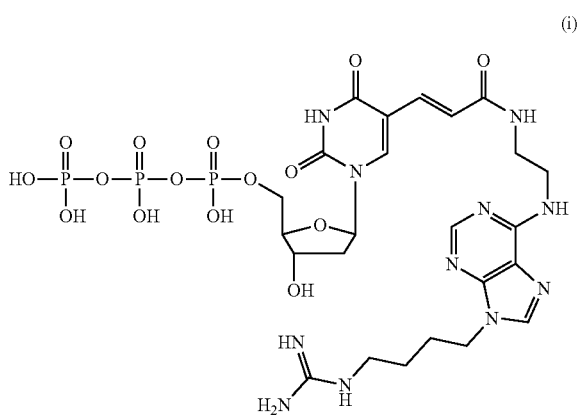 [SMILES: N=C(N)NCCCCn1cnc2c(NCCNC(=O)/C=C/c3cn(C4CC(O)C(COP(=O)(O)OP(=O)(O)OP(=O)(O)O)O4)c(=O)[nH]c3=O)ncnc21]

(i)

A nucleic acid aptamer that contains a residue of the modified nucleic acid of the (i) refers to a nucleic acid aptamer that contains a residue of the modified nucleic acid of (i) together with one or more kinds of four kinds of natural bases of adenine (A), thymine (T), guanine (G), and cytosine (C); and it is preferred to be a nucleic acid aptamer that contains the residue of the modified nucleic acid of (i) instead of thymine (T) because the modified nucleic acid of (i) is a derivative of thymidine 5'-triphosphate (dTTP). That is, preferred is a nucleic acid aptamer that contains the residue of the modified nucleic acid of (i) together with one or more kinds of three kinds of natural bases of adenine (A), guanine (G), and cytosine (C). It is preferred that a ratio of residues of the modified nucleic acid of (i) in the full length of the nucleic acid aptamer be 10 to 50%.

A nucleic acid aptamer that can be used as a VEGF binding agent may contain the residue of other modified nucleic acid in addition to the residue of the modified nucleic acid of (i).

Such a nucleic acid aptamer is obtained by using a DNA synthesizer or the like. For example, a nucleic acid aptamer with a sequence of interest can be synthesized by using adenine (A), guanine (G), cytosine (C), and a 3'-phosphoramidite of the modified nucleic acid of (i) in a DNA synthesizer.

As for a specific aspect of nucleic acid aptamer that can be used as a VEGF binding agent, there is no particular restriction as long as it has the VEGF binding capability. Examples thereof include nucleic acid aptamers in which the sequence of the nucleic acid aptamer includes the sequence of nucleotides 21 to 50 in any of SEQ ID NOs: 6 to 31 and 33 to 40 or the sequence of the nucleotides 21 to 49 in SEQ ID NO: 32. In these sequences, T refers to the modified nucleic acid residue of the above (i).

As long as the capability of binding to VEGF is maintained, one to several nucleotides, for example, one, two, or three nucleotides in those sequences may be substituted, deleted, inserted, or the like. In addition, as long as the VEGF binding capability is maintained, any length of any sequence may be added to the 5' side and/or the 3' side.

As for the VEGF binding capability, it is preferred to exhibit an affinity with a Kd (dissociation constant) for human VEGF of not more than 10 nM.

By providing a library of nucleic acid aptamers containing the residue of the modified nucleic acid of (i) together with one or more kinds of four kinds of natural bases of adenine (A), thymine (T), guanine (G), and cytosine (C), bringing the library into contact with VEGF, selecting a nucleic acid aptamer that binds to VEGF, and repeating amplification, the VEGF binding agent of the present invention can also be obtained by selection from the library of nucleic acid aptamers.

The VEGF binding agent of the present invention can be used as a molecular probe for VEGF detection. For example, a nucleic acid aptamer can be labeled with a fluorescent dye or the like to trace kinetics of VEGF or the like in the body. VEGF is known to be highly expressed in cancers, abnormal angiogenesis such as diabetic retinopathy, inflammatory diseases such as articular rheumatism, and the like; and therefore the VEGF binding agent of the present invention can be used as a diagnosis reagent for these diseases.

In addition, because tumor tissues have advanced angiogenesis and VEGFs accumulate in tumor tissues, the nucleic acid aptamer of the present invention can be used for DDS (drug delivery system) for an anti-cancer agent. An anti-cancer agent can be efficiently delivered to tumor tissues by coupling an active component of the anti-cancer agent with an aptamer and administering the resultant.

For example, by linking the nucleic acid aptamer of the present invention with an nucleic acid aptamer that is involved in binding with camptothecins disclosed in Japanese Patent Application Laid-Open Publication No. 2013-40118 and coupling camptothecins therewith, a pharmaceutical for allowing camptothecins to reach tumor tissues can be prepared.

EXAMPLES

By way of examples and comparative examples, the present invention will be more specifically described below; but modifications can be made as appropriate without departing from the scope of the present invention. Therefore, the scope of the present invention should not be interpreted in a limited fashion by the specific examples shown below.

Synthesis of N-Boc-ethylenediamine (Compound)

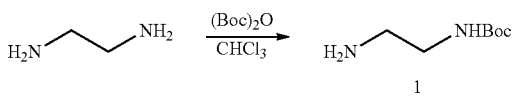

1

Ethylenediamine (4 mL, 60 mmol) was added to $CHCl_3$ (130 mL) and stirred; and di-tert-butyl dicarbonate (2 g, 9.16 mmol) that had been dissolved in $CHCl_3$ (20 mL) was added dropwise thereto under Ar atmosphere. The resulting mixture was stirred for 18 hours and checked with TLC, and thereafter subjected to distillation under reduced pressure. The residue after filtration was filtered with CHCl$_3$ and the filtrate was purified using column chromatography (10% MeOH/3% TEA/CHCl$_3$). This resultant was dried under reduced pressure, thereby obtaining compound 1. The absolute yield was 1465 mg and the percentage yield was 99.9%.

$^1$HNMR (400 MHz, CDCl$_3$) δ 3.18 (2H, q) 2.80 (2H, t) 1.45 (9H, s)

ESI-MS (positive ion mode) m/z, found=161.4, calculated for [(M+H)$^+$]=161.1.

Synthesis of (4-Bromobutyl)trimethylammonium bromide (Compound 2)

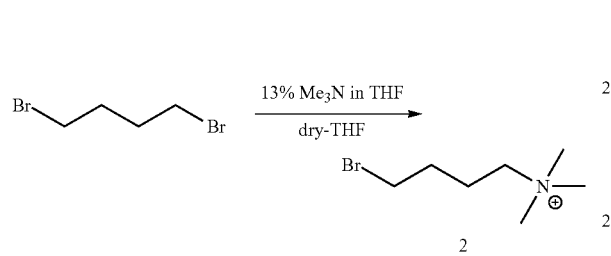

To 13% trimethylamine in THF (2 mL), 1,4-dibromobutane (0.6 mL, 5.1 mmol) that had been dissolved in dry-THF (0.6 mL) was added and stirred under Ar atmosphere for 24 hours. The resulting mixture was thereafter filtered with THF to obtain the residue after filtration which was used as compound 2. The absolute yield was 1091 mg and the percentage yield was 80.0%.

$^1$HNMR (400 MHz, CD$_3$OD) δ 3.81 (2H, t) 3.53 (2H, t) 3.49 (9H, s) 2.01 (4H, m)

ESI-MS (positive ion mode) m/z, found=194.0, calculated for [(M)$^+$]=194.1.

Synthesis of Compound 3

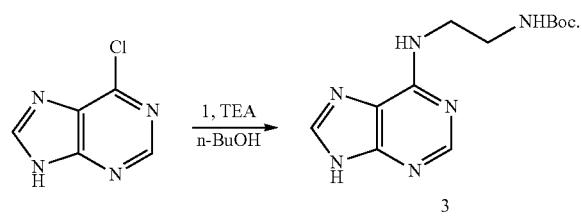

6-Chloropurine (850 mg, 5.5 mmol) was suspended in n-BuOH (6 mL); and TEA (7.7 mL) was added thereto and stirred. The compound 1 (485 mg, 3.03 mmol) that had been dissolved in n-BuOH (4 mL) was added thereto and subjected to reflux. Two hours later, the compound 1 (485 mg, 3.03 mmpl) that had been dissolved in n-BuOH (3 mL) was added to the resultant and subjected to reflux for two hours. After completion of the reaction, the resultant was subjected to distillation under reduced pressure and filtered with CHCl$_3$ to obtain the residue after filtration as compound 3. The absolute yield was 1342 mg and the percentage yield was 88%.

$^1$HNMR (400 MHz, CD$_3$OD) δ 8.23 (1H, s) 8.06 (1H, s) 3.70 (2H, m) 3.42 (2H, t) 1.39 (9H, s)

ESI-MS (positive ion mode) m/z, found=279.5, calculated for [(M+H)$^+$]=279.2

Synthesis of Compound 4

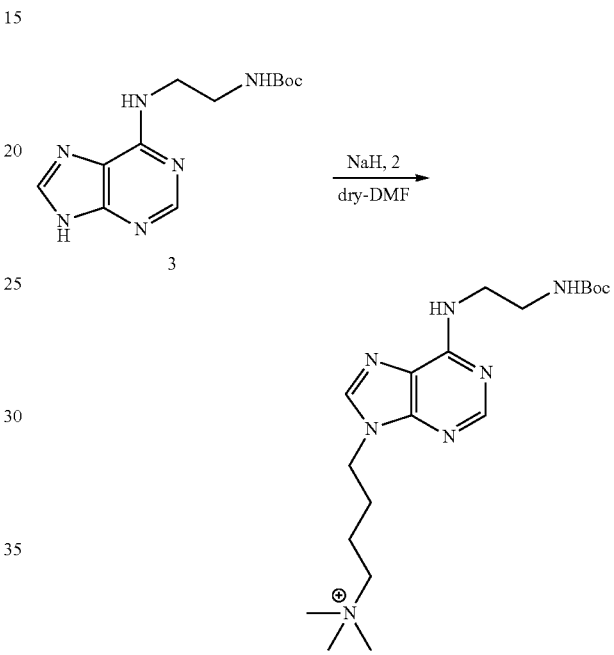

The compound 3 (1086 mg, 3.9 mmol) was dissolved in dry-DMF (10 mL) and stirred, while cooled in ice, for 30 minutes. Sodium hydride (60% in oil) (214 mg, 5.35 mmol) was then quickly added thereto and stirred at 0° C. for 1.5 hours. The compound 2 (1395 mg, 4.67 mmol) that had been dissolved in dry-DMF (10 mL) was added thereto and stirred under Ar atmosphere at room temperature. Five hours later, water was added thereto and subjected to distillation under reduced pressure. The residue was dissolved in MeOH and filtered; and the filtrate was subjected to distillation under reduced pressure. This was purified by reversed phase column chromatography (100% H$_2$O→5% MeOH/H$_2$O→10% MeOH/H$_2$O), thereby obtaining compound 4. The absolute yield was 1283 mg and the percentage yield was 70%.

$^1$HNMR (400 MHz, CD$_3$OD) δ 8.27 (1H, s) 8.12 (1H, s) 4.32 (2H, t) 3.69 (2H, m) 3.41 (2H, t) 3.12 (11H, s) 1.95 (2H, m) 1.84 (2H, m) 1.40 (9H, s)

ESI-MS (positive ion mode) m/z, found=392.3, calculated for [(M)$^+$]=392.3.

Synthesis of Compound 5

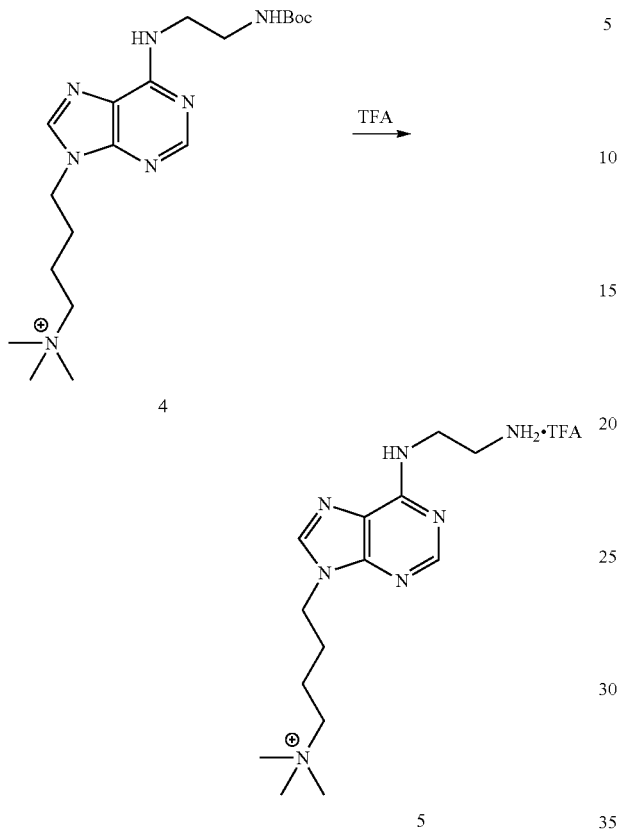

Trifluoroacetate (14 mL) was added to the compound 4 (467 mg, 0.99 mmol) and stirred for one hour. The resulting mixture was subjected to distillation under reduced pressure and filtered with ether to quantitatively obtain the residue after filtration as compound 5. The theoretical yield is 0.99 mmol.

$^1$HNMR (400 MHz, CD$_3$OD) δ 8.37 (1H, s) 8.22 (1H, s) 4.34 (2H, t) 3.95 (2H, m) 3.42 (2H, t) 3.12 (11H, s) 1.96 (2H, m) 1.85 (2H, m)

ESI-MS (positive ion mode) m/z, found=292.4, calculated for [(M)$^+$]=292.2.

Example 1

Synthesis of Compound 6

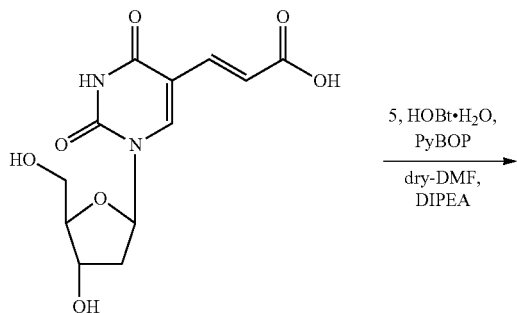

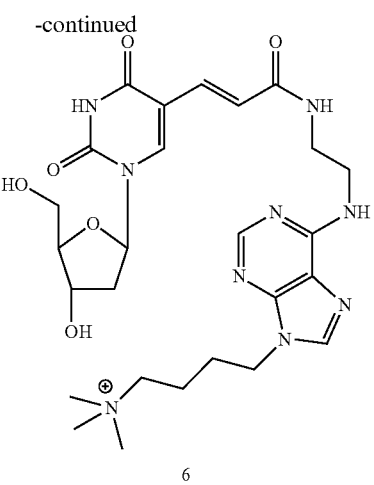

HOBt.H2O (137 mg, 891 μmol) and PyBOP (464 mg, 891 μmol) were added to (E)-5-(2-carboxyvinyl)-2'-deoxyuridine (204 mg, 686 μmol) and dissolved in dry-DMF (8 mL). DIPEA (1.2 mL, 6.86 mmol) was added thereto and stirred, immediately followed by addition of the compound 5 (0.99 mmol) that had been dissolved in dry-DMF (2 mL) under Ar atmosphere. After stirred for two hours, the resulting mixture was subjected to distillation under reduced pressure and purified by reversed phase column chromatography (100% H2O→3% MeOH/H2O→5%→8%→10%→12%→15%), thereby obtaining compound 6. The absolute yield was 330 mg and the percentage yield was 76%.

$^1$HNMR (400 MHz, D2O) δ 8.01 (1H, s) 8.27 (1H, s) 7.93 (1H, s) 7.90 (1H, s) 6.78 (1H, d) 6.54 (1H, d) 6.06 (1H, t) 4.28 (1H, q) 4.05 (2H, t) 3.88 (1H, q) 3.69 (1H, q) 3.59 (1H, q) 3.41 (2H, q) 3.13 (2H, t) 2.88 (11H, s) 2.30-2.14 (2H, m) 1.69 (2H, m) 1.60 (2H, m)

ESI-MS (positive ion mode) m/z, found=572.5, calculated for [(M)$^+$]=572.3

Example 2

Synthesis of Compound 7

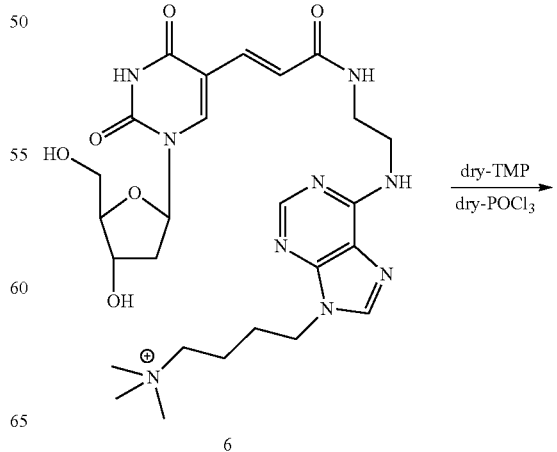

27

-continued

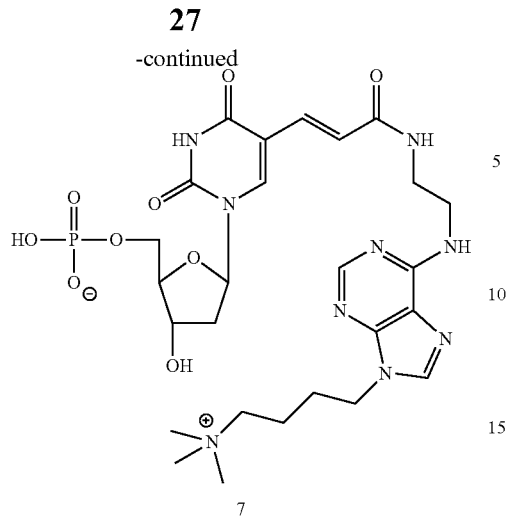

7

28

-continued

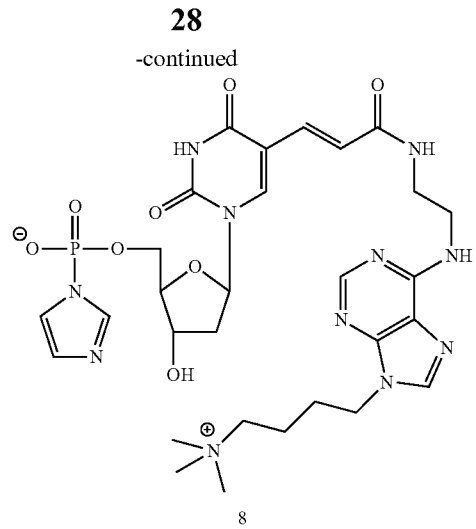

8

The compound 6 (108 mg, 166 μmol) that had been subjected to vacuum drying was subjected to azeotropy with dry-DMF (5 mL) twice and with dry-MeCN (2 mL) twice; and the resultant was dissolved in dry-TMP (50 mL), added with phosphoryl chloride (310 μL, 3.31 mmol) while cooled on ice, and stirred for 10 hours. Thereafter, 30 mL of cold water was added to the resultant and stirred for 10 minutes; and TEA (1.4 mL, 9.93 mmol) was added thereto and stirred for another 10 minutes for quenching. The resultant was subjected to distillation under reduced pressure and then crystallized with MeCN and ether to obtain the residue after filtration. The residue was dissolved in a small amount of water and purified by anion exchange column chromatography, thereby obtaining compound 7. The absolute yield was 53.1 μmol and the percentage yield was 32%.

ESI-MS (positive ion mode) m/z, found=652.3, calculated for $[(M)^+]=652.3$.

ESI-MS (negative ion mode) m/z, found=649.7, calculated for $[(M-2H)-]=650.3$.

Synthesis of Compound 8

The compound 7 (53.1 μmol) that had been subjected to freeze drying was subjected to azeotropy with dry-DMF (2 mL) twice and suspended in dry-DMF (1.2 mL); and dry-TEA (49 μL, 350 μmol), imidazole (14 mg, 212 μmol), triphenylphosphine (22 mg, 85 μmol), and 2,2'-dithiodipyridine (19 mg, 85 μmol) were added thereto and stirred. Nine hours later, 16 mL of dry-Acetone in which sodium perchlorate (67 mg, 531 μmol) had been dissolved was added in a reaction solution and left to stand at 4° C. for 30 minutes. The precipitate was subjected to decantation with dry-ether (16 mL) six times. This precipitate was subjected to vacuum drying, thereby obtaining compound 8 as a crude product. The theoretical yield is 53.1 μmol.

ESI-MS (positive ion mode) m/z, found=702.1, calculated for $[(M)^+]=702.3$.

ESI-MS (negative ion mode) m/z, found=699.5, calculated for $[(M-2H)-]=700.3$.

Example 3

Synthesis of Compound 9 (dU$^{ra}$TP)

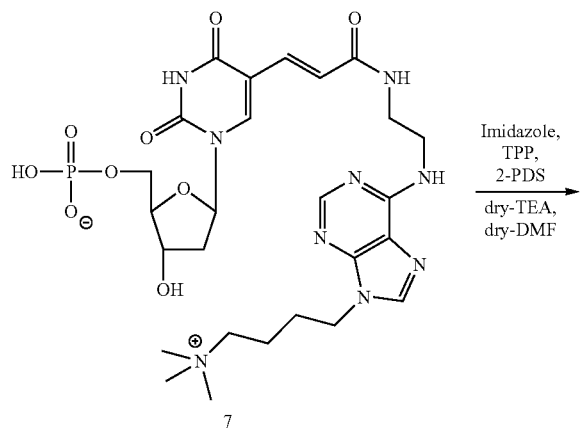

7

Imidazole, TPP, 2-PDS
———————→
dry-TEA, dry-DMF

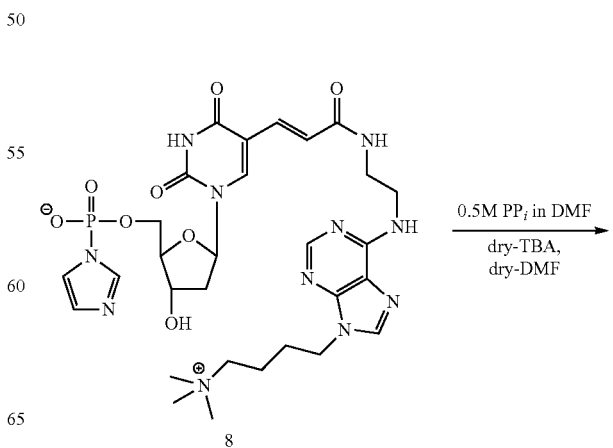

8

0.5M PP$_i$ in DMF
———————→
dry-TBA, dry-DMF

-continued

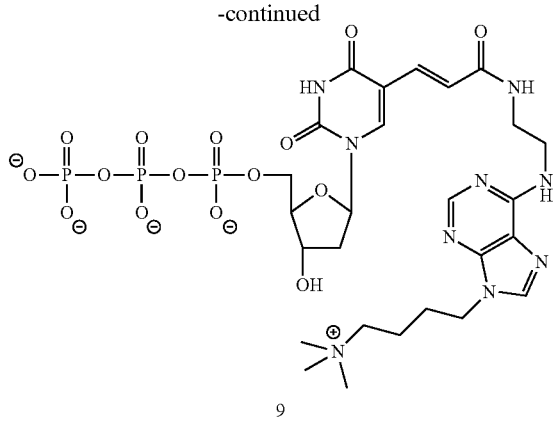

9

The compound 8 (53.1 μmol, 38 mg) that had been subjected to vacuum drying was subjected to azeotropy with dry-DMF (2 mL) twice and suspended in dry-DMF (1 mL); and dry-n-tributylamine (75 μL, 314 μmol) and 0.5 M n-tributylamine pyrophosphate in DMF (0.8 mL, 404 μmol) were added thereto and stirred. Twelve hours later, the resultant was quenched with 1 M TEAB buffer (5 mL) and subjected to distillation under reduced pressure. This was added with water and separated using ether three times. The water layer was purified using anion exchange column chromatography and reversed phase HPLC and subjected to freeze drying, thereby obtaining compound 9 (dUTP). The absolute yield was 7.74 μmol and the percentage yield was 14.6% (from the compound 7).

ESI-MS (negative ion mode) m/z, found=809.5, calculated for [(M−3H)−]=809.6.

Synthesis of Compound 10

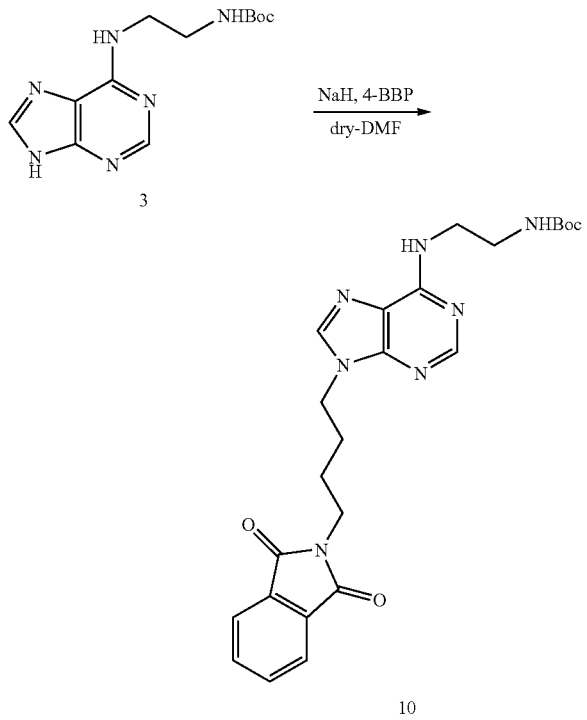

The compound 3 (666 mg, 2.4 mmol) that had been subjected to vacuum drying was suspended with dry-DMF (5 mL) and stirred while cooled on ice for 30 minutes. Sodium hydride (60% in oil) (180 mg, 4.5 mmol) was then quickly added thereto and stirred under Ar atmosphere while cooled on ice for 1.5 hours. N-(4-Bromobutyl)phthalimide (886 mg, 3.14 mmol) that has been subjected to vacuum drying was added thereto and, four hours later, subjected to distillation under reduced pressure. This was filtered with $CHCl_3$ and the filtrate was purified by reversed phase column chromatography (0%→0.5%→1%→2%→3% MeOH/$CHCl_3$), thereby obtaining compound 10. The absolute yield was 847 mg and the percentage yield was 73.8%.

$^1$HNMR (400 MHz, $CDCl_3$) δ 8.34 (1H, s) 7.84 (2H, m) 7.76 (1H, s) 7.72 (2H, m) 4.25 (2H, t) 3.83-3.71 (4H, m) 3.43 (2H, q) 1.94 (2H, m) 1.73 (2H, m) 1.41 (9H, s)

ESI-MS (positive ion mode) m/z, found=480.2, calculated for [(M+H)+]=480.2.

Synthesis of Compound 11

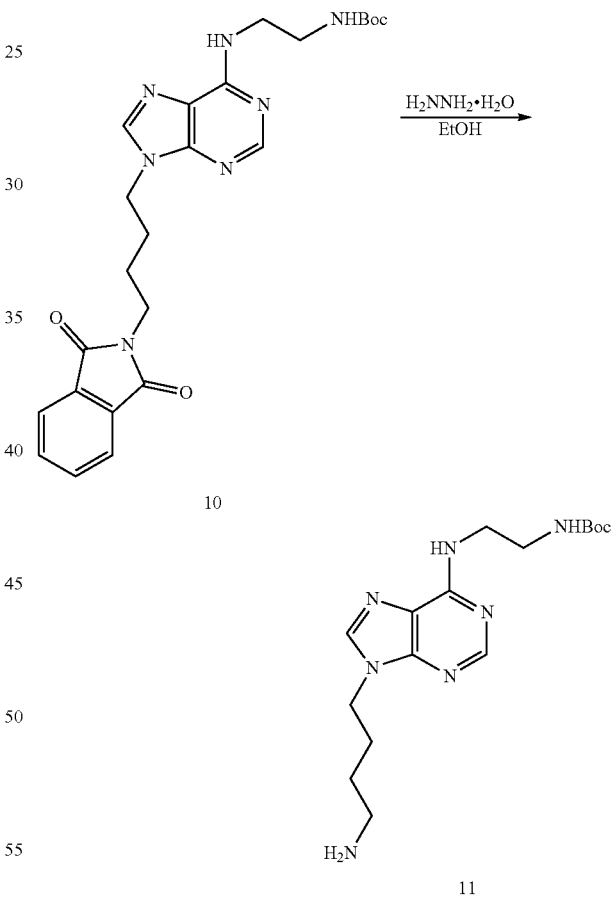

The compound 10 (847 mg, 1.77 mmol) was suspended in EtOH (19 mL); and hydrazine monohydrate (429 μL, 8.83 mmol) was added thereto and stirred. Four hours later, the resultant was filtered with cold EtOH; and the filtrate was subjected to distillation under reduced pressure, thereby quantitatively obtaining compound 11 which was a crude product. The theoretical yield was 1.77 mmol.

ESI-MS (positive ion mode) m/z, found=350.3, calculated for [(M+H)+]=350.2.

Synthesis of Compound 12

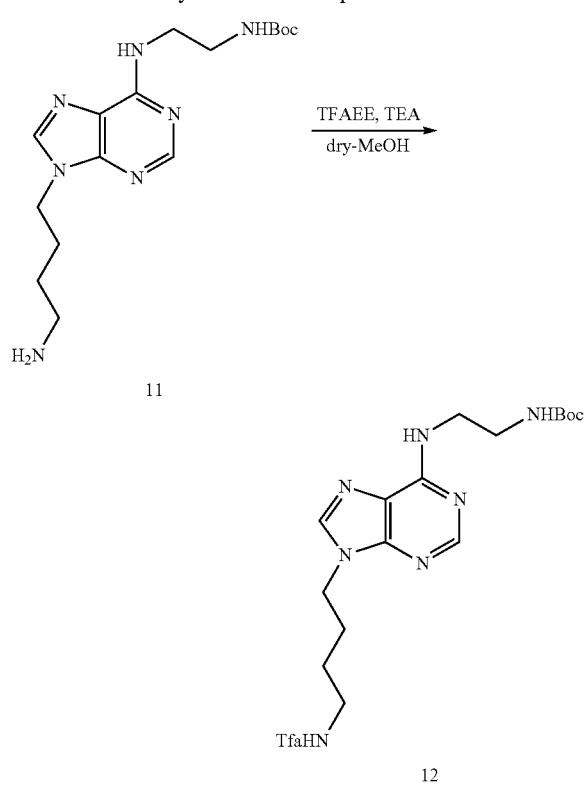

The compound 11 (1.77 mmol) was dissolved in dry-MeOH (9 mL); and TEA (2.5 mL, 9.1 mmol) and ethyl trifluoroacetate (1.1 mL, 9.1 mmol) were added thereto and stirred under Ar atmosphere. Two hours later, the resultant was subjected to distillation under reduced pressure and purified by column chromatography (0%→0.5%→1%→1.5%→2%→2.5%→3% MeOH/CHCl$_3$), thereby obtaining compound 12. The absolute yield was 740 mg and the percentage yield was 91.2% (from the compound 10).

$^1$HNMR (400 MHz, CDCl$_3$) δ 8.35 (1H, s) 7.75 (1H, s) 4.25 (2H, t) 3.81 (2H, m) 3.52-3.41 (4H, m) 1.98 (2H, m) 1.64 (2H, m) 1.42 (9H, s)

ESI-MS (positive ion mode) m/z, found=446.1, calculated for [(M+H)$^+$]=446.2.

Synthesis of Compound 13

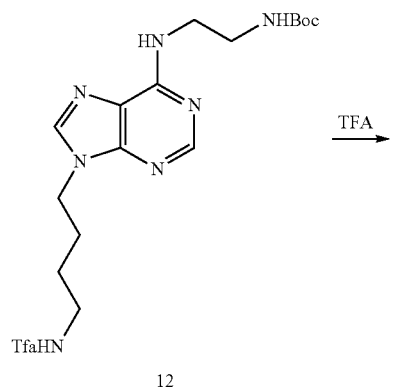

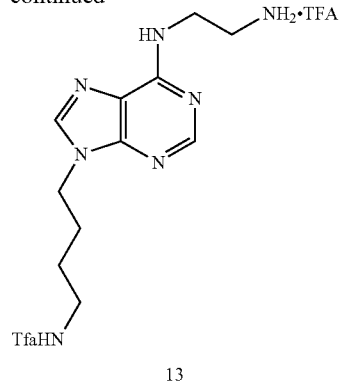

To the compound 12 (740 mg, 1.66 mmol), trifluoroacetate (10 mL) was added and stirred. One hour later, the mixture was subjected to distillation under reduced pressure and vacuum drying. Thereafter, the resultant was separated with water and ether; and the water layer was subjected to distillation under reduced pressure, thereby quantitatively obtaining compound 13 as a crude product. The theoretical yield was 1.66 mmol.

$^1$HNMR (400 MHz, CD$_3$OD) δ 8.34 (1H, s) 8.30 (1H, s) 4.34 (2H, t) 4.03 (2H, m) 3.25-3.18 (4H, m) 1.93 (2H, m) 1.58 (2H, m)

ESI-MS (positive ion mode) m/z, found=346.2, calculated for [(M+H)$^+$]=346.2.

Example 4

Synthesis of Compound 14

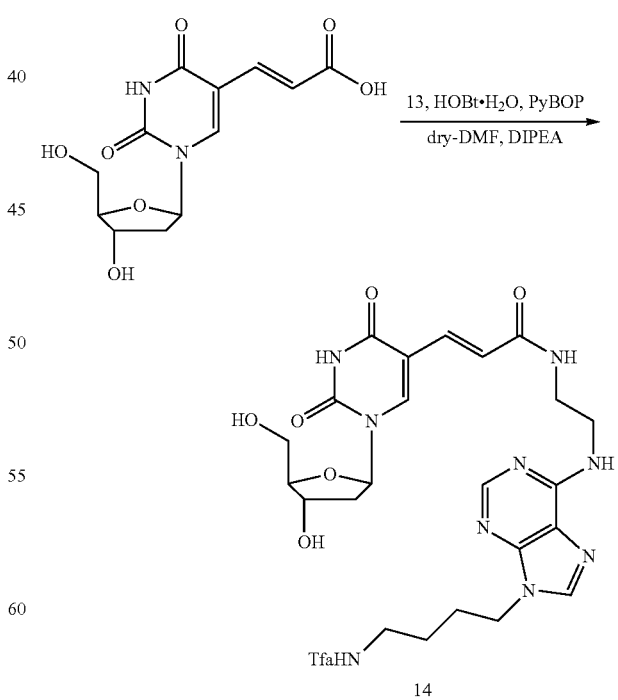

(E)-5-(2-carboxyvinyl)-2'-deoxyuridine (267 mg, 0.91 mmol) was dissolved in dry-DMF (10 mL); and HOBt.H$_2$O (182 mg, 1.18 mmol), PyBOP (616 mg, 1.18 mmol), and DIPEA (1.6 mL, 9.1 mmol) were thereto and stirred. The compound 13 (1.66 mmol) that has been dissolved in dry-DMF (10 mL) added thereto under Ar atmosphere. Two hours later, the resultant was subjected to distillation under reduced pressure and filtered with MeOH, thereby obtaining the residue after filtration as compound 14. The absolute yield was 558 mg and the percentage yield was 98.1%.

$^1$HNMR (400 MHz, CD$_3$OD) δ 8.38 (1H, s) 8.27 (1H, s) 8.08 (1H, s) 7.20 (1H, d) 7.04 (1H, d) 6.27 (1H, t) 4.42 (1H, q) 4.26 (2H, t) 3.95 (1H, q) 3.85 (1H, q) 3.76 (1H, q) 3.57 (2H, t) 3.52 (2H, t) 3.38 (2H, t) 2.29 (2H, m) 1.86 (2H, m) 1.67 (2H, m)

ESI-MS (positive ion mode) m/z, found=624.1, calculated for [(M+H)$^+$]=624.2.

Example 5

Synthesis of Compound 15

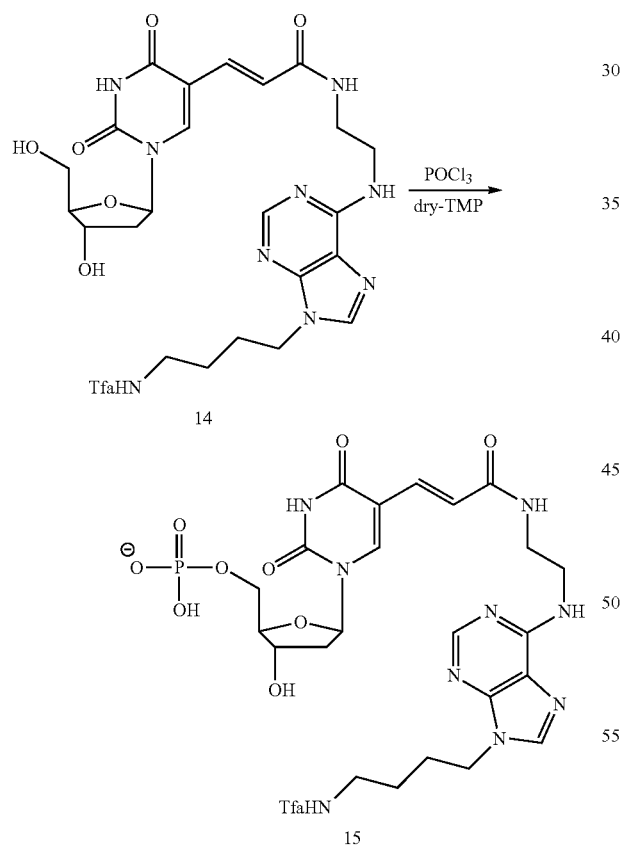

The compound 14 (250 mg, 0.4 mmol) that had been subjected to vacuum drying was suspended in 10 mL of dry-TMP and stirred under Ar atmosphere while cooled on ice for 40 minutes. Thereafter, phosphoryl chloride (100 μL, 1.07 mmol) was added and the mixture was stirred. After 30 minutes, additional phosphoryl chloride (85 μL, 9.2 mmol) was added thereto, quenched with 60 mL of cold water after 13.5 hours, and stirred for one hour. TEA was added thereto and stirred for another hour. The resultant was subjected to distillation under reduced pressure; and the precipitate was added with ether and MeCN and filtered. In the same operation, another compound 14 (145 mg, 0.232 mmol) was phosphorylated with a single unit of phosphoric acid, which was collectively subjected to anion exchange column chromatography. Fractions were collected and subjected to distillation under reduced pressure and freeze drying, thereby obtaining compound 15. The absolute yield was 377 μmol and the percentage yield was 60%.

ESI-MS (positive ion mode) m/z, found=706.0, calculated for [(M+H)$^+$]=706.1.

ESI-MS (negative ion mode) m/z, found=704.0, calculated for [(M-H)-]=704.1.

Synthesis of Compound 16

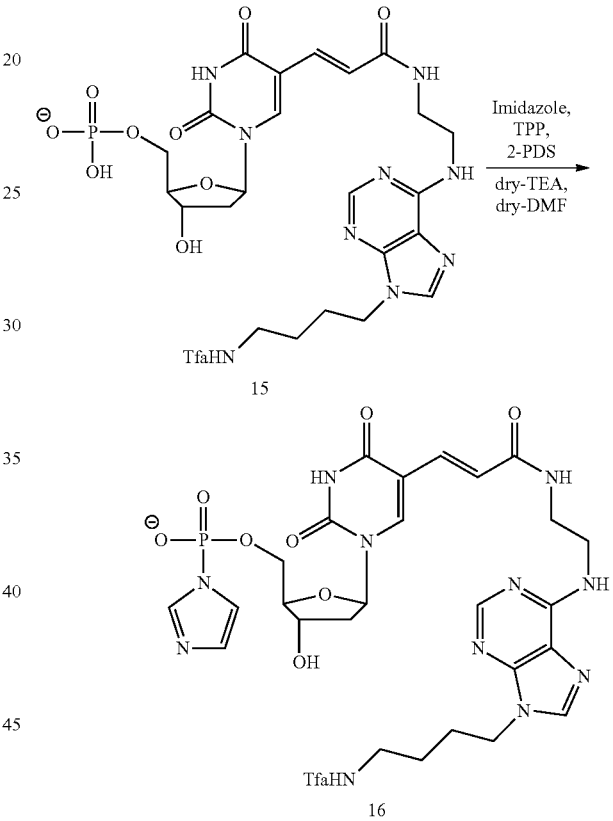

The compound 15 (377 μmol) that had been subjected to freeze drying was subjected to azeotropy with dry-pyridine (20 mL) once and dry-DMF (10 mL) once and dissolved in dry-DMF (2 mL); and dry-TEA (350 μL, 2.5 μmol), imidazole (103 mg, 1.51 mmol), triphenylphosphine (6.63 μmol, 174 mg), and 2,2'-dithiodipyridine (160 mg, 726 μmol) were added thereto and stirred under Ar atmosphere. Five hours later, sodium perchlorate (462 mg, 3.77 mmol) was dissolved in dry-Acetone (18 mL), dry-ether (27 mL), and dry-TEA (2 mL); and the reaction solution was added thereto and left to stand at 4° C. for 30 minutes. The precipitate was subjected to decantation with dry-ether (16 mL) six times. The precipitate was subjected to vacuum drying, thereby obtaining compound 16 as a crude product. The theoretical yield is 377 μmol.

ESI-MS (negative ion mode) m/z, found=754.2, calculated for [(M-H)-]=754.2.

Example 6

Synthesis of Compound 17 (dU$^{tf}$TP)

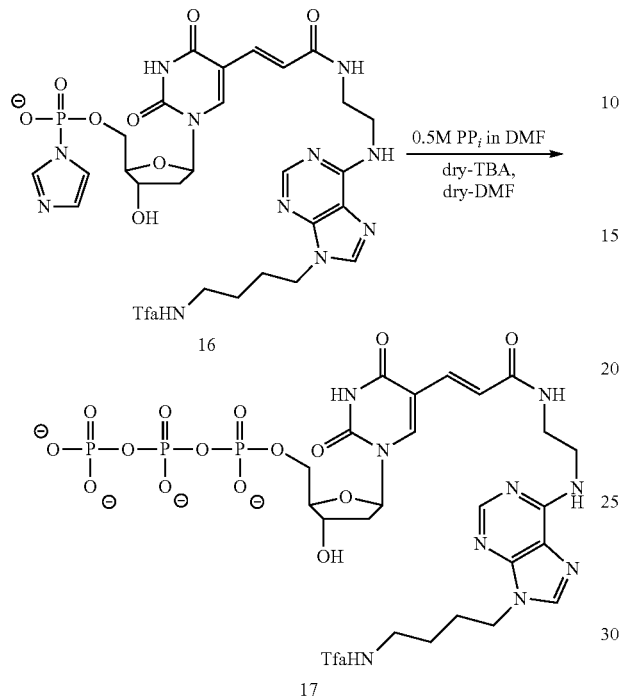

The compound 16 (377 μmol) that had been subjected to vacuum drying was subjected to azeotropy with dry-pyridine (5 mL) twice, suspended in dry-DMF (1 mL), and stirred; and dry-n-tributylamine (361 μL, 1.15 mmol) and 0.5 M n-tributylamine pyrophosphate in DMF (3.74 mL, 1.89 mmol) were added thereto and stirred under Ar atmosphere. Five hours later, the resultant was quenched with 5 mL of 1M TEAB buffer, stirred for 30 minutes, and thereafter subjected to distillation under reduced pressure. Water was added thereto and separation was performed using ether three times. The water layer was concentrated and then separated by anion exchange column chromatography. Fractions of interest were collected and thereafter purified by reversed phase HPLC followed by freeze drying, thereby obtaining compound 17 (dU$^{tf}$TP). The absolute yield was 93 μmol and the percentage yield was 24.7% (from the compound 15).

ESI-MS (negative ion mode) m/z, found=864.1, calculated for [(M−H)−]=864.1.

Example 7

Synthesis of Compound 18 (dU$^{am}$TP)

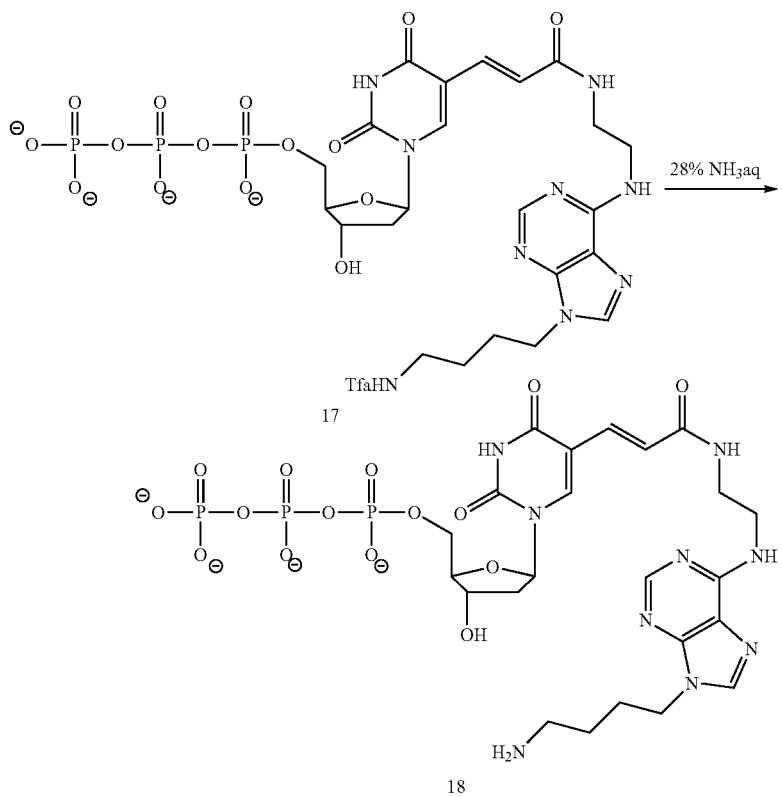

To the compound 17 (81 μmol) that had been subjected to freeze drying, 28% aqueous ammonia (4 mL) was added and the mixture was stirred. Two hours later, ammonia was taken out using a diaphragm pump. The resultant was subjected to freeze drying, purified by reversed phase HPLC, and subjected to freeze drying, thereby quantitatively obtaining compound 18 (dU$^{am}$TP).

ESI-MS (negative ion mode) m/z, found=768.1, calculated for [(M−H)−]=768.1.

Synthesis of Compound 19

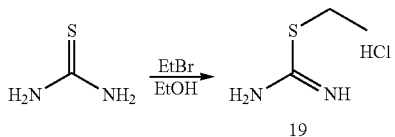

Thiourea (1 g, 13.1 mmol) was suspended in EtOH (2 mL) and stirred; and 1,2-dibromobutane (4.1 mL, 52.6 mmol) was added thereto and subjected to reflux at 55 to 65° C. for three hours. Thereafter, an equal amount of 1,2-dibromobutane was additionally added thereto and subjected to reflux for two hours. The resultant was subjected to distillation under reduced pressure and then crystallized with ether followed by decantation to obtain the residue as compound 19. The absolute yield was 2291 mg and the percentage yield was 94.2%.

ESI-MS (positive ion mode) m/z, found=105.2, calculated for [(M+H)$^+$]=105.0.

Example 8

Synthesis of Compound 20 (dU$^{gu}$TP)

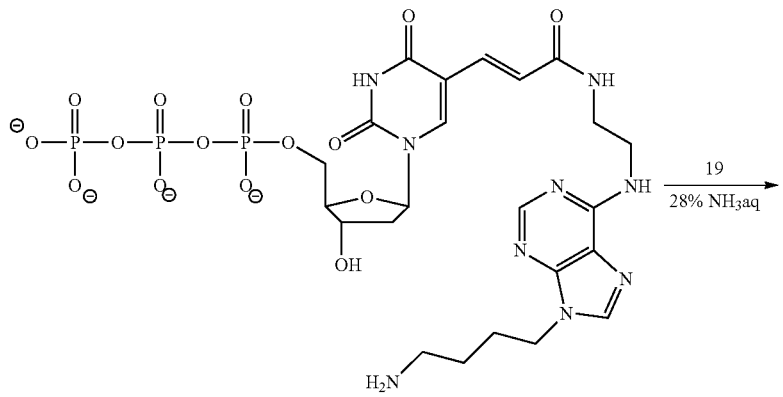

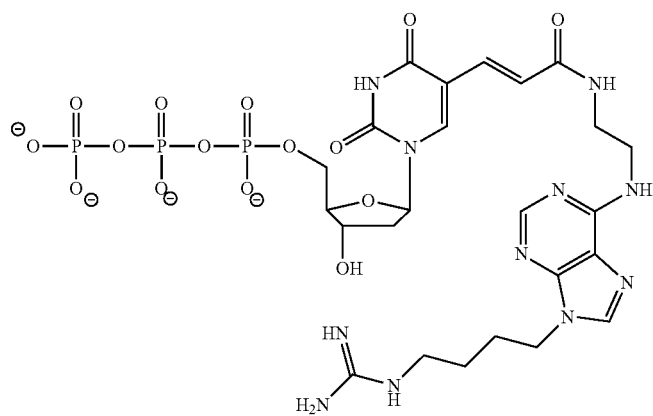

The compound 18 (38.9 μmol) that had been subjected to freeze drying was dissolved in 28% aqueous ammonia (400 μL); and the compound 19 (188 mg, 1.01 mmol) dissolved in 28% aqueous ammonia (400 μL) was added thereto and stirred. Two hours later, the resulting mixture was subjected to distillation under reduced pressure and freeze drying, purified by reversed phase HPLC, and subjected to freeze drying, thereby quantitatively obtaining compound 20 (dU-$^{gu}$TP).

ESI-MS (negative ion mode) m/z, found=810.1, calculated for [(M−H)−]=810.2

Example 9

Synthesis of Compound 21 (dU$^{dn}$TP)

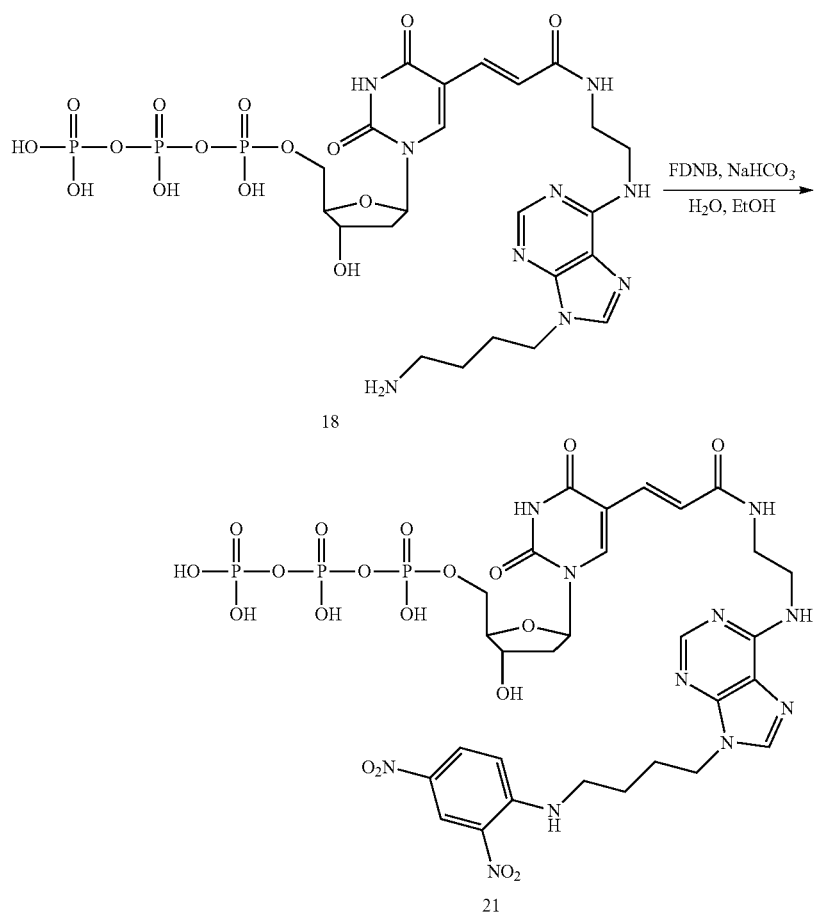

ESI-MS (negative ion mode) m/z, found=934.0, calculated for [(M−H)−]=934.1.

Synthesis of Compound 22

With 92 μL (2.76 mg, 13.5 μmol) of the solution obtained by dissolving dU$^{am}$TP (6.76 μmol) and 1-fluoro-2,4-dinitrobenzene (30 mg) in EtOH (1.0 mL), 23.6 μL (1.42 mg, 16.9 μmol) of the solution obtained by dissolving NaHCO$_3$ (30 mg) in water (0.5 mL) was mixed and stirred at room temperature for five hours. Centrifugation was carried out to collect a supernatant liquid, which was, after decantation with ether twice, separated by HPLC. This was subjected to distillation under reduced pressure and freeze drying; and the resultant was dissolved in sterilized water and stored. The absolute yield was 2.65 μmol and the percentage yield was 39%.

Sodium 1-naphthol-5-sulfonate (1 g, 4.06 mmol) and NaHSO₃ (3.4 g, 32.7 mmol) were weighed, added with water (12.3 mL), and stirred. Thereafter, ethylenediamine (814 μL, 12.2 mmol) was added thereto. The pH was adjusted to not more than 8 with conc. HCl and the resulting mixture was subjected to reflux for 13.5 hours. The reaction solution was filtered and washed with cold water and acetonitrile; and the residue after filtration was subjected to vacuum drying. The absolute yield was 791 mg and the percentage yield was 73%.

¹HNMR (400 MHz, DMSO-D6) δ 8.19 (1H, d) 8.13 (1H, d) 7.94 (1H, d) 7.35 (1H, t) 7.28 (1H, t) 6.57 (1H, d) 3.42 (2H, t) 3.15 (2H, t)

ESI-MS (positive ion mode) m/z, found=289.1, calculated for [(Mina)⁺]=289.1.

ESI-MS (negative ion mode) m/z, found=265.0, calculated for [(M−H)−]=265.1.

Synthesis of Compound 23

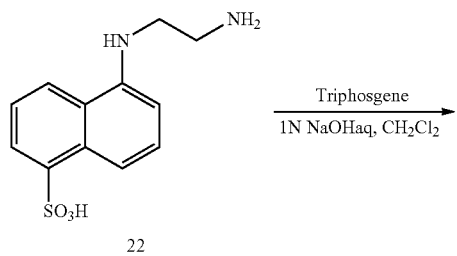

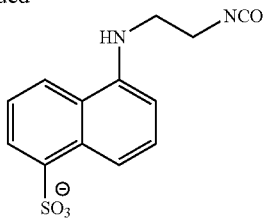

The compound 22 (159 mg, 597 μmol) was dissolved in 1 N NaOHaq (3 mL) and chloroform (1.5 mL) was added thereto; and the mixture was stirred in an ice bath for 30 minutes. Triphosgene (266, mg, 895 μmol) that has been dissolved in chloroform (1.5 mL) was slowly poured into the organic layer and stirred for 15 minutes. The aqueous phase was filtered; and the filtrate was purified by a medium pressure column and subjected to vacuum drying. The absolute yield was 106 to 176 mg and the percentage yield was 56 to 97%.

¹HNMR (400 MHz, D2O) δ8.67 (1H, d) 8.20 (2H, m) 7.76 (1H, t) 7.65 (2H, q) 4.06 (2H, t) 3.76 (2H, t)

ESI-MS (negative ion mode) m/z, found=291.0, calculated for [(M−H)−]=291.1

By reacting the compound 23 and the compound 18 as shown in the following formula, a compound in which the structure of the compound 23 is introduced to the position of Y in the formulae (I-1) to (I-6) can be obtained.

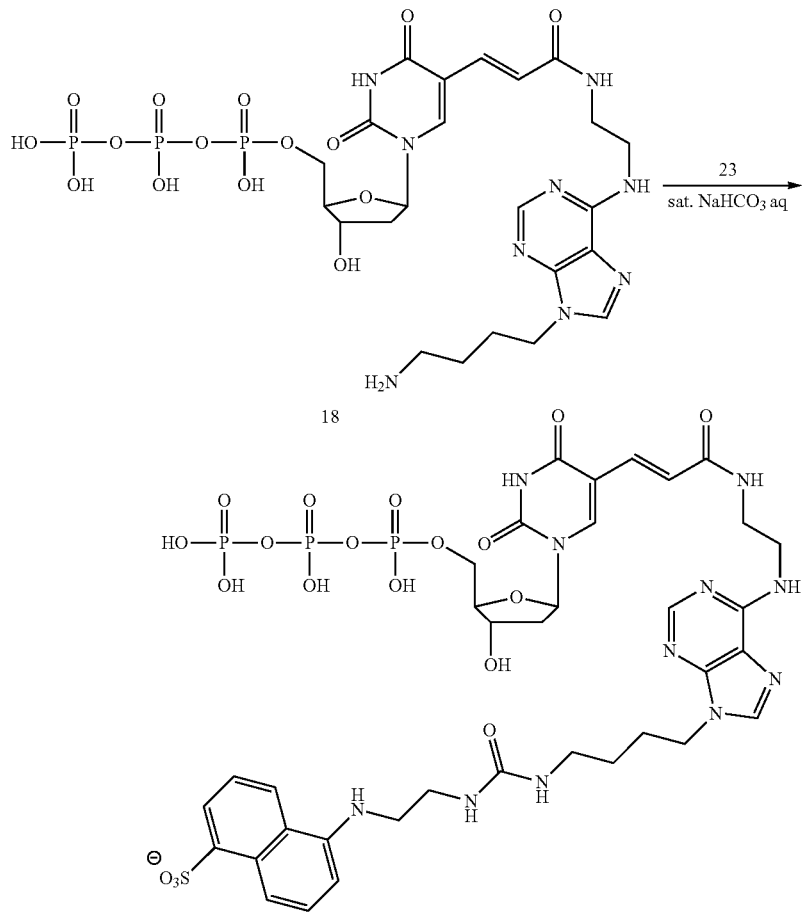

Further, by forming an isocyanate group (—NCO) in the same manner as described for the compound 23 and reacting it with the compound 18 or the like, a structure of interest can be introduced to the position of Y.
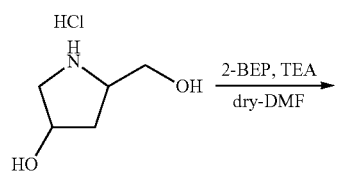
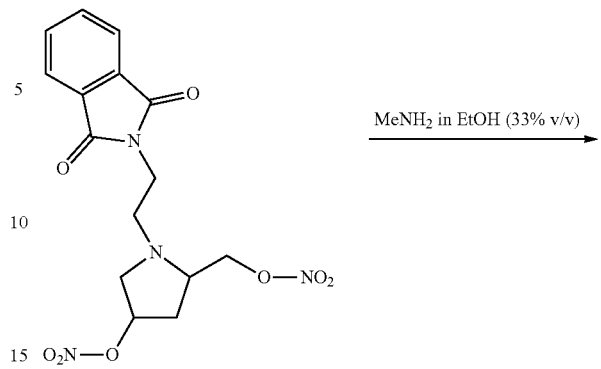
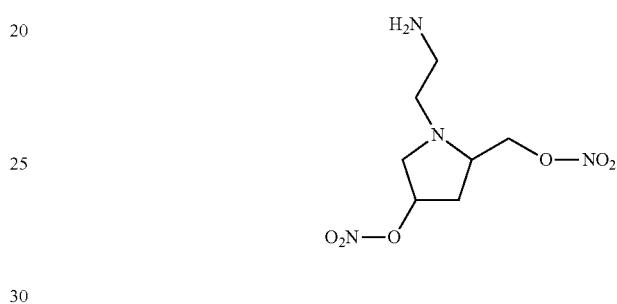
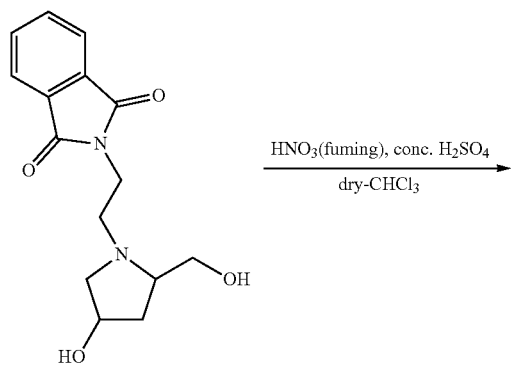
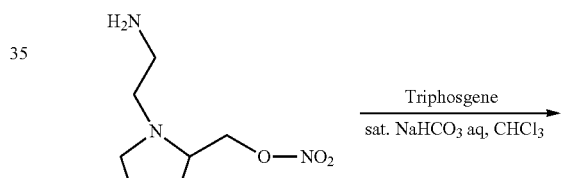
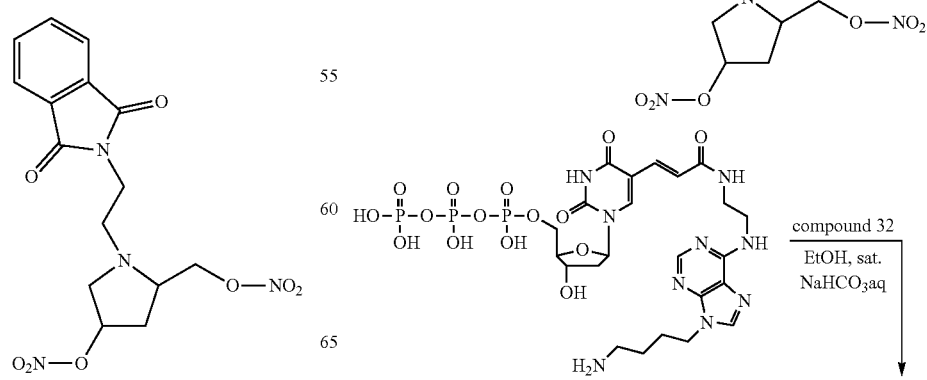

-continued

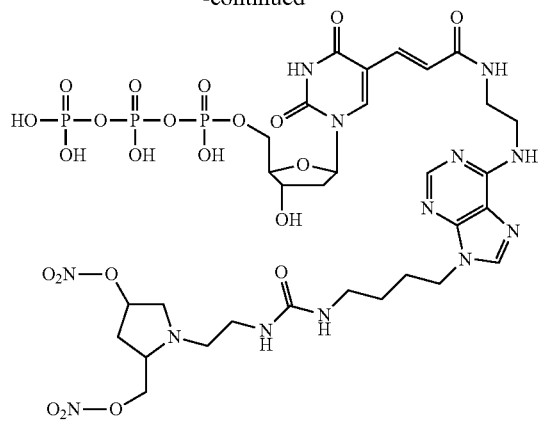

Example 10

[Enzymatic Introduction of Four Kinds of Triphosphates]

Reaction solutions that contain each substrate in the composition (except for enzymes) shown in the following Table 1 were each prepared in a 500 μL microtube; and denaturing (95° C., 1 min) and annealing (95° C.→25° C., 0.5° C./min) were performed using a thermal cycler. Subsequently, KOD™ (Toyobo Co., Ltd.), which is a DNA polymerase mixture (2.5 U/μl) in a 10×PCR buffer and deoxyribonucleotide triphosphates (dNTPs) (2 mM), was added for extension (74° C., 0.5 or 5 min). The extension reaction was checked by 20% denatured polyacrylamide gel electrophoresis (300 V, 100 mM, 140 min, 45° C.) followed by conducting imaging (FAM) by laser irradiation (488 nm). The imaging is shown in FIG. 1 and the correspondence table is shown in Table 2.

TABLE 2

| Lane | Substrate | Time(min) | |
|---|---|---|---|
| ① | Template only | 5 | |
| ② | NEG | 5 | |
| ③ | POS(TTP) | 0.5 | |
| ④ | POS(TTP) | 5 | |
| ⑤ | R(dU$^{ad}$TP) | 0.5 | |
| ⑥ | R(dU$^{ad}$TP) | 5 | |
| ⑦ | R(dU$^{tf}$TP) | 0.5 | |
| ⑧ | R(dU$^{tf}$TP) | 5 | |
| ⑨ | R(dU$^{am}$TP) | 0.5 | |
| ⑩ | R(dU$^{am}$TP) | 5 | |
| ⑪ | R(dU$^{gu}$TP) | 0.5 | |
| ⑫ | R(dU$^{gu}$TP) | 5 | |
| ⑬ | R(dU$^{ia}$TP) | 0.5 | |
| ⑭ | R(dU$^{ia}$TP) | 5 | |
| ⑮ | R(dU$^{ia}$TP) | 5 | Enzyme concentration ten times |

[Enzymatic Introduction of dU$^{dn}$TP]

Figure 2:
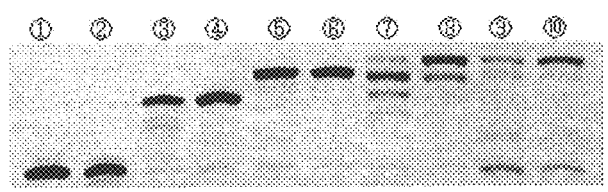
FIG. 2 is a photograph of polyacrylamide gel electrophoresis of the polynucleotide to which $dU^{dn}TP$ etc. has been introduced (drawing substituting photograph).

Reaction solutions were each prepared in the composition (except for enzymes) shown in the following Table 3 in a 500 μL microtube; and annealing (95° C.→25° C., 0.5° C./min) was performed for one hour. Subsequently, KOD Dash was added for extension (74° C., 0.5 or 5 min). A 1.4-fold amount of dye liquid with respect to the amount of the reaction solution was used for quenching, followed by denaturing (95° C., 5 min). The extension reaction was checked by 20% denatured polyacrylamide gel electrophoresis (300 V, 100 mM, 140 min, 45° C.) followed by conducting imaging (FAM) by laser irradiation (488 nm). The imaging is shown in FIG. 2 and the correspondence table is shown in Table 4.

TABLE 1

| <Scale> | mother liquor | Final | amount used |
|---|---|---|---|
| Primer YTM#P24 | | | |
| 5'-GGATTAGCGAACAGGCCATACCTT-3' (SEQ ID NO: 1) | 3 μM | 0.3 μM | 2 μL |
| Template YTM#T31A6 | | | |
| 5'-GCGAAAAAAGGTATGGCCTGTTCGCTAATCC-3' (SEQ ID NO: 2) | 4 μM | 0.4 μM | 2 μL |
| Substrate | | | |
| dATP, dGTP, dCTP | 2 mM | 0.2 mM | 2 μL |
| Water or TTP or dU$^{ad}$TP or dU$^{ia}$TP or dU$^{tf}$TP or dU$^{am}$TP or dU$^{gu}$TP | 2 mM | 0.2 mM | 2 μL |
| KOD DASH™ buffer | 10× | 1× | 2 μL |
| Water | — | — | 8 μL |
| KOD DASH™ | 0.0125 u/μL | 0.00125 u/μL | 2 μL |
| | | total | 20 μL |

TABLE 3

| <Scale> | mother liquor | Final | amount used |
|---|---|---|---|
| Primer YTM#P24 | | | |
| 5'-GGATTAGCGAACAGGCCATACCTT-3' (SEQ ID NO: 1) | 3 µM | 0.3 µM | 2 µL |
| Template YTM#T31A6 | | | |
| 5'-GCGAAAAAAGGTATGGCCTGTTCGCTAATCC-3' (SEQ ID NO: 2) | 4 µM | 0.4 µM | 2 µL |
| Substrate | | | |
| dAGC | 2 mM | 0.2 mM | 2 µL |
| dU$^{dn}$TP | 2 mM | 0.2 mM | 2 µL |
| KOD Dash buffer | 10× | 1× | 2 µL |
| Water | — | — | 8 µL |
| KOD Dash | 0.0125 u/µL | 0.00125 u/µL | 2 µL |
| | | total | 20 µL |

TABLE 4

| Lane | Substrate | Time(min) |
|---|---|---|
| ① | Template only | 5 |
| ② | NEG | 5 |
| ③ | POS(TTP) | 0.5 |
| ④ | POS(TTP) | 5 |
| ⑤ | POS(dU$^{ad}$TP) | 0.5 |
| ⑥ | POS(dU$^{ad}$TP) | 5 |
| ⑦ | POS(dU$^{am}$TP) | 0.5 |
| ⑧ | POS(dU$^{am}$TP) | 5 |
| ⑨ | R(dU$^{dn}$TP) | 0.5 |
| ⑩ | R(dU$^{dn}$TP) | 5 |

[Enzymatic Preparation of DNA Library Containing Modified Nucleotides]

A reaction solution was prepared in a 1.5 mL microtube as follows. This was aliquoted into eight parts, each of which contained 100 µL in a 500 µL microtube, and set in a gene amplification apparatus to carry out PCR in the following temperature condition. The PCR product was checked by 10% denatured polyacrylamide gel electrophoresis (TBE buffer, 200 V, 45° C., 35 min) followed by external laser (488 nm) irradiation. After the confirmation, the reaction solution was subjected to 10% denatured polyacrylamide gel electrophoresis (TB buffer, 200 or 300 V, 45 or 4° C., 150 to 250 min) to detect an intended DNA band of 70 mer by external laser (488 nm) irradiation, which band was cut out from the gel. The excised gel was subjected to dialysis (TB buffer, 100 V, 4° C., 80 min) using a dialysis tube. The extracted DNA elution liquid was desalted by a centrifugation filter unit and subjected to freeze drying. The resultant was then dissolved in an appropriate amount of sterilized water and the concentration was measured, thereby obtaining a library.

TABLE 5

| PCR condition where KOD Dash DNA polymerase was used | | | |
|---|---|---|---|
| <Scale> | mother liquor | Final | amount used |
| Primer | | | |
| GOL#P1F (SEQ ID NO: 3) 5'-tcgctcggcaggatcgcaag-3' | 4 µM | 0.4 µM | 80 µL |
| Template | | | |
| GOL#T2H(1R) (SEQ ID NO: 4) 5'-tgctgccactgctccgtccannnnnnnnnnnnnnn nnnnn nnnnnnnnnn cttgcgatcctgccgagcga-3' or Solution prepared by λ-exonuclease (2R or later) | 800 nM | 80 nM | 80 µL |
| Substrate | | | |
| dATP, dGTP, dCTP | 2 mM | 0.2 mM | 80 µL |
| Modified Nucleoside triphosphate | 2 mM | 0.2 mM | 80 µL |
| KOD Dash buffer | 10× | 1× | 80 µL |
| Water | — | — | 320 µL |
| KOD Dash | 0.05 U/µL | 0.005 U/µL | 80 µL |
| | | total | 800 µL |

TABLE 6

| Condition | | | |
|---|---|---|---|
| Preheating | 94° C. | 1 min | |
| Denature | 94° C. | 0.5 min | |
| Annealing | 54° C. | 0.5 min | 8~20 cycle |
| Extension | 74° C. | 1 min | |
| Final incubation | 74° C. | 5 min | |

Example 11

[Selection of Library by NECEEM]

An initial library was prepared in a 500 µL microtube so as to have a concentration of 1 µM in a buffer. As for the buffer, Tris-HCl buffer (20 mM Tris-HCl (pH 7.4), 1 mM $MgCl_2$, 10 mM NaCl) was used. This was set in a gene amplification apparatus and subjected to thermal denaturation at 94° C. for 0.5 min and annealing by lowering the temperature to 25° C. at a rate of 0.5° C./min. Thereafter, a protein, which is a target molecule, was added to a positive control so as to have a final concentration of 0.2 µM and the mixture was incubated at 37° C. for 30 minutes. As a negative control, the buffer was added. At that time, both of the positive control and negative control were prepared so as to have a DNA concentration of 0.5 µM. After the incubation, measurement was carried out by nonequilibrium capillary electrophoresis of equilibrium mixtures (NECEEM). As for the measurement condition, the following conditions were employed. Fractions in which increased fluorescence intensity was observed as compared with the negative control were separately collected. In addition, in order to check if DNA was adsorbed by the inner wall of the capillary, a fraction was separately collected before the reaction solution was injected.

<Electrophoresis Condition>
Capillary length: 80 cm
Running buffer: 100 mM boric acid buffer (pH 8.4)
Temperature cartridge: 25° C.
Sample storage: 15° C.
Dynamic range: 1000 RFU
Excitation wavelength: 488 nm
Emission wavelength: 520 nm

TABLE 7

| 100 mM NaOH | 20 psi | 8 min |
|---|---|---|
| Water | 20 psi | 8 min |
| Running buffer | 20 psi | 8 min |
| Inject | 0.5 psi | 16 sec |
| After 0.5 min | Autozero | |
| Selection | 18 kV | 25 min |
| Water | 20 psi | 4 min |
| RNase | 20 psi | 8 min |
| New water | 20 psi | 8 min |

[Enzymatic Preparation of DNA Library Containing Modified Nucleotides]

A reaction solution was prepared in a 1.5 mL microtube as follows. This was aliquoted into eight parts, each of which contained 100 µL in a 500 µL microtube, and set in a gene amplification apparatus to carry out PCR in the following temperature condition. The PCR product was checked by 10% denatured polyacrylamide gel electrophoresis (TBE buffer, 200 V, 45° C., 35 min) followed by external laser (488 nm) irradiation. After the confirmation, the reaction solution was subjected to 10% denatured polyacrylamide gel electrophoresis (TB buffer, 200 or 300 V, 45 or 4° C., 150 to 250 min) to detect an intended DNA band of 70 mer by external laser (488 nm) irradiation, which band was cut out from the gel. The excised gel was subjected to dialysis (TB buffer, 100 V, 4° C., 80 min) using a dialysis tube. The extracted DNA elution liquid was desalted by a centrifugation filter unit and subjected to freeze drying. The resultant was then dissolved in an appropriate amount of sterilized water and the concentration was measured, thereby obtaining a library.

TABLE 8

| PCR condition where KOD Dash DNA polymerase was used | | | |
|---|---|---|---|
| <Scale> | mother liquor | Final | amount used |
| Primer | | | |
| GOL#P1P (SEQ ID NO: 3) 5'-tcgctcggcaggatcgcaag-3' | 4 µM | 0.2 µM | 0.5 µL |
| GOL#P2H (SEQ ID NO: 5) 5'-tgctgccactgctccgtcca-3' | 4 µM | 0.2 µM | 0.5 µL |
| Template | | | |
| Solution taken | | | 4 µL |
| Substrate | | | |
| dNTPs | 2 mM | 0.2 mM | 1 µL |
| KOD Dash buffer | 10x | 1x | 1 µL |
| Water | — | — | 1 µL |
| KOD Dash | 0.025 U/µL | 0.005 U/µL | 2 µL |
| | | total | 10 µL |

TABLE 9

| Condition | | |
|---|---|---|
| Preheating | 94° C. | 1 min |
| Denature | 94° C. | 0.5 min |
| Annealing | 54° C. | 0.5 min |
| Extension | 74° C. | 1 min |
| Final incubation | 74° C. | 5 min |

20 cycle (Denature, Annealing, Extension)

[Second PCR]

A reaction solution was prepared in a 1.5 mL microtube as follows. This was aliquoted into eight parts, each of which contained 100 μL in a 500 μL microtube, and set in a gene amplification apparatus to carry out symmetric PCR in the following temperature condition. The PCR product was checked by 10% denatured polyacrylamide gel electrophoresis (TBE buffer, 200 V, 45° C., 35 min) followed by external laser (488 nm) irradiation. The reaction solution was subjected to ethanol precipitation using sodium acetate followed by freeze drying. The residue was then dissolved in 80 μL of sterilized water.

TABLE 10

PCR condition where KOD Dash DNA polymerase was used

| \<Scale\> | mother liquor | Final | amount used |
|---|---|---|---|
| Primer | | | |
| GOL#P1P (SEQ ID NO: 3) 5'-tcgctcggcaggatcgcaag-3' | 4 μM | 0.4 μM | 80 μL |
| GOL#P2H (SEQ ID NO: 5) 5'-tgctgccactgctccgtcca-3' | 4 μM | 0.4 μM | 80 μL |
| Template | | | |
| Solution prepared by 1st PCR | | | 80 μL |
| Substrate | | | |
| dNTPs | 2 mM | 0.2 mM | 80 μL |
| KOD Dash buffer | 10× | 1× | 80 μL |
| Water | — | — | 320 μL |
| KOD Dash | 0.05 U/μL | 0.005 U/μL | 80 μL |
| total | | | 800 μL |

TABLE 11

| Condition | | |
|---|---|---|
| Preheating | 94° C. | 1 min |
| Denature | 94° C. | 0.5 min |
| Annealing | 54° C. | 0.5 min |
| Extension | 74° C. | 1 min |
| Final incubation | 74° C. | 5 min |

16 cycle (Denature, Annealing, Extension)

[Breakdown of Complementary Strand by λ-Exonuclease]

A reaction solution without an enzyme was prepared in a 1.5 mL microtube as follows. This was aliquoted into eight parts, each of which contained 90 μL in a 500 μL microtube, and set in a gene amplification apparatus to carry out annealing (a rate of lowering temperature 1.2° C./min, 95→25° C.). Thereafter, 10 μL of λ-exonuclease was added thereto; and the reaction was carried out at 37° C. for 30 minutes. Breakdown of the complementary strand was checked by 10% denatured polyacrylamide gel electrophoresis (TBE buffer, 200 V, 45° C., 35 min) and then staining with SYBR Gold, followed by external laser (488 nm) irradiation. The reaction solution was desalted by a spin column (10 k) and subjected to freeze drying. The residue was dissolved in 400 μL of sterilized water.

TABLE 12

Reaction condition where λ-exonuclease was used

| \<Scale\> | mother liquor | final | amount used |
|---|---|---|---|
| Template | | | |
| Solution prepared by 2nd PCR | 4 μM | 0.4 μM | 80 μL |
| Reaction buffer | 10× | 1× | 80 μL |
| Water | — | — | 560 μL |
| λ-exonuclease | 0.25 U/μL | 0.025 U/μL | 80 μL |
| total | | | 800 μL |

Figure 3:
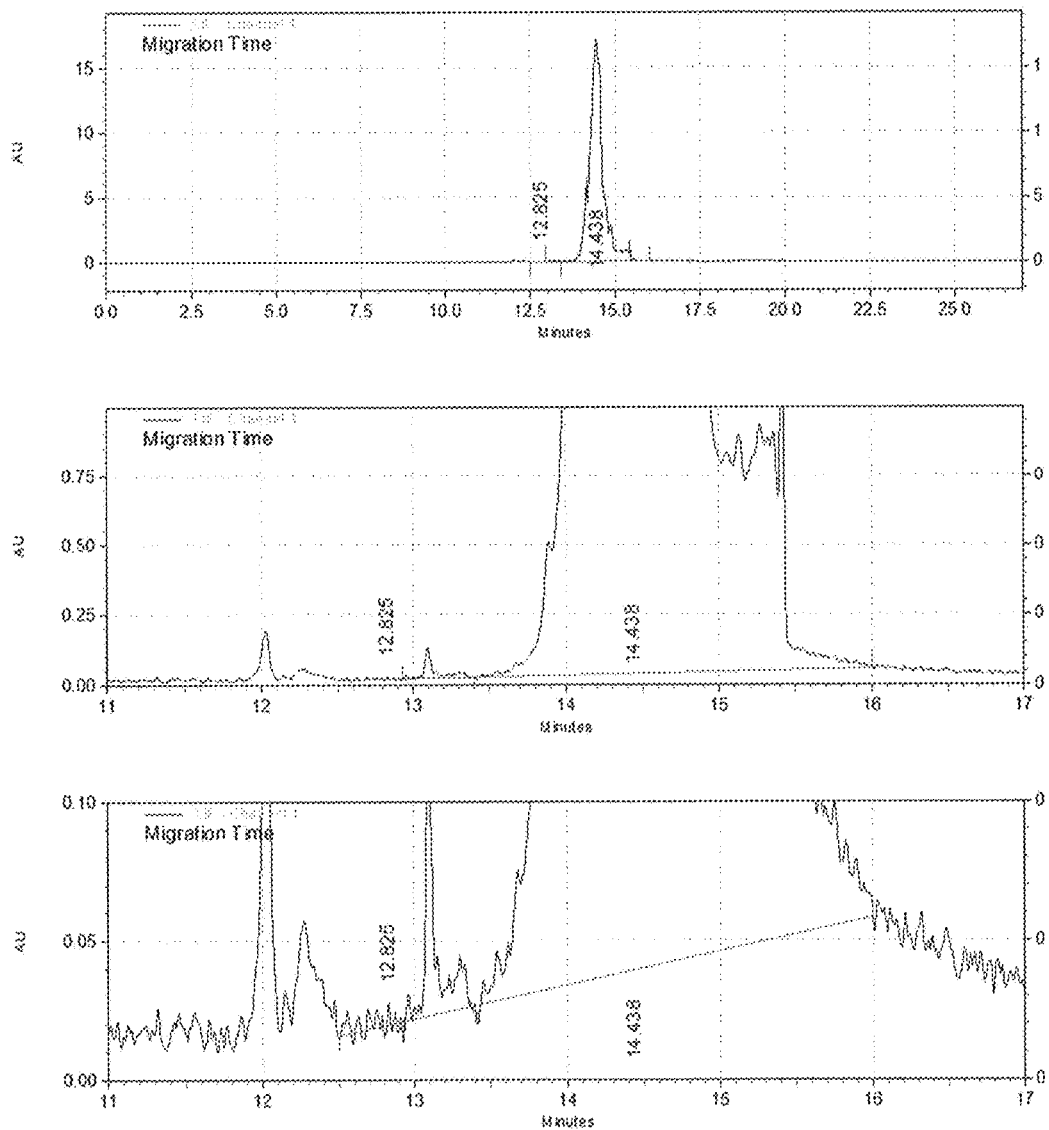
FIG. 3 is the measurement result of the first round nonequilibrium capillary electrophoresis of equilibrium mixtures (NECEEM) of $dU^{gu}TP$-Library (without the target molecule (thrombin)).
Figure 4:
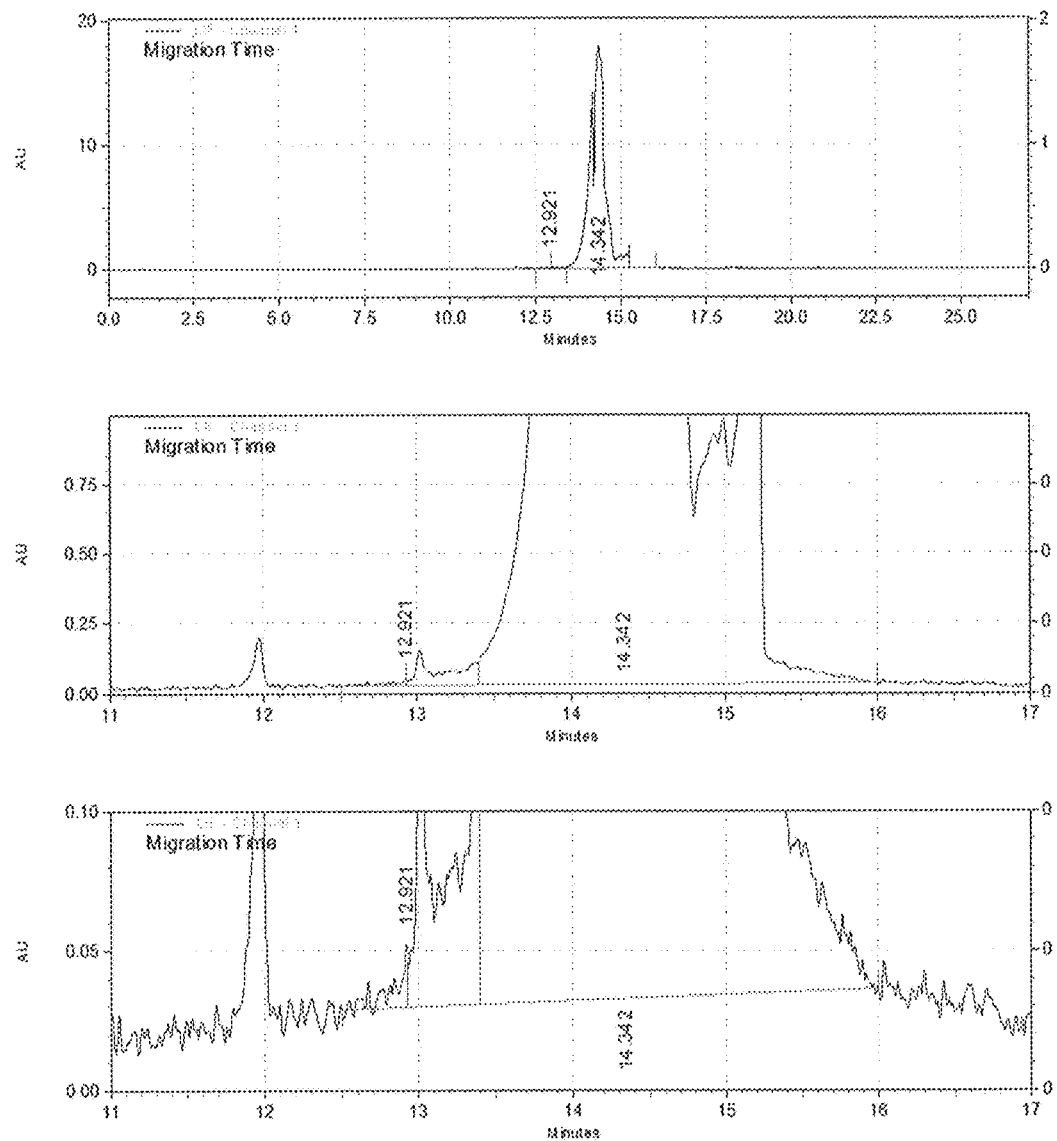
FIG. 4 is the measurement result of the first round NECEEM of $dU^{gu}TP$-Library (with the target molecule (thrombin)).
Figure 5:
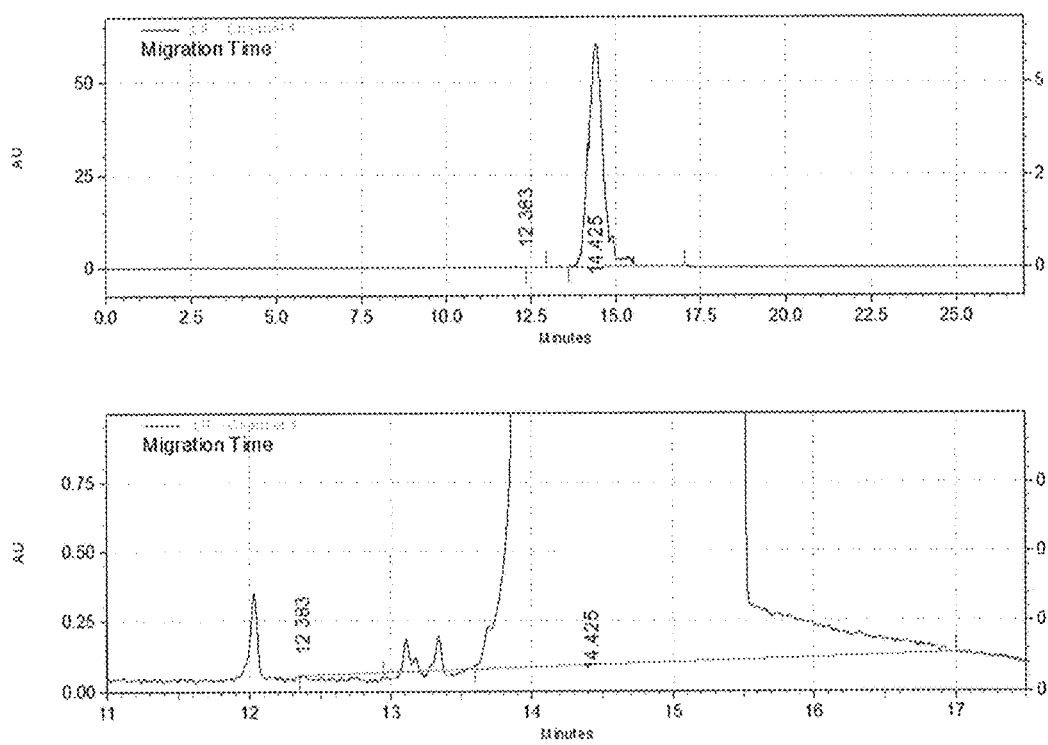
FIG. 5 is the measurement result of the second round NECEEM of $dU^{gu}TP$-Library (without the target molecule (thrombin)).
Figure 6:
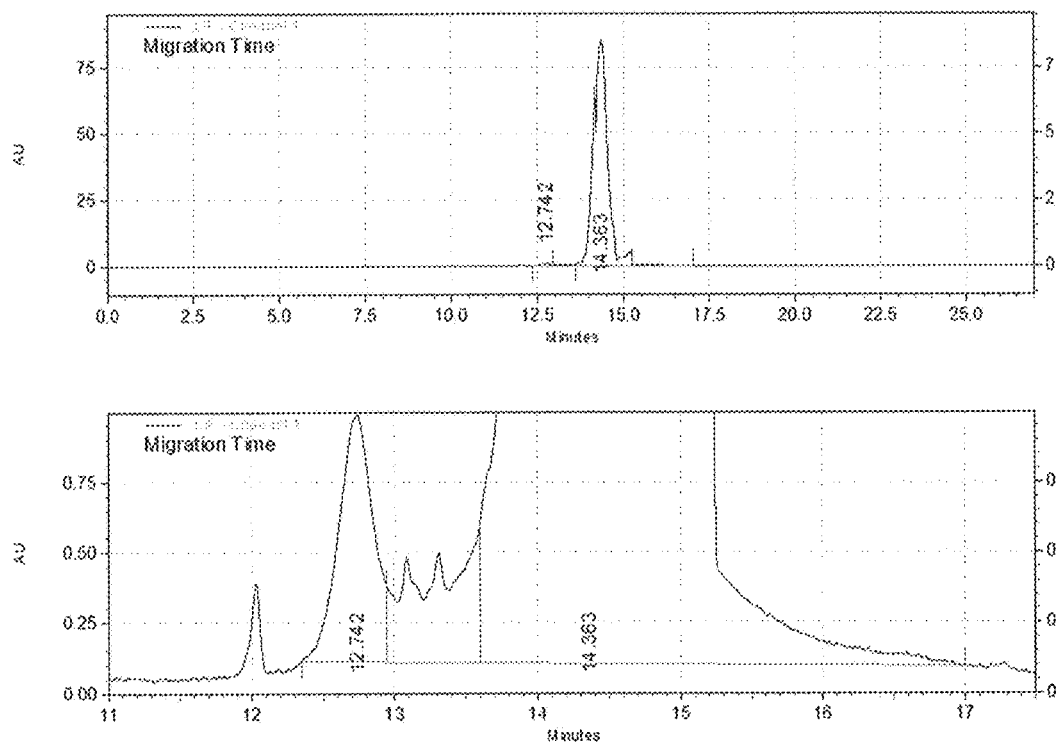
FIG. 6 is the measurement result of the second round NECEEM of $dU^{gu}TP$-Library (with the target molecule (thrombin)).

The measurement results of the first round NECEEM of dU$^{gu}$TP-Library (without the target molecule (thrombin)) are shown in FIG. 3; the measurement results of the first round NECEEM of dU$^{gu}$TP-Library (with the target molecule (thrombin)) are in FIG. 4; the measurement results of the second round NECEEM of dU$^{gu}$TP-Library (without the target molecule (thrombin)) are in FIG. 5; and the measurement results of the second round NECEEM of dU$^{gu}$TP-Library (with the target molecule (thrombin)) are in FIG. 6. The difference between areas with the target molecule and without the target molecule in the first round was 0.01%; and the difference between areas with the target molecule and without the target molecule in the second round was 0.56%; and the concentration ratio was 56 times. In addition, the difference between complex peak areas of the first round and the second round was 0.58%; and the concentration ratio was 30 times (0.02%→0.60%).

Figure 7:
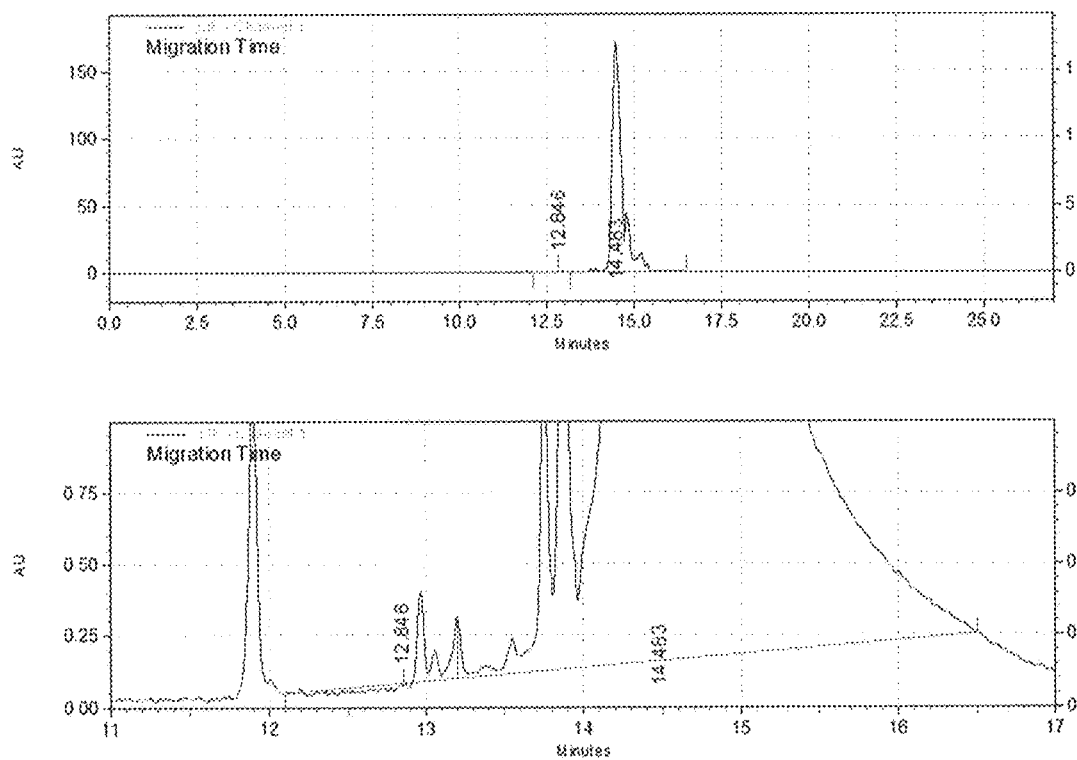
FIG. 7 is the measurement result of the first round NECEEM of $dU^{ad}TP$-Library (without the target molecule (thrombin)).
Figure 8:
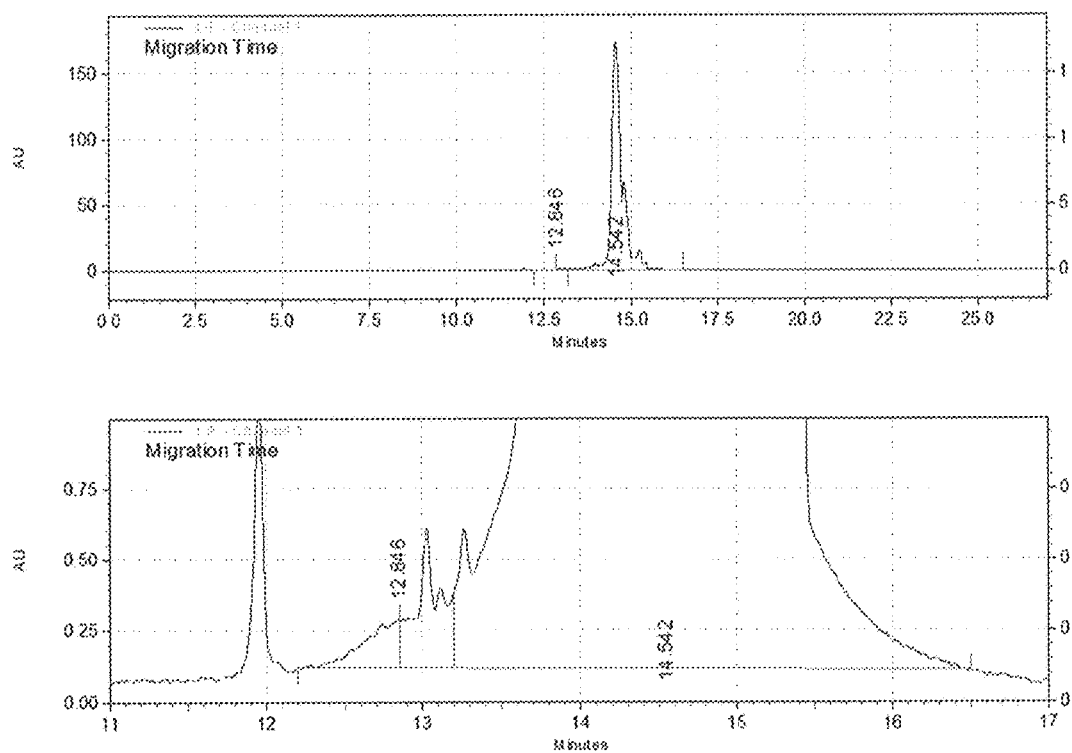
FIG. 8 is the measurement result of the first round NECEEM of $dU^{ad}TP$-Library (with the target molecule (thrombin)).
Figure 9:
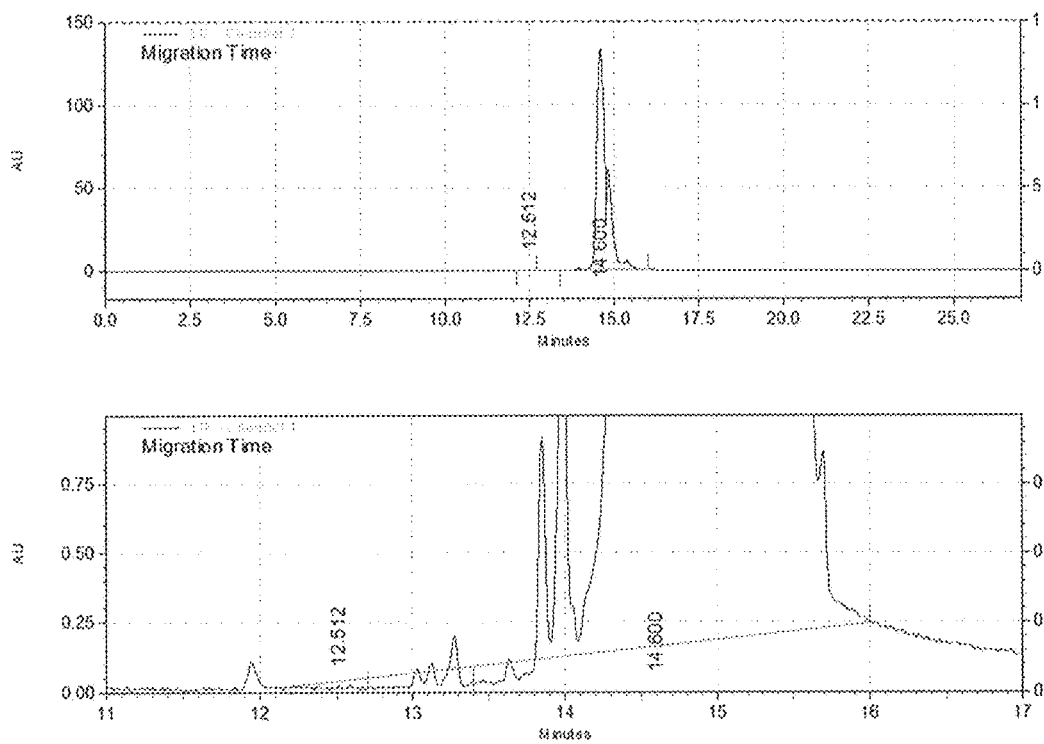
FIG. 9 is the measurement result of the second round NECEEM of $dU^{ad}TP$-Library (without the target molecule (thrombin)).
Figure 10:
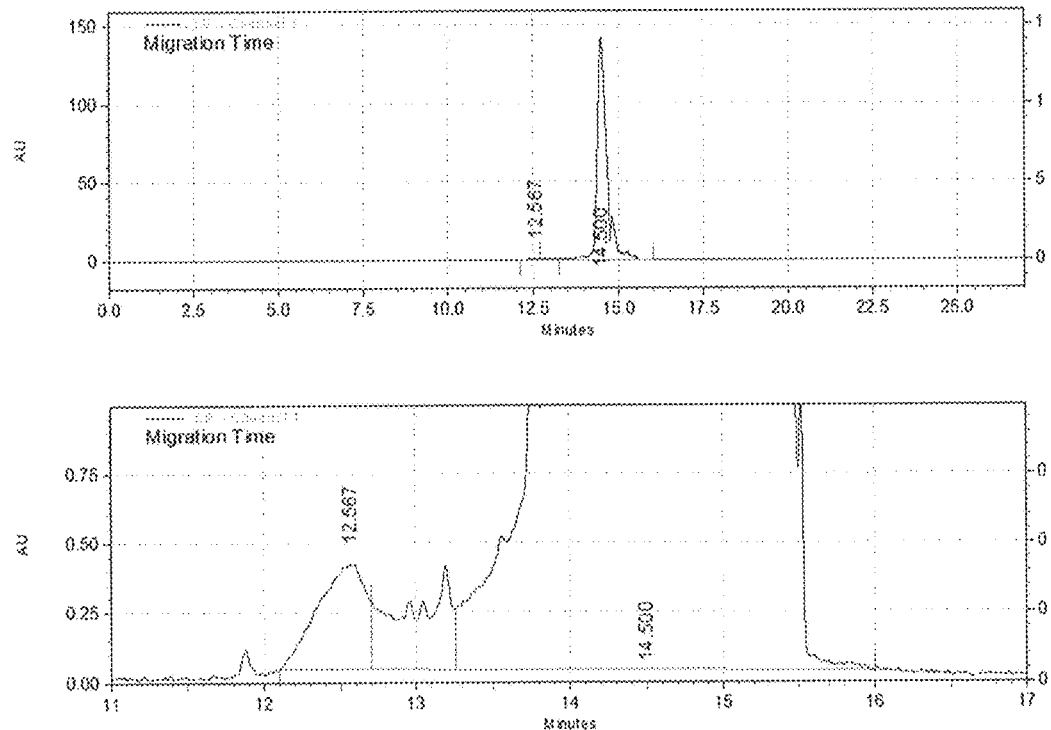
FIG. 10 is the measurement result of the second round NECEEM of $dU^{ad}TP$-Library (with the target molecule (thrombin)).

The measurement results of the first round NECEEM of dU$^{ad}$TP-Library (without the target molecule (thrombin)) are shown in FIG. 7; the measurement results of the first round NECEEM of dU$^{ad}$TP-Library (with the target molecule (thrombin)) are in FIG. 8; the measurement results of the second round NECEEM of dU$^{ad}$TP-Library (without the target molecule (thrombin)) are in FIG. 9; and the measurement results of the second round NECEEM of dU$^{ad}$TP-Library (with the target molecule (thrombin)) are in FIG. 10. The difference between areas with the target molecule and without the target molecule in the first round was 0.06%; and the difference between areas with the target molecule and without the target molecule in the second round was 0.28%; and the concentration ratio was 4.7 times. In addition, the difference between complex peak areas of the first round and the second round was 0.23%; and the concentration ratio was 4.3 times (0.07%→0.30%).

Example 12

The above compound 20 was used as compound (i) (KK10) in the following experiment.
Experimental Method of CE-SELEX DNAs used
GOL#P1P:
(SEQ ID NO: 3)
5'-TCG CTC GGC AGG ATC GCA AG-3'
(5' was phosphorylated)

GOL#P1F:
(SEQ ID NO: 3)
5'-TCG CTC GGC AGG ATC GCA AG-3'
(5' was labeled with FITC (6-FAM))

GOL#P2P:
(SEQ ID NO: 5)
5'-TGC TGC CAC TGC TCC GTC CA-3'
(5' was phosphorylated)

GOL#P2H:
(SEQ ID NO: 5)
5'-TGC TGC CAC TGC TCC GTC CA-3'

GOL#T2H:
(SEQ ID NO: 4)
5'-TGC TGC CAC TGC TCC GTC CAN NNN NNN NNN NNN

NNN NNN NNN NNN NNN NNC TTG CGA TCC TGC CGA GCG A-3'

[Enzymatic Preparation of Modified DNA Library]

A reaction solution was prepared in a 1.5 mL microtube as follows. This was aliquoted into eight parts, each of which contained 100 μL in a 500 μL microtube, and set in a gene amplification apparatus to carry out PCR in the following temperature condition. The PCR product was checked by 10% denatured polyacrylamide gel electrophoresis (TBE buffer, 200 V, 45° C., 35 min) followed by external laser (488 nm) irradiation. After the confirmation, the reaction solution was subjected to 10% denatured polyacrylamide gel electrophoresis (TB buffer, 300 V, 4° C., 200 to 240 min) to detect an intended DNA band of 70 mer by external laser (488 nm) irradiation, which band was cut out from the gel. The excised gel was subjected to dialysis (TB buffer, 100 V, 4° C., 80 min) using a dialysis tube. The extracted DNA elution liquid was desalted by a centrifugation filter unit and subjected to freeze drying. The resultant was then dissolved in an appropriate amount of distilled water and the concentration was measured, thereby obtaining a library.

TABLE 13

Reaction condition where KOD Dash DNA polymerase was used

| <Scale> | mother liquor | final | amount used |
|---|---|---|---|
| Primer | | | |
| GOL#P1F | 4 μM | 0.4 μM | 80 μL |
| Template | | | |
| GOL#T2H (1 round) or solution prepared by λ-exonuclease (2 round or later) Substrate | 800 nM | 80 nM | 80 μL |
| dATP, dGTP, dCTP | 2 mM | 0.2 mM | 80 μL |
| Modified Nucleoside triphosphate | 2 mM | 0.2 mM | 80 μL |
| KOD Dash buffer | 10× | 1× | 80 μL |
| Water | — | — | 320 μL |
| KOD Dash | 0.05 U/μL | 0.005 U/μL | 80 μL |
| total | | | 800 μL |

TABLE 14

| Condition | | | |
|---|---|---|---|
| Preheating | 94° C. | 1 min | |
| Denature | 94° C. | 0.5 min | |
| Annealing | 54° C. | 0.5 min | 8~20 cycle |
| Extension | 74° C. | 1 min | |
| Final incubation | 74° C. | 5 min | |

[Selection of Modified DNA Library by NECEEM]

The library that was synthesized above was prepared in a 500 μL microtube so as to have a concentration of one μM in a buffer. As for the buffer, Tris-HCl buffer (20 mM Tris-HCl (pH 7.4), 1 mM MgCl$_2$, 10 mM NaCl) was used. This was set in a gene amplification apparatus and subjected to thermal denaturation at 94° C. for 0.5 min and annealing by lowering the temperature to 25° C. over 2.5 hours. Thereafter, human VEGF protein, which is a target molecule, was added so as to have a final concentration of 0.5 μM (only the first round) or 0.2 μM (the second round or later); and incubation was carried out at 37° C. for 30 minutes. As a negative control, the buffer was added. At that time, the concentration of DNA was adjusted to 0.5 μM. After the incubation, measurement was carried out by non-equilibrium capillary electrophoresis of equilibrium mixtures (NECEEM). As for the measurement condition, the following conditions were employed. Fractions in which increased fluorescence intensity was observed as compared with the negative control were separately collected. In addition, in order to check if DNA was adsorbed by the inner wall of the capillary, a fraction was separately collected before the reaction solution was injected.

<Electrophoresis Condition>

Capillary length: 80 cm

Running buffer: 100 mM boric acid buffer (pH 8.4)

Temperature cartridge: 25° C.

Sample storage: 15° C.

Dynamic range: 1000 RFU

Excitation wavelength: 488 nm

Emission wavelength: 520 nm

TABLE 15

| | | |
|---|---|---|
| 100 mM NaOH | 20 psi | 8 min |
| Water | 20 psi | 8 min |
| Running buffer | 20 psi | 8 min |
| Inject | 0.5 psi | 16 sec |
| Selection | 18 kV | 25 min |
| Water | 20 psi | 4 min |
| RNase | 20 psi | 8 min |
| Water | 20 psi | 8 min |

[Confirmation of the Concentration of Modified DNA Library by PCR (the First PCR) in the Separately Collected and Fractionated Liquid]

A reaction solution was prepared in a 500 μL microtube as follows. This was set in a gene amplification apparatus to carry out the first PCR using the fraction that was concentrated in the above selection as a template in the following temperature condition. The PCR product was checked by 10% denatured polyacrylamide gel electrophoresis (TBE buffer, 200 V, 45° C., 35 min) followed by external laser (488 nm) irradiation. The reaction solution was subjected to ethanol precipitation using sodium acetate followed by freeze drying. The residue was then dissolved in 200 μL of distilled water. This solution was used a template for the second PCR.

TABLE 16

Reaction condition where KOD Dash DNA polymerase was used

| <Scale> | mother liquor | final | amount used |
|---|---|---|---|
| Primer | | | |
| GOL#P1P | 4 μM | 0.2 μM | 0.5 μL |
| GOL#P2H | 4 μM | 0.2 μM | 0.5 μL |
| Template | | | |
| solution taken Substrate | | | 4 μL |
| dNTPs | 2 mM | 0.2 mM | 1 μL |
| KOD Dash buffer | 10× | 1× | 1 μL |
| Water | | | 1 μL |
| KOD Dash | 0.025 U/μL | 0.005 U/μL | 2 μL |
| total | | | 10 μL |

TABLE 17

| Condition | | | |
|---|---|---|---|
| Preheating | 94° C. | 1 min | |
| Denature | 94° C. | 0.5 min | |
| Annealing | 54° C. | 0.5 min | 20 cycle |
| Extension | 74° C. | 1 min | |
| Final incubation | 74° C. | 5 min | |

[The Second PCR and Preparation of Template Strand]

A reaction solution was prepared in a 1.5 mL microtube as follows. This was aliquoted into eight parts, each of which contained 100 μL in a 500 μL microtube, and set in a gene amplification apparatus to carry out symmetric PCR using the first PCR product obtained above in the following temperature condition. The PCR product was checked by 10% denatured polyacrylamide gel electrophoresis (TBE buffer, 200 V, 45° C., 35 min) followed by external laser (488 nm) irradiation. The reaction solution was subjected to ethanol precipitation using sodium acetate followed by freeze drying. The residue was then dissolved in 80 μL of distilled water. According to the conventional method, GOL#P1P extended strand was selectively broken down using k-exonuclease, thereby obtaining a template strand for preparing a modified DNA library in the next round.

TABLE 18

Reaction condition where KOD Dash DNA polymerase was used

| <Scale> | mother liquor | final | amount used |
|---|---|---|---|
| Primer | | | |
| GOL#P1P | 4 μM | 0.4 μM | 80 μL |
| GOL#P2H | 4 μM | 0.4 μM | 80 μL |
| Template | | | |
| solution prepared by 1$^{st}$ PCR Substrate | | | 80 μL |
| dNTPs | 2 mM | 0.2 mM | 80 μL |
| KOD Dash buffer | 10× | 1× | 80 μL |
| Water | | | 320 μL |
| KOD Dash | 0.05 U/μL | 0.005 U/μL | 80 μL |
| total | | | 800 μL |

TABLE 19

| Condition | | | |
|---|---|---|---|
| Preheating | 94° C. | 1 min | |
| Denature | 94° C. | 0.5 min | |
| Annealing | 54° C. | 0.5 min | 16 cycle |
| Extension | 74° C. | 1 min | |
| Final incubation | 74° C. | 5 min | |

TABLE 20

Reaction condition where λ-exonuclease was used

| <Scale> | mother liquor | final | amount used |
|---|---|---|---|
| Template | | | |
| Solution prepared by 2$^{nd}$ PCR | 4 μM | 0.4 μM | 80 μL |
| Reaction buffer | 10× | 1× | 80 μL |
| Water | | | 560 μL |
| λ-exonuclease | 0.25 U/μl | 0.025 U/μl | 80 μL |
| total | | | 800 μL |

A VEGF-binding aptamer was selected by repeating the selection by the above NECEEM and PCR operation. The sequence of VEGF-binding aptamer obtained from the library that includes KK10 is shown in FIG. 11.

The Results of $K_d$ Measurement

Figure 12:
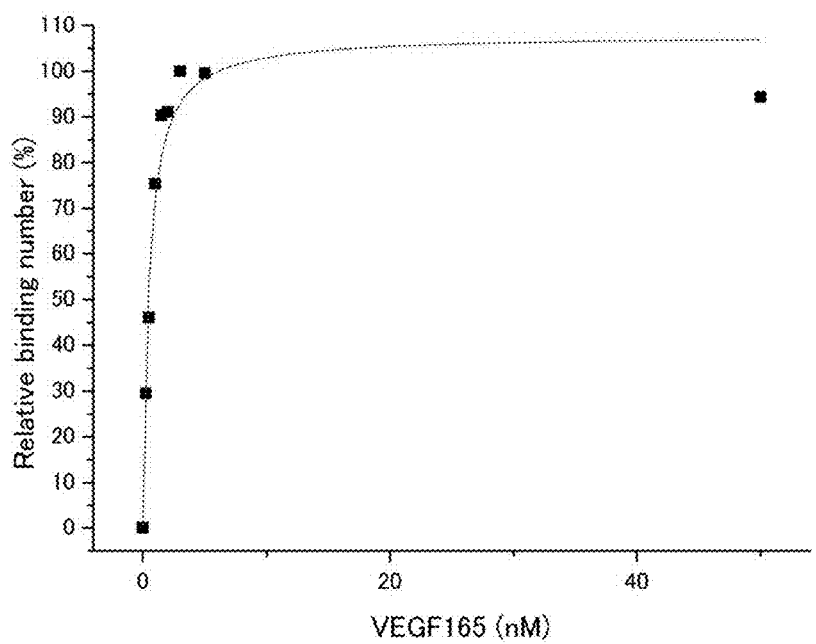
FIG. 12 is a figure showing the result of Kd value measurement for aptamer KK10#36.
Figure 13:
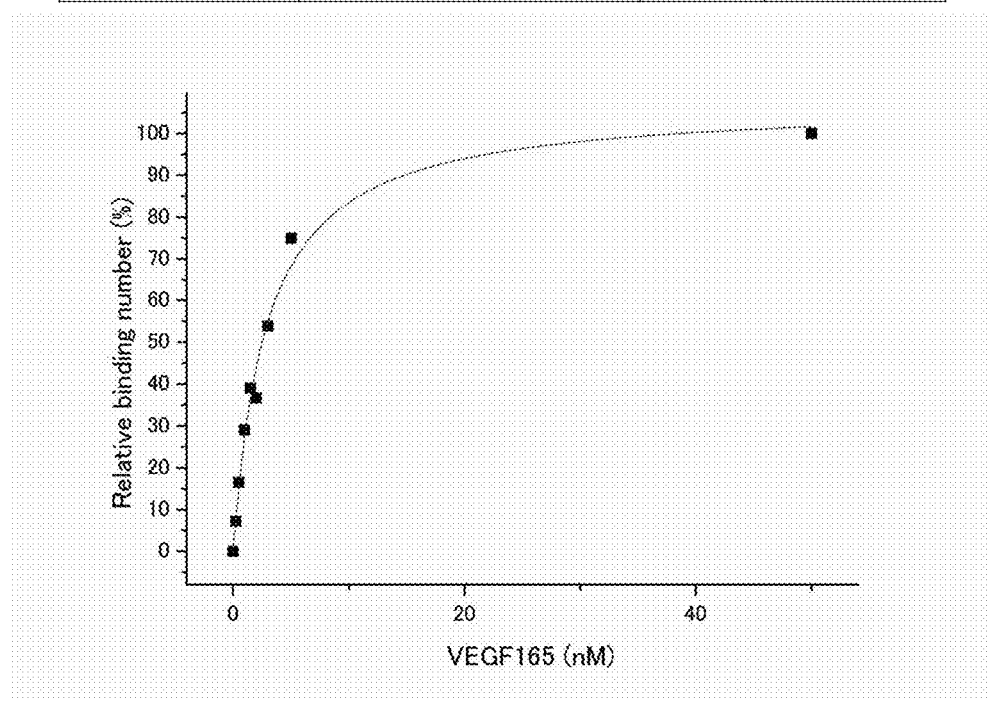
FIG. 13 is a figure showing the result of Kd value measurement for aptamer KK10#38.

Of the VEGF-binding aptamers obtained above, part of them was evaluated for their activity using CE (capillary electrophoresis). Further, a capillary with a length of 30.2 cm was used; and injection time was set to 12 sec. The rest of the condition is the same. The complex mean and standard deviation were calculated by carrying out the measurement three times. The results are shown in FIG. 12 and FIG. 13.

It has been found that all of the aptamers exhibit high affinity with VEGF.

INDUSTRIAL APPLICABILITY

The nucleoside derivative or the like of the present invention can be used as a raw material for producing a nucleic acid aptamer with excellent binding affinity and can be applied as nucleic acid medicine, biomarker test reagents, research reagents, or the like.

What is claimed is:

1. A nucleoside derivative of formula (I-1) or a pharmaceutically acceptable salt thereof, a 5'-phosphate ester of formula (III-1) or a pharmaceutically acceptable salt thereof, or a 3'-phosphoramidite of formula (IV-1):

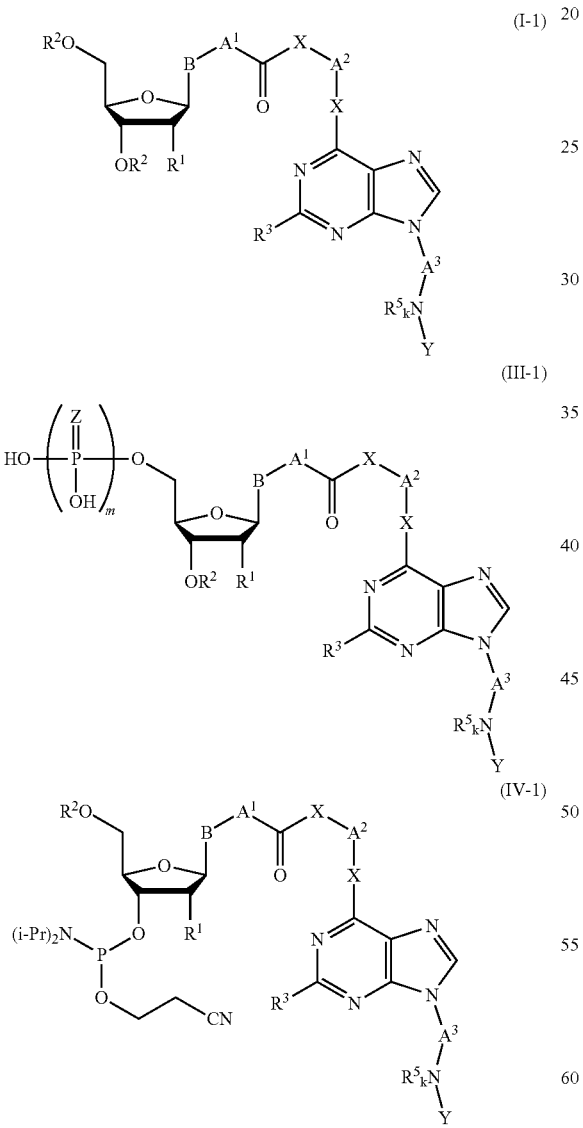

wherein in formula (I-1) and formula (III-1):
$R^1$ is a hydrogen atom (—H), a fluorine atom (—F), a hydroxyl group (—OH), an amino group (—NH$_2$), or a mercapto group (—SH);

each $R^2$ independently is a hydrogen atom (—H) or a protective group of a hydroxyl group;

$R^3$ is a hydrogen atom (—H), a hydroxyl group (—OH), an amino group (—NR$^5{}_2$), a mercapto group (—SH), or a hydrocarbyl group having one to 20 carbon atoms that optionally contains at least one substituent selected from the group consisting of an amino group (—NH$_2$), a nitro group (—NO$_2$), a cyano group (—CN), and an isocyanate group (—NCO);

$R^5$ is a hydrogen atom (—H) or a hydrocarbyl group having one to six carbon atoms;

$A^1$ is a divalent hydrocarbyl group having two to ten carbon atoms that optionally contains a branched structure and/or an unsaturated bond;

$A^2$ and $A^3$ each independently is a divalent hydrocarbyl group having two to 12 carbon atoms that optionally contains a branched structure and/or an unsaturated bond;

each X independently is an imino group (—NR$^5$—), an ether group (—O—), or a thioether group (—S—);

Y is a hydrogen atom (—H) or a hydrocarbyl group having one to 20 carbon atoms that optionally contains at least one substituent selected from the group consisting of an amino group (—NH$_2$), a nitro group (—NO$_2$), a cyano group (—CN), an isocyanate group (—NCO), and a halogen atom;

Z is an oxygen atom or a sulfur atom;

k is 1;

m is 1 to 5; and

B is a base structure represented by any one of formulae (II-1) to (II-4):

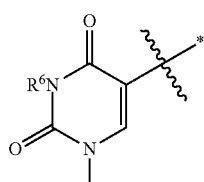

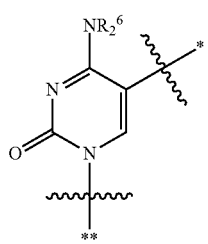

-continued

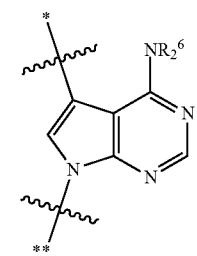
(II-3)

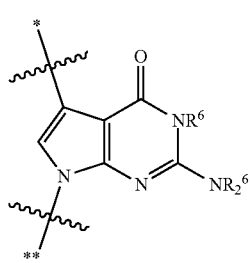
(II-4)

wherein, in formulae (II-1) to (II-4), each $R^6$ independently is a hydrogen atom (—H), a hydrocarbyl group having one to six carbon atoms, or a protective group of an amino group, * denotes connectivity through $A^1$ and ** denotes connectivity through the furanyl group in the nucleoside derivative of formula (I-1) or the 5'-phosphate ester formula (III-1), and wherein in formula (IV-1):

$R^1$ is a hydrogen atom (—H) or a fluorine atom (—F);

$R^2$ is a protective group of a hydroxyl group;

$R^3$ is a hydrogen atom (—H) or a hydrocarbyl group having one to 20 carbon atoms that optionally contains at least one substituent selected from the group consisting of a nitro group (—NO$_2$), a cyano group (—CN), and an isocyanate group (—NCO);

$R^5$ is a hydrocarbyl group having one to six carbon atoms;

$A^1$ is a divalent hydrocarbyl group having two to ten carbon atoms that optionally contains a branched structure and/or an unsaturated bond;

$A^2$ and $A^3$ each independently is a divalent hydrocarbyl group having two to 12 carbon atoms that optionally contains a branched structure and/or an unsaturated bond;

each X independently is an imino group (—NR$^5$—), an ether group (—O—), or a thioether group (—S—);

Y is a hydrogen atom (—H) or a hydrocarbyl group having one to 20 carbon atoms that optionally contains at least one substituent selected from the group consisting of a nitro group (—NO$_2$), a cyano group (—CN), an isocyanate group (—NCO), and a halogen atom;

k is 1; and

B is a base structure represented by any one of formulae (II-1) to (II-4):

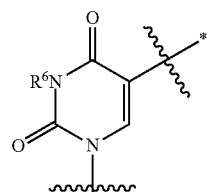
(II-1)

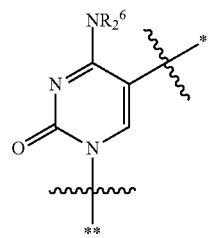
(II-2)

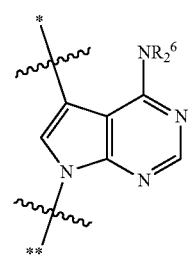
(II-3)

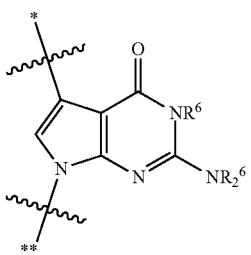
(II-4)

wherein, in formulae (II-1) to (II-4), each $R^6$ independently is a hydrogen atom (—H), a hydrocarbyl group having one to six carbon atoms, or a protective group of an amino group, each $R^{6'}$ independently is a hydrocarbyl group having one to six carbon atoms or a protective group of an amino group, * denotes connectivity through $A^1$ and ** denotes connectivity through the furanyl group in the 3'-phosphoramidite of formula (IV-1).

2. A 5'-phosphate ester of formula (III-1) according to claim 1 or a pharmaceutically acceptable salt thereof.

3. A substrate solution comprising the 5'-phosphate ester or a pharmaceutically acceptable salt thereof according to claim 2 and a solvent, wherein the 5'-phosphate ester or pharmaceutically acceptable salt thereof is optionally labeled with a fluorescent substituent.

4. A method of producing a polynucleotide comprising applying, as a substrate for synthesis, the 5'-phosphate ester or a pharmaceutically acceptable salt thereof according to claim 2, wherein m is 3 and the 5'-phosphate ester or pharmaceutically acceptable salt thereof is optionally labeled with a fluorescent substituent.

5. A polynucleotide that contains, as a building block, the 5'-phosphate ester of formula (III-1) according to claim 2, wherein m is 1, a pharmaceutically acceptable salt thereof, and/or a phosphorothioated product thereof having formula (V-1):

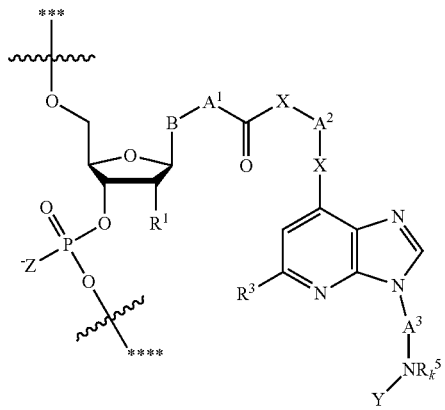

(V-1)

wherein
$R^1$ is a hydrogen atom (—H), a fluorine atom (—F), a hydroxyl group (—OH), an amino group (—NH$_2$), or a mercapto group (—SH);
$R^3$ is a hydrogen atom (—H), a hydroxyl group (—OH), an amino group (—NR$^5{}_2$), a mercapto group (—SH), or a hydrocarbyl group having one to 20 carbon atoms that optionally contains at least one substituent selected from the group consisting of an amino group (—NH$_2$), a nitro group (—NO$_2$), a cyano group (—CN), an isocyanate group (—NCO);
each $R^5$ independently is a hydrogen atom (—H) or a hydrocarbyl group having one to six carbon atoms;
$A^1$ is a divalent hydrocarbyl group having two to ten carbon atoms that optionally contains a branched structure and/or an unsaturated bond;
$A^2$ and $A^3$ each independently is a divalent hydrocarbyl group having two to 12 carbon atoms that optionally contains a branched structure and/or an unsaturated bond;
each X independently is an imino group (—NR$^5$—), an ether group (—O—), or a thioether group (—S—);
Y is a hydrogen atom (—H) or a hydrocarbyl group having one to 20 carbon atoms that optionally contains at least one substituent selected from the group consisting of an amino group (—NH$_2$), a nitro group (—NO$_2$), a cyano group (—CN), an isocyanate group (—NCO), and a halogen atom;
Z is a sulfur atom;
k is 1;
B is a base structure represented by any one of formulae (II-1) to (II-4):

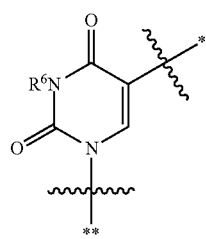

(II-1)

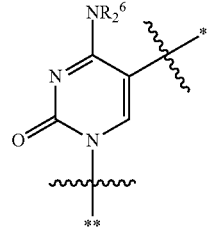

(II-2)

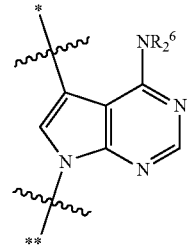

(II-3)

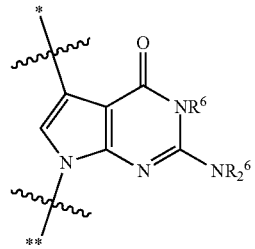

(II-4)

wherein, in formulae (II-1) to (II-4), each $R^6$ independently is a hydrogen atom (—H), a hydrocarbyl group having one to six carbon atoms, or a protective group of an amino group, * denotes connectivity through $A^1$ and ** denotes connectivity through the furanyl group in the nucleoside derivative of formula (V-1);
*** denotes connectivity to a 3' position of a furanyl ring of the attached nucleotide; and
**** denotes connectivity to a 5' position of a furanyl ring of the attached nucleotide.

6. A polynucleotide library comprising at least one polynucleotide according to claim 5.

7. A 3'-phosphoramidite of formula (IV-1) according to claim 1.

8. A substrate solution comprising the 3'-phosphoramidite of formula (IV-1) according to claim 7 and a solvent, wherein the 3'-phosphoramidite is optionally labeled with a fluorescent substituent.

9. A method of producing a polynucleotide comprising applying, as a substrate for synthesis, the 3'-phosphoramidite according to claim 7, wherein the 3'-phosphoramidite is optionally labeled with a fluorescent substituent.

10. A vesicular endothelial growth factor binding agent that contains a nucleic acid aptamer containing a 5'-monophosphate nucleotide residue derived from the modified 5'-triphosphate nucleotide of formula (i):

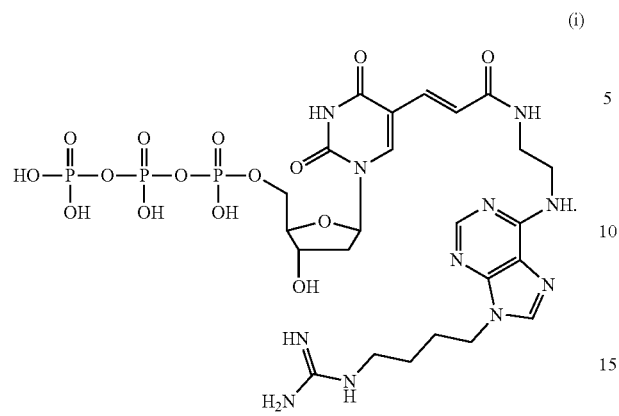

(i)

11. The vesicular endothelial growth factor binding agent according to claim 10, wherein the nucleic acid aptamer is a single-stranded DNA.

12. The vesicular endothelial growth factor binding agent according to claim 10, wherein the nucleic acid aptamer has a length of 15 to 100 bases.

13. The vesicular endothelial growth factor binding agent according to claim 10, wherein the sequence of the nucleic acid aptamer contains the sequence of nucleotides 21 to 50 of any of SEQ ID NOs: 6 to 31 and 33 to 40 or nucleotides 21 to 49 of SEQ ID NO: 32 in which a thymine residue (T) in these sequences is replaced by a residue derived from the compound of formula (i).

\* \* \* \* \*

SEQUENCE LISTING

<160> NUMBER OF SEQ ID NOS: 40

<210> SEQ ID NO 1
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1
ggattagcga acaggccata cctt                                              24

<210> SEQ ID NO 2
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 2
gcgaaaaaag gtatggcctg ttcgctaatc c                                      31

<210> SEQ ID NO 3
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 3
tcgctcggca ggatcgcaag                                                   20

<210> SEQ ID NO 4
<211> LENGTH: 70
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (21)..(50)
<223> OTHER INFORMATION: n is a, c, g, or t

<400> SEQUENCE: 4
tgctgccact gctccgtcca nnnnnnnnnn nnnnnnnnnn nnnnnnnnnn cttgcgatcc        60
tgccgagcga                                                              70

<210> SEQ ID NO 5
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 5
tgctgccact gctccgtcca                                                   20

<210> SEQ ID NO 6
<211> LENGTH: 70
<212> TYPE: DNA
<213> ORGANISM: Artificial Sequence

```
<220> FEATURE:
<223> OTHER INFORMATION: Synthetic Sequence

<400> SEQUENCE: 6
tcgctcggca ggatcgcaag aaggatgatc gataagcggt ctatagaggg tggacggagc    60
agtggcagca                                                           70

<210> SEQ ID NO 7
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 7
tcgctcggca ggatcgcaag atccatgtaa cggctgttag ctcataggac tggacggagc    60
agtggcagca                                                           70

<210> SEQ ID NO 8
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 8
tcgctcggca ggatcgcaag tcaggcgctt ggcatgctcg atgagtctgg tggacggagc    60
agtggcagca                                                           70

<210> SEQ ID NO 9
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 9
tcgctcggca ggatcgcacg ggcgaagggg aacagatatt ctctgatgca tggacggagc    60
agtggcacaa                                                           70

<210> SEQ ID NO 10
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 10
tcgctcggca ggatcgcaag ggcagtgagt tgttaagtac ccacatgaag tggacggagc    60
agtggcagca                                                           70

<210> SEQ ID NO 11
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 11
tcgctcggca ggatcgcaag cgtggatacg gtactaaacg aagtaaccct tggacggagc    60
agtggcagca                                                           70
```

<210> SEQ ID NO 12
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 12
tcgctcggca ggatcgcaag ccgagactgc gttgtagggg caagtggcaa tggacggagc    60
agtggcagca                                                           70

<210> SEQ ID NO 13
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 13
tcgctcggca ggatcgcaag ggcgtgaccg gttcattcct taatttacaa tggacggagc    60
agtggcagca                                                           70

<210> SEQ ID NO 14
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 14
tcgctcggca ggatcgcaag gaacctctac ctaggctacg tacttgcggc tggacggagc    60
agtggcagca                                                           70

<210> SEQ ID NO 15
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 15
tcgctcggca ggatcgcaag agagaccaca gctgagttgt atacgagaag tggacggagc    60
agtggcagca                                                           70

<210> SEQ ID NO 16
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 16
tcgctcggca ggatcgcacg cgtgaacttg tattcacgag cggtaacaca tggacggagc    60
agtggcagca                                                           70

<210> SEQ ID NO 17
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 17
tcgctcggca ggatcgcaag agcggggtta gtatagttct ggaatgaagt tggacggagc    60
agtggcagca                                                           70

<210> SEQ ID NO 18
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 18
tcgctcggca ggatcgcaag atagcatccc acggtttcta attgctacgc tggacggagc    60
agtggcagca                                                           70

<210> SEQ ID NO 19
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 19
tcgctcggca ggatcgcaag cgtgagaagg atgggggtct gaggttgagt tggacggagc    60
agtggcagca                                                           70

<210> SEQ ID NO 20
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 20
tcgctcggca ggatcgcaag gacaagtacc tttgcacgcg ctcactacct tggacggagc    60
agtggcagca                                                           70

<210> SEQ ID NO 21
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 21
tcgctcggca ggatcgcaag gacatgtacc tttgcacgcg ctcactacct tggacggagc    60
agtggcagca                                                           70

<210> SEQ ID NO 22
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 22
tcgctcggca ggatcgcaag gagttcatga ggggaaaatg tggggtgacc tggacggagc    60
agtggcagca                                                           70

<210> SEQ ID NO 23
<211> LENGTH: 70
<212> TYPE: DNA

```
<213> ORGANISM: Artificial Sequence
<220> FEATURE:
<223> OTHER INFORMATION: Synthetic Sequence

<400> SEQUENCE: 23
tcgctcggca ggatcgcaag gagttcatga ggggaaaatg tggggtgact tggacggagc    60
agtggcagca                                                           70

<210> SEQ ID NO 24
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 24
tcgctcggca ggatcgcaag ctagggtgtc ggcacgaact aacaaaactg tggacggagc    60
agtggcagca                                                           70

<210> SEQ ID NO 25
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 25
tcgctcggca ggatcgcacg ctagggtgtc ggcacgaact aacaaaactg tggacggagc    60
agtggcagca                                                           70

<210> SEQ ID NO 26
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 26
tcgctcggca ggatcgcaag tatggccgga tggcatagga ttctccttcg tggacggagc    60
agtggcagca                                                           70

<210> SEQ ID NO 27
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 27
tcgctcggca ggatcgcacg tatggccgga tggcatagga ttctccttcg tggacggagc    60
agtggcagca                                                           70

<210> SEQ ID NO 28
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 28
tcgctcggca ggatcgcacg gaggttcatg aaaaaataaa cggtggtcca tggacggagc    60
agtggcagca                                                           70
```

-continued

<210> SEQ ID NO 29
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 29
tcgctcggca ggatcgcaag gaggttcatg aaaaaataaa cggtggtcca tggacggagc    60
agtggcagca                                                          70

<210> SEQ ID NO 30
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 30
tcgctcggca ggatcgcaag gaggttcatg aagaaataaa cggtggtcca tggacggagc    60
agtggcagca                                                          70

<210> SEQ ID NO 31
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 31
tcgctcggca ggatcgcaag agcgtgagag cttagaattc ccacttgagc tggacggagc    60
agtggcagca                                                          70

<210> SEQ ID NO 32
<211> LENGTH: 69
<212> TYPE: DNA
<213> ORGANISM: Artificial Sequence
<220> FEATURE:
<223> OTHER INFORMATION: Synthetic Sequence

<400> SEQUENCE: 32
tcgctcggca ggatcgcaag acgtgagagc ttagaattcc cacttgagct ggacggagca    60
gtggcagca                                                           69

<210> SEQ ID NO 33
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 33
tcgctcggca ggatcgcatg agcgtgagag cttagaattc ccacttgagc tggacggagc    60
agtggcagca                                                          70

<210> SEQ ID NO 34
<211> LENGTH: 70
<212> TYPE: DNA
<213> ORGANISM: Artificial Sequence
<220> FEATURE:
<223> OTHER INFORMATION: Synthetic Sequence

```
<400> SEQUENCE: 34
tcgctcggca ggatcgcacg agcgtgagag cttagaattc ccacttgagt tggacggagc    60
agtggcagca                                                          70

<210> SEQ ID NO 35
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 35
tcgctcggca ggatcgcaag tcgcgtttaa gggtaagtag ggcattgtca tggacggagc    60
agtggcagca                                                          70

<210> SEQ ID NO 36
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 36
tcgctcggca ggatcgcaag tcgcgtttaa gggtaagtag ggcattgcca tggacggagc    60
agtggcagca                                                          70

<210> SEQ ID NO 37
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 37
tcgctcggca ggatcgcaag ccgcgtttaa gggtaagtag ggcattgtca tggacggagc    60
agtggcagca                                                          70

<210> SEQ ID NO 38
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 38
tcgctcggca ggatcgcacg tcgcgtttaa gggtaagtag ggcattgtca tggacggagc    60
agtggcagca                                                          70

<210> SEQ ID NO 39
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 39
tcgctcggca ggatcgcaag tcgcgtttaa ggggaagtag ggcattgtca tggacggagc    60
agtggcagca                                                          70

<210> SEQ ID NO 40
<211> LENGTH: 70
```

```
<212> TYPE: DNA
<213> ORGANISM: Artificial Sequence
<220> FEATURE:
<223> OTHER INFORMATION: Synthetic Sequence

<400> SEQUENCE: 40
tcgctcggca ggatcgcaag tcgagtttaa gggtaagtag ggcattgtca tggacggagc    60
agtggcagca                                                            70
```